(12) United States Patent
Toth et al.

(10) Patent No.: US 9,956,034 B2
(45) Date of Patent: May 1, 2018

(54) SYSTEMS, METHODS, AND DEVICES FOR MONITORING AND TREATMENT OF TISSUES WITHIN AND/OR THROUGH A LUMEN WELL

(71) Applicant: Autonomix Medical, Inc., Excelsior, MN (US)

(72) Inventors: Landy Toth, Doylestown, PA (US); Roy Martin, Maple Grove, MN (US)

(73) Assignee: AUTONOMIX MEDICAL, INC., Excelsior, MN (US)

( * ) Notice: Subject to any disclaimer, the term of this patent is extended or adjusted under 35 U.S.C. 154(b) by 352 days.

(21) Appl. No.: 14/439,989

(22) PCT Filed: Oct. 31, 2013

(86) PCT No.: PCT/US2013/067726
§ 371 (c)(1),
(2) Date: Apr. 30, 2015

(87) PCT Pub. No.: WO2014/070999
PCT Pub. Date: May 8, 2014

(65) Prior Publication Data
US 2015/0289929 A1  Oct. 15, 2015

Related U.S. Application Data

(60) Provisional application No. 61/722,264, filed on Nov. 5, 2012.

(51) Int. Cl.
*A61B 18/18* (2006.01)
*A61B 18/14* (2006.01)
(Continued)

(52) U.S. Cl.
CPC ............ *A61B 18/1492* (2013.01); *A61B 5/04* (2013.01); *A61B 5/6852* (2013.01);
(Continued)

(58) Field of Classification Search
CPC ................ A61B 18/1492; A61B 18/18; A61B 2018/00577; A61N 5/04; A61N 5/6852;
(Continued)

(56) References Cited

U.S. PATENT DOCUMENTS

| 6,014,579 A | 1/2000 | Pomeranz et al. |
| 7,006,859 B1 * | 2/2006 | Osorio ................. A61B 5/0478 600/378 |

(Continued)

FOREIGN PATENT DOCUMENTS

| EP | 2495011 A1 | 9/2012 |
| WO | WO9942047 A1 | 8/1999 |

(Continued)

*Primary Examiner* — Mallika D Fairchild
(74) *Attorney, Agent, or Firm* — Ryan, Mason & Lewis, LLP

(57) ABSTRACT

A system for controlled sympathectomy procedures is disclosed. A system for controlled micro ablation procedures is disclosed. Methods for performing a controlled surgical procedure are disclosed. A system for performing controlled surgical procedures in a minimally invasive manner is disclosed. Systems and methods for accessing target tissues as part of a neuromodulation procedure from within a lumen are disclosed.

37 Claims, 12 Drawing Sheets

(51) Int. Cl.

| | |
|---|---|
| *A61N 7/02* | (2006.01) |
| *A61B 5/04* | (2006.01) |
| *A61B 5/00* | (2006.01) |
| *A61N 1/05* | (2006.01) |
| *A61N 1/30* | (2006.01) |
| *A61B 17/00* | (2006.01) |
| *A61B 18/00* | (2006.01) |
| *A61B 18/02* | (2006.01) |

(52) U.S. Cl.
CPC .......... *A61B 5/6858* (2013.01); *A61B 5/7203* (2013.01); *A61B 18/18* (2013.01); *A61N 1/05* (2013.01); *A61N 1/303* (2013.01); *A61N 7/022* (2013.01); *A61B 2017/003* (2013.01); *A61B 2017/00053* (2013.01); *A61B 2017/00247* (2013.01); *A61B 2017/00256* (2013.01); *A61B 2018/0022* (2013.01); *A61B 2018/00184* (2013.01); *A61B 2018/00202* (2013.01); *A61B 2018/00214* (2013.01); *A61B 2018/00267* (2013.01); *A61B 2018/00279* (2013.01); *A61B 2018/00285* (2013.01); *A61B 2018/00404* (2013.01); *A61B 2018/00434* (2013.01); *A61B 2018/00511* (2013.01); *A61B 2018/00547* (2013.01); *A61B 2018/00577* (2013.01); *A61B 2018/00642* (2013.01); *A61B 2018/00744* (2013.01); *A61B 2018/00839* (2013.01); *A61B 2018/00875* (2013.01); *A61B 2018/0212* (2013.01); *A61B 2018/143* (2013.01); *A61B 2018/1425* (2013.01); *A61B 2018/1427* (2013.01); *A61B 2018/1475* (2013.01); *A61B 2218/002* (2013.01); *A61N 2007/025* (2013.01)

(58) Field of Classification Search
CPC ...... A61N 5/6858; A61N 5/7203; A61N 1/05; A61N 1/303
See application file for complete search history.

(56) References Cited

U.S. PATENT DOCUMENTS

| | | | |
|---|---|---|---|
| 7,077,822 B1* | 7/2006 | Howard, III | A61N 1/0529 600/378 |
| 7,937,143 B2* | 5/2011 | Demarais | A61N 1/0514 604/21 |
| 2008/0027346 A1* | 1/2008 | Litt | A61B 5/0478 600/544 |
| 2009/0192579 A1 | 7/2009 | Ransbury et al. | |
| 2010/0010567 A1 | 1/2010 | Deem et al. | |
| 2010/0100152 A1* | 4/2010 | Martens | A61N 1/0534 607/45 |
| 2011/0275951 A1 | 11/2011 | Lips et al. | |
| 2012/0136263 A1 | 5/2012 | Prakash et al. | |
| 2013/0085489 A1* | 4/2013 | Fain | A61N 1/36007 606/34 |
| 2013/0116681 A1* | 5/2013 | Zhang | A61B 18/1206 606/34 |

FOREIGN PATENT DOCUMENTS

| | | |
|---|---|---|
| WO | 2009/135075 A1 | 11/2009 |
| WO | 2012027320 A2 | 3/2012 |
| WO | WO02012/027320 A2 * | 3/2012 |
| WO | PCT/US2013/067726 | 8/2014 |

* cited by examiner

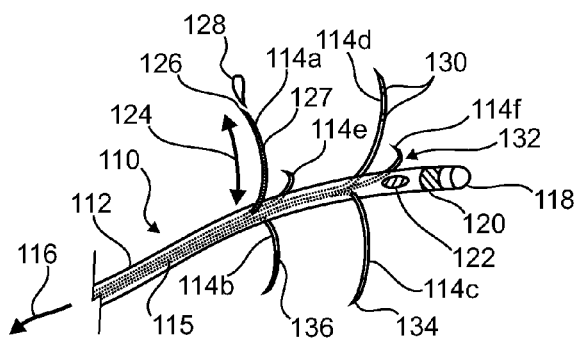
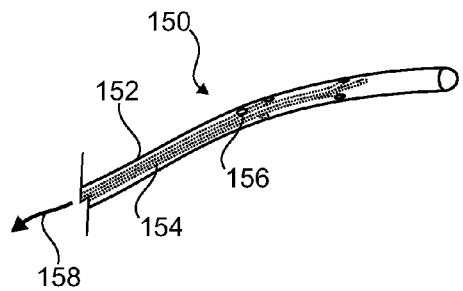
Fig 1a
Fig 1b
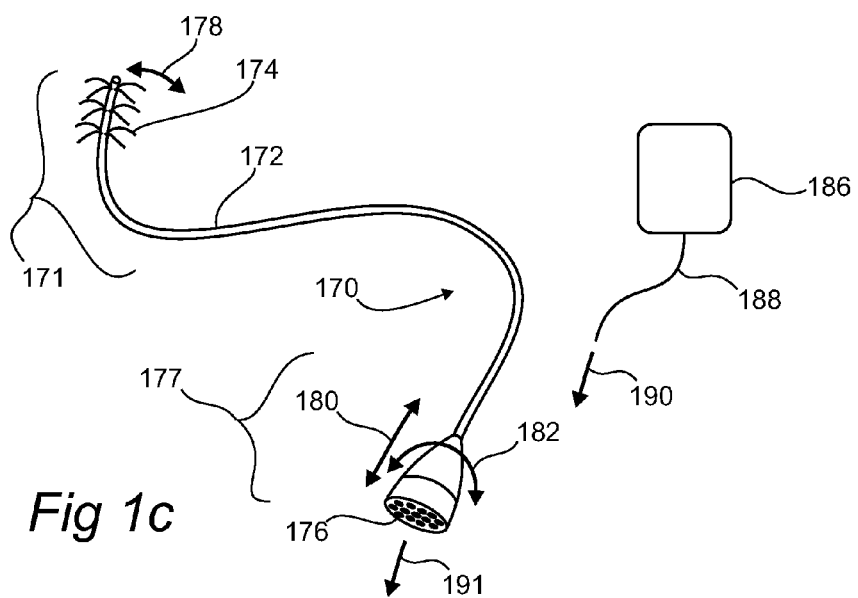
Fig 1c
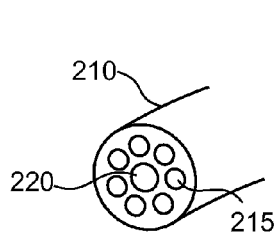
Fig 2a
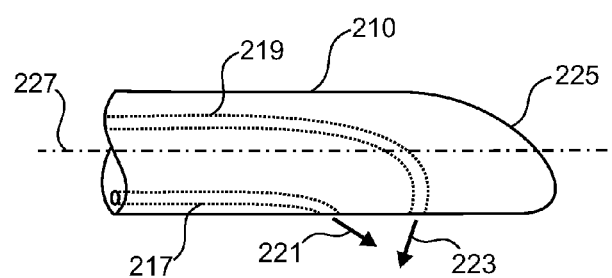
Fig 2b

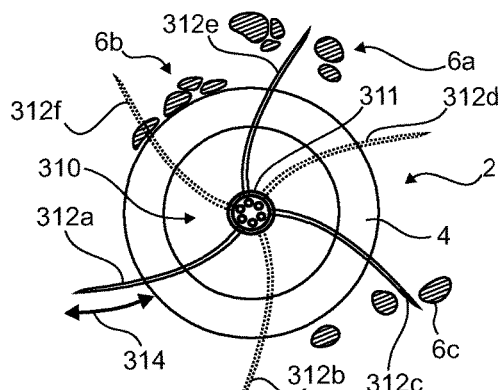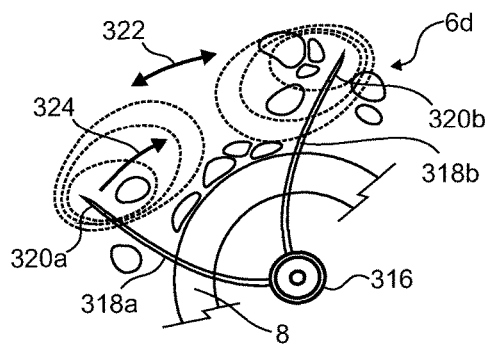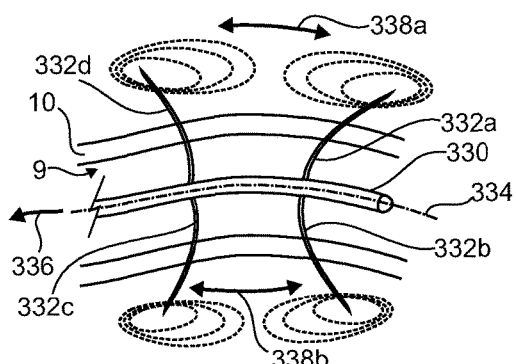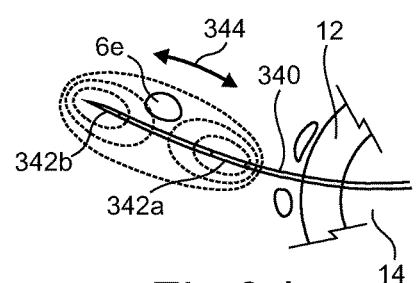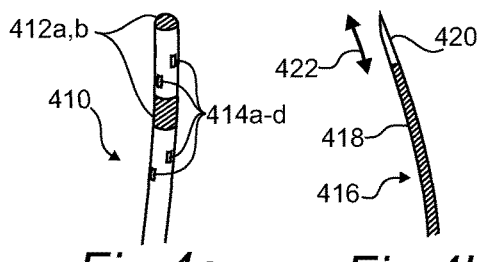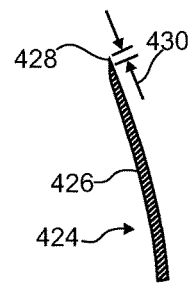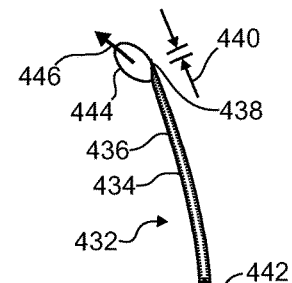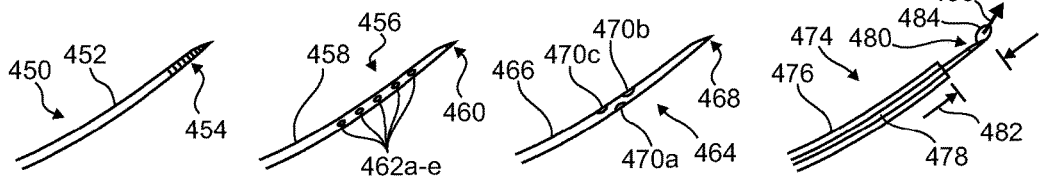

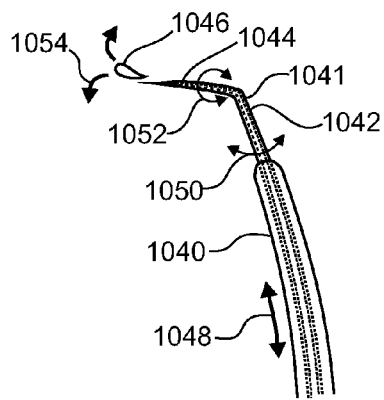
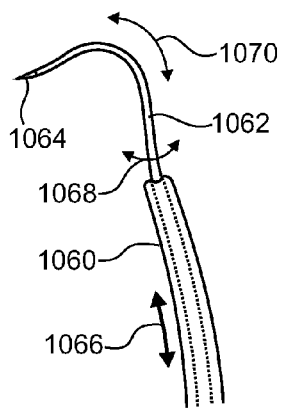
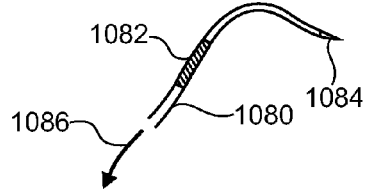
Fig 10c  Fig 10d  Fig 10e
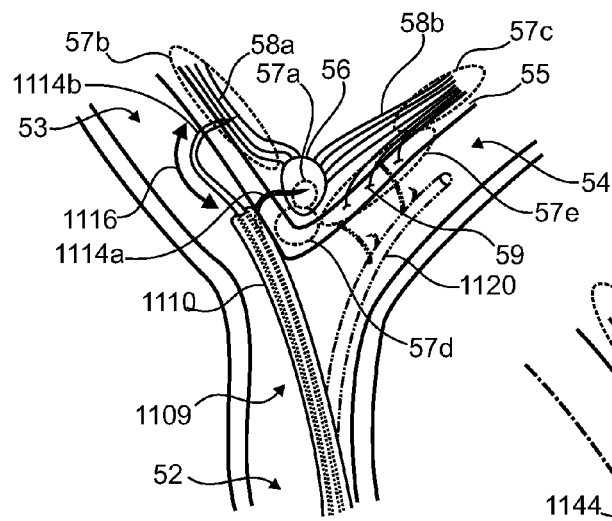
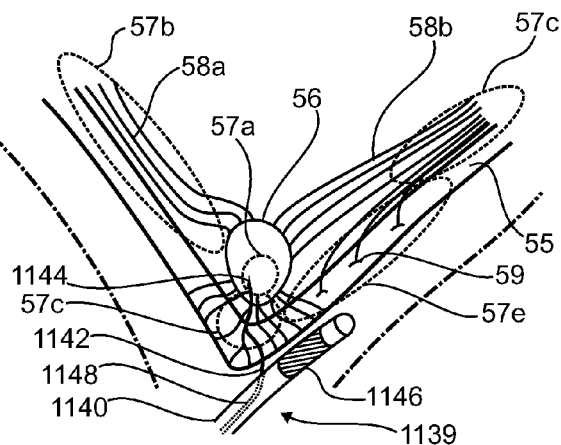
Fig 11a  Fig 11b
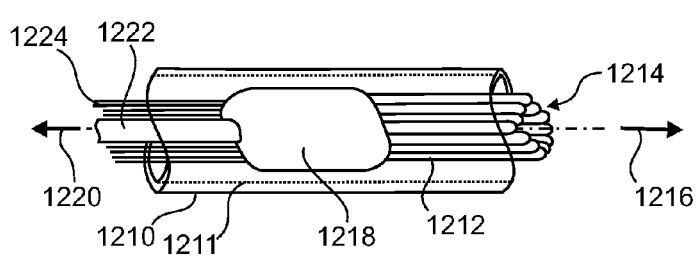
Fig 12

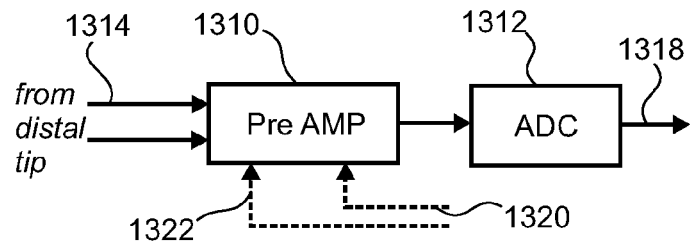
Fig 13a
Fig 13b
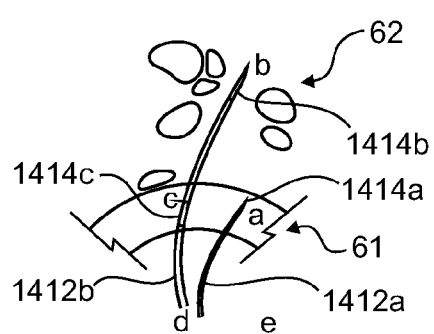
Fig 14a
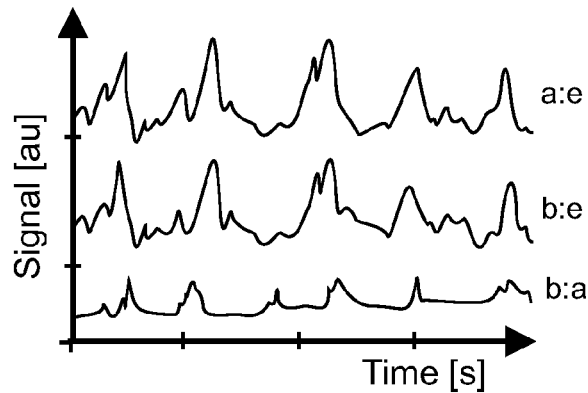
Fig 14b
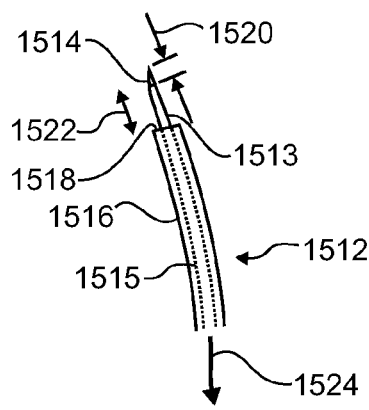
Fig 15a
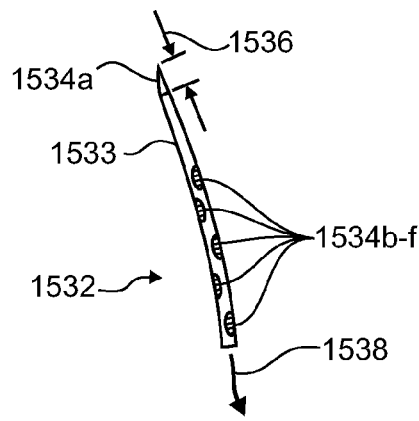
Fig 15b

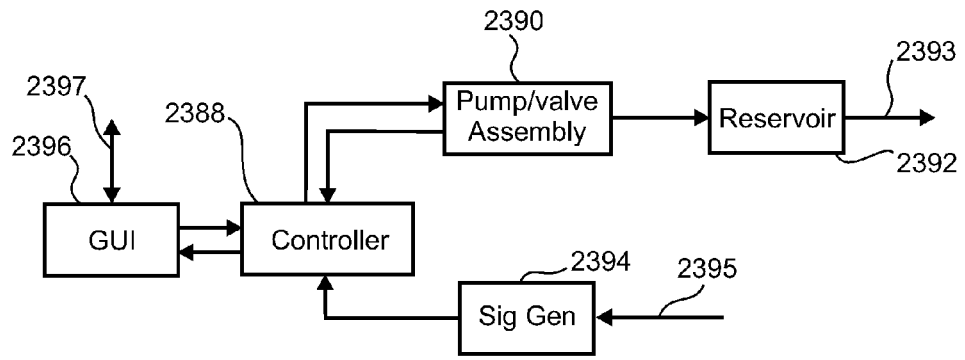
*Fig 23e*
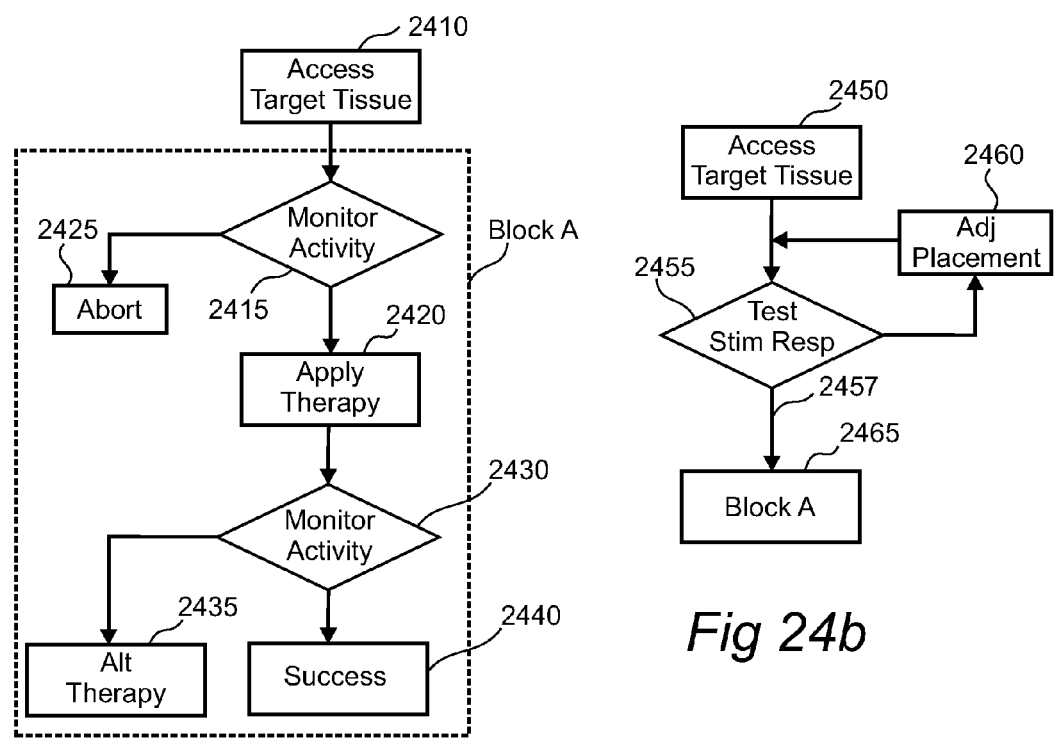
*Fig 24a*
*Fig 24b*

SYSTEMS, METHODS, AND DEVICES FOR MONITORING AND TREATMENT OF TISSUES WITHIN AND/OR THROUGH A LUMEN WELL

CROSS-REFERENCE TO RELATED APPLICATION

The present application is a national stage application of International Application No. PCT/US2013/067726 which claims benefit of and priority to U.S. Provisional Application Ser. No. 61/722,264 filed on Nov. 5, 2012, entitled "Systems and Methods for Treatment of and/or Through a Lumen Wall", by Landy Toth et al., the entire contents of which are incorporated by reference herein for all purposes.

BACKGROUND

Technical Field

The present disclosure relates to the field of monitoring and/or surgical modification of neurological and/or receptor functionality and activity. The present disclosure also relates to catheter based systems for use in nerve and/or receptor monitoring, electrophysiological monitoring, and/or surgical procedures.

Background

Congestive heart failure, hypertension, diabetes, sleep apnea, and chronic renal failure have many different initial causes; however, all may include some form of sympathetic hyperactivity. Sensory receptors and sympathetic nerves communicate signals with sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone.

Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases.

Although ablation of such nerves can have positive effects on drug resistant hypertension and glucose metabolism abnormality, current methodologies for denervation (e.g. ablation, etc.) are conducted without adequate feedback (with respect to the site of a denervation event, the extent of denervation, the effect of denervation on local physiology, etc.).

Furthermore, many conditions require access to tissues within the walls of a lumen within the body. Oftentimes, access to deeper tissues within the wall may be necessary for optimal treatment. Inner layers of tissue and damage adjacent to the lumen (e.g. intima, plaque, calcium deposits, etc.) may present complications in communicating from within the lumen out into the wall thereof to the desired tissues (e.g. electrical communication, fluid communication, and the like).

SUMMARY

One objective of this disclosure is to provide systems, devices, and methods for accessing, monitoring and/or treating a surgical site and/or tissue within a body.

Another objective is to provide systems, devices, and methods for locating, monitoring, and/or mapping electrophysiological function of one or more surgical sites before, during, and/or following a stimulus and/or a surgical procedure.

Another objective is to provide systems, devices, and methods to modify electrophysiological function of an organ, to modulate intra organ neurological traffic, and/or to modulate nervous activity (e.g. sympathetic, parasympathetic, autonomous, enteric, etc.), in a volume of tissue, and/or a surgical site, via a surgical process.

Yet another objective is to provide systems, devices, and methods for monitoring and/or altering electrophysiological activity of a volume of tissue, a surgical site, a region within an organ as part of a surgical procedure, a diagnostic procedure, and/or as part of a chronic monitoring system.

Another objective is to provide, systems, devices, and methods for interfacing with the tissues of the wall of a lumen as well as tissues exterior to the lumen, via intra lumen access (e.g. via minimally invasive procedure, via catheter access, etc.).

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a microsurgical tool for monitoring and/or altering electrophysiological activity within the vicinity of a lumen within a body, the microsurgical tool including an elongate member with a distal tip and a control end, the distal tip thereof shaped and dimensioned so as to fit within the lumen, the elongate member shaped and dimensioned so as to extend from an entry site on the body into the lumen; and one or more probes configured with a tip, the probes deploy-ably coupled with the distal tip of the elongate member, electrically, mechanically, and/or fluidly coupled to the control end of the elongate member, the tip of the probe shaped so as to penetrate into and/or through a wall of the lumen upon deployment from the elongate member, one or more of the probes including one or more electrodes, electrically coupled to the probe, one or more of the electrodes configured to convey a signal associated with and/or to alter the electrophysiological activity upon deployment.

In aspects, the electrophysiological signals may be related to and/or correspond to one or more of water concentration, tissue tone, evoked potential, remotely stimulated nervous activity, sympathetic nervous activity, an electromyographic signal [EMG], a mechanomyographic signal [MMG], a local field potential, an electroacoustic event, vasodialation, vessel wall stiffness, muscle sympathetic nerve activity [MSNA], central sympathetic drive, nerve traffic, combinations thereof, or the like.

In aspects, a microsurgical tool in accordance with the present disclosure may include a microcircuit, electrically coupled to one or more of the electrodes, the microcircuit configured to condition the conveyed signal. In aspects, the microcircuit may be embedded within the elongate member. In aspects, the microcircuit is embedded into the microsurgical tool and at least a portion of the electrical coupling is provided via the elongate member.

In aspects, a microsurgical tool in accordance with the present disclosure may include a microelectrode configured to interface with an adjacent tissue volume within or beyond the wall of the lumen, the microelectrode having an area of less than 5000 µm$^2$, less than 1000 µm$^2$, less than 250 µm$^2$, or less than 100 µm$^2$, and/or one or more stimulating electrodes electrically and mechanically coupled to one or more of the probes and/or the elongate member, the stimulating electrodes configured to provide a stimulating and/or ablating current to a tissue site in the vicinity of the wall of the lumen. In aspects, the microsurgical tool comprises a plurality of stimulating electrodes, the microsurgical tool configured to coordinate stimulating and/or ablating currents between two or more of the stimulating electrodes, the currents passing through the tissue site.

In aspects, one or more probes may include a channel, fluidly coupled with the control end of the elongate member, the microsurgical tool configured to deliver a diagnostic and/or therapeutic substance to a tissue site in the vicinity of the wall of the lumen via the channel. In aspects, one or more of the electrodes may be configured and positioned so as to monitor the effect of the stimulating and/or ablating current(s), and/or the effect of the substance on the tissue site and/or tissues related thereto. In aspects, one or more of the stimulating electrodes may have an area of greater than 0.1 mm$^2$, 0.5 mm$^2$, 1 mm$^2$, 2 mm$^2$, or 10 mm$^2$.

In aspects, the diagnostic and/or therapeutic substance may be a chemical, a drug substance, a neuromodulating substance, a neuroblocking substance, an acid, a base, a denervating agent, a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, capaicin, an anesthetic, lidocaine, tetanus toxin, quaternary ammonium salts, a pachycurare, a leptocurare, acetylcholine, aminosteroids, or a combination thereof. In aspects, the substance may be included within a restraining matrix, a partially biodegradable matrix, or the like for retention in the wall of the lumen.

In aspects, one or more of the probes may be slidingly coupled to the elongate member, sliding of the probe along the length of the elongate member providing the deployment thereof. In aspects, probe deployment may be achieved by movement of an actuator, release of a latch, retraction of a sheath, or the like. In aspects, the microsurgical tool comprises a sheath extending over the elongate member, retraction of the sheath providing the deployment of the probes.

In aspects, the tool may include a stabilizing member coupled to the elongate member, the stabilizing member configured to retain the position of the distal tip of the elongate member within the lumen upon deployment. Some non-limiting examples of stabilizing members include a balloon, a basket, a plurality of flexible members, a wire cage, an embolic filter, combinations thereof, and the like. In aspects, the stabilizing member may include one or more electrodes, configured to provide a stimulating, and/or ablating current to the wall of the lumen in accordance with the present disclosure.

In aspects, the tool may include one or more steerable probes in accordance with the present disclosure, one or more of the probes is shaped with a curved tip, the steerable probe slidingly and rotate-ably coupled with the control end of the elongate member, so as to be steerably advanced through the wall of the lumen upon deployment.

In aspects, one or more of the probes may include a stabilizing element positioned at a predetermined distance from the tip thereof, the stabilizing element configured so as to limit the depth which the probe can penetrate into the wall of the lumen upon deployment. In aspects, one or more of the probes may include a plurality of electrodes, arranged along a length thereof in relation to the tip thereof, the electrodes configured to convey precise signals pertaining to electrophysiological activity of an adjacent tissue site in the vicinity thereof, impedance between the electrodes, or the like during deployment. In aspects, the conveyed signals may relate to the depth of penetration of the probe into the wall of the lumen, to the proximity of electrophysiologically active tissues in the vicinity of the wall of the lumen in relation to the probe, or the like.

In aspects, one or more of the probes may be sized and dimensioned so as to fit within a precapillary arteriole positioned within the wall of the lumen. Such a probe may have a diameter of less than 1 mm, less than 0.5 mm, less than 0.125 mm, or the like.

According to aspects there is provided, use of a microsurgical tool in accordance with the present disclosure to monitor and/or alter electrophysiological activity in the vicinity of a vessel, an artery, a vein, a tubule, a renal artery, an organ, a kidney, a liver, a gall bladder, a carotid body, a spleen, a pancreas, a prostate, a combination thereof, or the like.

According to aspects there is provided, use of a microsurgical tool in accordance with the present disclosure to perform a surgical procedure within a body.

According to aspects there is provided, use of a microsurgical tool in accordance with the present disclosure, to determine the extent of a surgical procedure within a body.

According to aspects there is provided, use of a microsurgical tool in accordance with the present disclosure to perform a renal denervation procedure.

According to aspects there is provided, a system for altering electrophysiological activity in the vicinity of an anatomical site in the vicinity of an organ or vessel in a body accessible via a lumen, including a microsurgical tool in accordance with the present disclosure, configured to monitor the electrophysiological activity in the vicinity of the site, and to perform a surgical procedure on the site; and a control unit configured to accept signals from the microsurgical tool, and to adjust the surgical procedure dependent upon the signals, to display the signals, to evaluate the surgical procedure dependent upon the signals, to plan a surgical path for the surgical procedure dependent upon the signals, to determine the extent of the procedure dependent upon the signals, combinations thereof, or the like.

In aspects, the surgical procedure may include an ablation, an excision, a cut, a burn, a radio frequency ablation, a cryoablation, a radiosurgical procedure, delivery of energy, an ultrasonic ablation, an abrasion, a biopsy, delivery of a substance, or a combination thereof.

In aspects, a stimulation and/or ablation electrode in accordance with the present disclosure may be configured so as to convey a pulsatile and/or radio frequency signal to the anatomical site or a site coupled thereto from the control unit, the microsurgical tool configured to convey one or more feedback signals related to the pulsatile and/or radio frequency signals back to the control unit.

In aspects, one or more of the feedback signals may be related to an electrode impedance, a bioimpedance, a local electrical field, an electrophysiological response to the pulsatile and/or radio frequency signal, combinations thereof, or the like.

In aspects, the control unit may be configured to use one or more of the electrophysiological signals to locate the anatomical site with respect to one or more components of the microsurgical tool, to use one or more of the electrophysiological signals to exclude the anatomical site from a surgical procedure, or the like.

According to aspects there is provided, a method for evaluating sympathetic tone of a subject including, inserting a microsurgical tool in accordance with the present disclosure into the subject within the vicinity of a target organ or vessel via a lumen, deploying one or more probes into the wall of the lumen, recording the electrophysiological signals conveyed by one or more of the probes included in the microsurgical tool; and generating a metric relating to sympathetic tone from the recorded signals.

In aspects, a method in accordance with the present disclosure may include monitoring another physiological parameter remotely from the target organ or vessel to generate a corrective signal and using the corrective signal to remove movement artifacts from the electrophysiological signals.

In aspects, the method may include stimulating one or more anatomical sites in the subject during the recording, and/or diagnosing a medical condition based at least in part upon the metric.

According to aspects there is provided, a method for monitoring and/or altering electrophysiological activity in the vicinity of a vessel, including penetrating an electrode into and/or through a wall of the vessel from within; and recording one or more electrophysiological signals from the activity in the vicinity of the electrode.

In aspects, a method in accordance with the present disclosure may include recording one or more of an evoked potential, remote stimulation of nervous activity, an electromyographic signal [EMG], a mechanomyographic signal [MMG], a local field potential, an electroacoustic event, vasodialation, vessel wall stiffness, muscle sympathetic nerve activity [MSNA], central sympathetic drive, tissue tone, nerve traffic, or combinations thereof in the vicinity of the electrode.

In aspects, the method may include electrically isolating the electrode from the lumen of the vessel, steering the trajectory of the electrode during the step of penetration (in aspects, the steering may be dependent upon the recording), depth of the penetration into the wall of the lumen is dependent upon the recording, recording electrophysiological activity from a plurality of electrodes, cancelling one or more movement artifacts from the recordings, delivering a substance to the vicinity of the vessel and recording the effect of the substance on the electrophysiological activity, and/or stimulating and/or ablating a tissue in the vicinity of the vessel and recording the effect of the stimulation and/or ablation on the electrophysiological activity.

In aspects, the method may include recording a first electrophysiological activity level, applying energy and/or a substance within the vicinity of the vessel and/or through the vessel wall, then recording a second electrophysiological activity level, and comparing the first and second activity levels to determine if the energy and/or substance application had a significant effect on activity, or if further energy and/or substance should be applied.

In aspects, the method may include determining if sufficient energy has been applied to the treatment site based on the comparison, evaluating the first activity level to determine a suitable treatment site in the vicinity of the organ or vessel, mapping electrophysiological activity in the vicinity of the organ or vessel using the first activity level, applying a stimulus in the vicinity of the organ or vessel, and/or recording electrophysiological activity before, during, and/or after the stimulus.

In aspects, the method may include recording electrophysiological activity in a proximal region and a distal region measured along the length of the organ or vessel as spaced with respect to an energy and/or substance delivery site, to determine if the energy application affected the electrophysiological activity in the vicinity of the delivery site, determining if the energy application was sufficient to form a neural block using the comparison, and/or applying sufficient energy to the treatment site to form a temporary block and assessing if the change in electrophysiological activity is desirable, if so, applying sufficient energy to the treatment site so as to form a substantially irreversible block. In aspects, the energy is in the form of a radio frequency current, an ultrasonic wave, or thermal energy.

In aspects, one or more of steps of a method in accordance with the present disclosure may be performed using a microsurgical tool in accordance with the present disclosure.

According to aspects there is provided, a method for determining a state of a neurological connection along a neurological pathway between one or more regions in a body including, applying a pacing signal to the wall of a vessel or to tissues surrounding the vessel in the vicinity of the neurological pathway, via an electrode plunged through the wall of the vessel from within; monitoring one or more of water concentration, tone, blood oxygen saturation of local tissues, evoked potential, stimulation/sensing of nervous activity, electromyography, temperature, blood pressure, vasodialation, vessel wall stiffness, muscle sympathetic nerve activity [MSNA], central sympathetic, tissue tone, blood flow, a blood flow differential signal, blood perfusion, a blood analyte level, nerve traffic, or combinations thereof, at one or more sites within the body to generate one or more physiological signals; and evaluating the influence of the pacing signal on the physiological signals and determining the state of neurological connection therefrom.

In aspects, the method may include applying energy in the vicinity of the vessel via one or more electrodes so as to induce a neurological block along the neurological pathway, pacing and/or monitoring before and after induction of the neurological block, comparing the physiological signals obtained before the neurological block to those obtained during the neurological block to determine the influence of the neurological block there upon, determining if the neurological block is favorable in terms of treating an underlying disease state in the body, delivering a substance in the vicinity of the vessel to induce a substantially permanent neurological block if the block is deemed favorable, and/or applying energy in the vicinity of the vessel so as to induce a substantially permanent neurological block along the neurological pathway.

In aspects, the method may include monitoring electrophysiological activity at a plurality of sites in the vicinity of the vessel via electrodes plunged through the wall of the vessel from within, in regions proximal and distal to the pacing site and/or to the site of a suspected or known neurological block, extracting an afferent signal from activity in the distal region and an efferent signal from activity in the proximal region, comparing activity measured in the proximal region and the distal region to determine if the energy application affected the electrophysiological activity in the vicinity of the target region.

According to aspects there is provided, use of a method in accordance with the present disclosure for evaluating the effectiveness of a neuromodulation procedure within a body.

According to aspects there is provided, a method for treating a neural body positioned in close proximity to a vessel including, accessing one or more regions of the neural body by threading a device through a precapillary arteriole coupling the neural body to the vessel; and applying energy and/or a substance to the one or more of the regions of the neural body via the device.

In aspects, the method may include monitoring one or more of water concentration, tissue tone, evoked potential, remotely stimulated nervous activity, sympathetic nervous activity, an electromyographic signal [EMG], a mechanomyographic signal [MMG], a local field potential, an electroacoustic event, vasodialation, vessel wall stiffness, muscle sympathetic nerve activity [MSNA], central sympathetic drive, nerve traffic, or combinations thereof with the device.

In aspects, the monitoring may be used to determine the bolus of energy and/or substance application. In aspects, the step of threading and/or termination of the threading may be dependent upon the monitoring.

According to aspects there is provided an infusion set or sheath introducer for measuring electrophysiological activity within the vicinity of a lumen including: a cannula including a lumen through which a fluid and/or a surgical tool may be passed, including a distal tip and a control end, the distal tip thereof shaped and dimensioned so as to fit within the lumen, the cannula shaped and dimensioned so as to extend from an entry site on the body into the lumen; and one or more probes configured with a tip, the probes deploy-ably coupled with the distal tip of the cannula, electrically, mechanically, and/or fluidly coupled to the control end of the elongate member, the tip of the probe shaped so as to penetrate into and/or through a wall of the lumen upon deployment from the cannula, one or more of the probes including one or more electrodes, electrically coupled to the probe, one or more of the electrodes configured to convey a signal associated with the electrophysiological activity upon deployment.

In aspects, one or more of the electrophysiological signals may be related to and/or correspond to one or more of water concentration, tone, evoked potential, remote stimulation of nervous activity, an electromyographic signal [EMG], a mechanomyographic signal [MMG], a local field potential, an electroacoustic event, vasodialation, vessel wall stiffness, muscle sympathetic nerve activity (MSNA), central sympathetic drive, tissue tone, nerve traffic, or combinations thereof.

In aspects, the probe may include an anchor for securing it to the wall of the lumen upon deployment, and the cannula may be configured for post deployment removal from the lumen, leaving the probe in place.

In aspects, a system in accordance with the present disclosure may include an elongate member with a proximal end and a distal tip, at least a portion of which may be configured for placement within the lumen of a body, the elongate member including one or more conduits each conduit providing a channel for connecting a more distal aspect of the elongate member to a more proximal aspect thereof. The elongate member may include and/or interface with one or more probes, at least a region of one or more of the probes slide-ably coupled to the elongate member and arranged so as to advance from the elongate member in a direction therefrom (e.g. radially, circumferentially, axially, combinations thereof, or the like) during a deployment or a retraction procedure. At least one probe may include an electrode, a needle, a fluid delivery aspect, combinations thereof, or the like.

In aspects, one or more probes may be arranged so as to pass through one or more of the conduits. In aspects, one or more of the probes and/or conduits may be coupled to a fluid source at a proximal end thereof and configured to provide a fluid there through to a distal tip thereof, to one or more tissue sites in the vicinity of the distal tip, etc.

In aspects, a probe and/or elongate member may include one or more microelectrodes for monitoring local electrophysiological activity, one or more of the microelectrodes may have an area of less than 1 $mm^2$, less than 0.1 $mm^2$, less than 100 $um^2$, or the like. In aspects, a probe and/or elongate member may include a stimulating and/or ablating electrode for stimulating and/or treating a local tissue site in the vicinity thereof. In aspects, one or more of the stimulating and/or ablating electrodes may have an area of more than 0.25 $mm^2$, more than 1 $mm^2$, more than 2.5 $mm^2$, more than 50 $mm^2$, or the like.

In aspects, one or more of the probes may include a plurality of electrodes (e.g. microelectrodes, stimulating electrodes, and/or ablating electrodes) each in accordance with the present disclosure.

In aspects, a system in accordance with the present disclosure may include a controller coupled to or including a connector to interconnect with the elongate member (or a mating connector coupled thereto). The controller may be configured to send/receive signals to/from one or more of the electrodes and/or to deliver one or more fluids to one or more aspects of the elongate member.

In aspects, the system may include a plurality of probes (e.g. 3 or more, 5 or more, 8 or more, etc.), arranged around the circumference of an elongate member in accordance with the present disclosure, and optionally along the length thereof (i.e. advancing along the length of the elongate member from one or more regions along the length thereof, a first region near the distal tip of the elongate member and a second region within 30 mm, within 20 mm, within 10 mm of the first region). In aspects, the probes may be arranged and/or include stops along the length thereof, such that deployment thereof outwardly from the elongate member will result in orientation of the elongate member within the lumen (i.e. substantially stabilizing the elongate member within the lumen during deployment as one or more aspects of the probes, distal tips, stops, etc. bias against the lumen wall).

In aspects, the elongate member may include 1 or more deployment regions, each deployment region including 3 or more probes equally spaced around the circumference thereof (e.g. 3 probes 120 deg, 4 probes 90 deg, etc.). Such a configuration may be advantageous to maintain the orientation of the elongate member during a deployment process of the probes into an adjacent lumen wall.

In aspects, a system in accordance with the present disclosure, a corresponding elongate member, probe, and/or one or more components thereof may be configured, shaped, and dimensioned for placement into a lumen (e.g. an artery, a vein, an arteriole, a venule, a duct, a chamber, a pocket, a tubule, a bowel, or the like), and/or an organ (e.g. a kidney, a pancreas, a spleen, a prostate, a liver, a lung, or the like). In aspects the distal tip of the component, elongate member, and/or probe may be sized so as to pass along the lumen into the parenchyma of the organ. In aspects, the distal tip of the component, elongate member, and/or probe may include a diameter of less than 2 mm, less than 1 mm, less than 0.6 mm, less than 0.3 mm, or the like.

According to aspects, there is provided use of a system, method, and/or device in accordance with the present disclosure for diagnosis and/or treatment of an abnormal neurological state associated with, augmentation of a neural circuit coupled with, altering of neural traffic to/from a tumor site coupled with, tissues, neural circuits, and/or receptors within the vicinity of the lumen and/or the organ.

In aspects, a system in accordance with the present disclosure may include an elongate member and one or more probes (e.g. shanks, needles, microneedles, microneedle electrodes, microneedle fluid delivery catheters, anchors, multi-electrode arms, stabilization arms, combinations thereof, or the like) each in accordance with the present disclosure. One or more of the probes may be coupled to the elongate member. In aspects, at least one probe may be configured so as to slide-ably advance from the elongate member into the wall of a lumen adjacent thereto. In aspects, the probe may include a distal tip shaped with a point so as to allow for ease of penetration into the wall of the lumen during advancement there through. The probe may be configured to interface with one or more target tissues in the wall, and/or with a volume of tissue exterior to the wall (e.g. via one or more electrodes, an optical sensor, etc.).

In aspects, one or more components of a system in accordance with the present disclosure, may be configured so as to be placed within a lumen (e.g. a vessel, an artery, a vein, a chamber, an aneurysm, etc.), for monitoring of one or more electrophysiological signals within and/or adjacent to the wall of the lumen. In aspects, the system may be configured to monitor muscular sympathetic nerve activity (MSNA) in a wall of a lumen, an artery, a vein, a nerve plexus, etc. In aspects, the system may be configured to monitor, stimulate, block, and/or deaden nerve traffic along a nerve and/or nerve plexus (e.g. part of a the sympathetic nervous system, autonomic nervous system, parasympathetic nervous system, celiac plexus, a renal nerve plexus, a carotid plexus, an enteric plexus, a vagus nerve plexus, pancreatic plexus, a nerve fiber terminating within the pancreas, and the like), near to a nerve ganglion (e.g. a celiac ganglion, a mesenteric ganglion, lumbosacral plexus, sphenopalatine ganglion, etc.), within a nerve ganglion, near to a receptor, amongst collections thereof, and the like. Such a configuration may be advantageous to monitor electrophysiological activity of a subject as part of a patient selection process (e.g. as part of a patient selection process for an implant, as part of a device function, a pre-surgical procedure, a denervation procedure, etc.), during a stress test, during a surgical procedure (e.g. so as to assess changes in electrophysiological activity associated with one or more aspects of the surgical procedure), as follow-up to a surgical procedure (e.g. as an assessment of the completeness of the surgical procedure, of the durability of the surgical procedure, so as to schedule for a follow-on surgical procedure, etc.).

In aspects, the system may be placed for chronic monitoring of electrophysiological activity in the wall of the lumen. Such a configuration may be advantageous for monitoring trends in electrophysiological activity (e.g. parasympathetic activity, sympathetic activity, nerve traffic, MSNA, etc.) over a prolonged period of time (e.g. minutes, hours, days, weeks, etc.). Such a configuration maybe advantageous for inferring a stress state of a subject, for contribution to a system for managing the stress state of a subject, for feedback into a neuro-activity modulation system, or the like.

According to another aspect there is provided use of a system in accordance with the present disclosure to monitor and/or alter the sensitivity of an organ in a body to a stimulus, to alter neural communication between an organ and a neural circuit, and/or to treat a cancerous tumor. A non-limiting list of organs include a gall bladder, a kidney, a small intestine, a stomach, a large intestine, a spleen, a pancreas, a bladder, an adrenal gland, a prostate, a lung, a uterus, or the like. In aspects, such alteration may be achieved through a substantially controlled/monitored ablation of one or more regions of the organ, one or more sensory nerves, receptors associated therewith, or the like.

According aspects there is provided use of a system in accordance with the present disclosure to alter a function within the body. Some non-limiting examples of functions which may be altered by the system include a sensation (e.g. a hunger sensation, an urge to urinate, etc.), a tremor, altering release/secretion of a chemical substance (e.g. acid, hormones, toxins, bile, enzymes, surfactants, sebum, renin, etc. from a secretory cell), altering smooth muscle tone, or the like. Such a system may be used to treat a disease of the gall bladder, renal system, metabolic functions, gastrointestinal function, to augment hunger sensation, reduce tone, combinations thereof, and the like.

According to aspects there is provided, a method for treating a target tissue within a subject including, accessing the target tissue with a system in accordance with the present disclosure, monitoring one or more electrophysiological signals in the target tissue to establish one or more characteristics thereof, applying a therapy to the target tissue, and monitoring the electrophysiological signals to assess if there was a change in one or more of the characteristics.

The method may include testing the response of target tissue to a stimulus to determine if the target tissue is that which is intended for treatment, if not, adjusting the placement of one or more probes and repeating the test.

According to aspects there is provided, a method for treating a target tissue within a subject with a system in accordance with the present disclosure including inserting an elongate member in accordance with the present disclosure into a lumen adjacent to the target tissue, advancing one or more probes towards the target tissue, and treating the target tissue with one or more of the probes.

In aspects, a method in accordance with the present disclosure may include placing one or more electrodes onto the body of the subject.

In aspects, a method in accordance with the present disclosure may include applying a radiofrequency current between one or more probes, and/or a probe and one or more electrodes to treat at least a portion of the target tissue.

In aspects, a method in accordance with the present disclosure may include administering a chemical agent to at least a portion of the target tissue.

According to aspects there is provided, use of a system in accordance with the present disclosure for automatically locating target tissues and/or electrophysiologically rich regions within a body. In aspects, such a system may include one or more elongate members and probes each in accordance with the present disclosure. One or more probes may be configured to monitor electrophysiological activity at one or more sites thereupon (e.g. at one or more electrodes). The system may include a processor coupled with one or more of the probes configured to triangulate signals received from the sites and to determine the location of an electrophysiologically rich region nearest to one or more probes. The system may include a graphical user interface for conveying a guidance signal (e.g. a guidance signal generated from the collection of signals, from a history of collected signals, etc.) to a user. The system may include one or more control circuits configured to actuate (e.g. translate, rotate, re-orient, etc.) one or more of the probes in response to a user direction (i.e. based on a graphical user interface output determined by the processor), and/or via a robotic control system.

In aspects, a guidance signal may be an overlay of a target zone, electrophysiological activity, etc. onto a surgical image (e.g. a zone of interest overlaid onto a CT image, MRI, fMRI, etc.).

According to aspects there is provided, use of a system in accordance with the present disclosure for monitoring one or more tissue regions in a body while applying a stimulus to one or more sites within the body (e.g. electrical stimulation, a neurotransmitter, neuroblocker, stimulant, a state of hypoxia, a state of hypercapnia, administration of NO, a local change in blood pressure, a blockage of blood flow, etc.). Such a system may be advantageous for assessing the responsiveness and/or sensitivity of one or more tissue regions to the stimulus.

In aspects, the system may be configured to treat one or more of the tissue regions or regions neurologically coupled thereto, to subsequently apply the stimulus and assess a change in the response thereto.

BRIEF DESCRIPTION OF THE DRAWINGS

Several aspects of the disclosure can be better understood with reference to the following drawings. In the drawings, like reference numerals designate corresponding parts throughout the several views.

FIGS. 1a-c show aspects of a surgical tool in accordance with the present disclosure.

FIGS. 2a-b show aspects of an elongate member in accordance with the present disclosure.

FIGS. 3a-d show aspects of a surgical tool in accordance with the present disclosure positioned within a lumen in a body.

FIGS. 4a-h show aspects of probes in accordance with the present disclosure.

FIGS. 10a-e show aspects of steerable probes in accordance with the present disclosure.

FIGS. 11a-b show aspects of a surgical tool in accordance with the present disclosure placed in a lumen during treatment of a neural body.

FIG. 12 shows aspects of an elongate member with an embedded circuit in accordance with the present disclosure.

FIGS. 13a-b show schematics of an embedded circuit in accordance with the present disclosure.

FIGS. 14a-b show aspects of a surgical tool with multiple probes in accordance with the present disclosure and an example of signals obtained therefrom during a surgical procedure.

FIGS. 15a-b show aspects of probes in accordance with the present disclosure.

FIGS. 23a-e show schematics of aspects of controllers and control circuits in accordance with the present disclosure.

FIGS. 24a-b show aspects of methods for treating target tissues in accordance with the present disclosure.

DETAILED DESCRIPTION

Figure 5A:
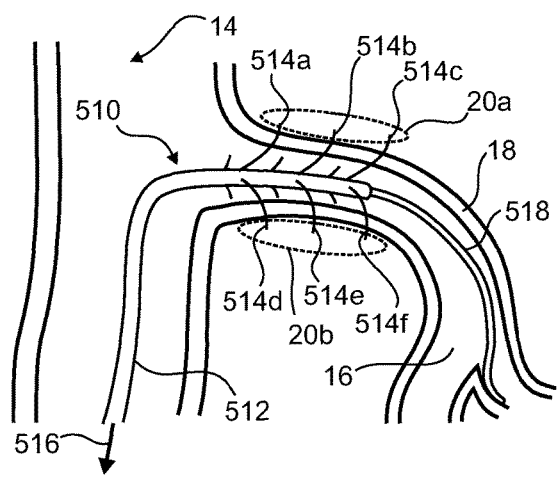
FIGS. 5a-b show aspects of a surgical tool and a temporal plot of monitored signals for performing a surgical procedure in accordance with the present disclosure.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A surgical procedure may include partial or complete block of a neural signal, and/or receptor function, augmentation of the function of a receptor, transmission of a neural signal, a partial and/or substantial neurectomy, peripheral neurectomy, sympathectomy, parasympathectomy, or the like.

In aspects, one or more systems in accordance with the present disclosure may be coupled with one or more imaging modalities including computer assisted imaging computed tomography (CT), magnetic resonance imaging (MRI), positron emission tomography (PET), magnetoencephalography (MEG), functional MRI, stereotactic surgery, or the like before, during, and/or after a surgical procedure. Such imaging modalities may be used to provide visualization of a target tissue, of advancement of one or more aspects of the system towards the target tissue, confirmation of placement of one or more aspects with respect to the target tissue or surgical site, etc. Use of such imaging modalities may be performed prior to/after surgery, and/or intraoperatively.

In aspects, one or more probes in accordance with the present disclosure may include a fiber optic coupled to a light source and/or a laser (e.g. fiber optic guided radiation to a target tissue), a cryotherapy unit, a heat circulation unit (i.e. a unit for heated wire thermal therapy), an ultrasonic generator, or the like for treatment and/or monitoring of target tissue. For purposes of discussion, the majority of non-limiting examples discussed herein are directed to electrical interfacing with tissues and chemical delivery aspects of such therapies.

A system and/or surgical tool in accordance with the present disclosure may include an elongate member with a proximal end and a distal tip, at least a portion of which may be configured for placement within the lumen of a body, the elongate member including one or more conduits each conduit providing a channel for connecting a more distal aspect of the elongate member to a more proximal aspect thereof. The elongate member may include and/or interface with one or more probes, at least a region of one or more of the probes slide-ably coupled to the elongate member so as to advance from the elongate member in a direction towards an associated lumen wall (e.g. radially, circumferentially, axially, combinations thereof, or the like). At least one probe may include an electrode, a needle, a fluid delivery aspect, combinations thereof, or the like.

In aspects, one or more probes may be arranged so as to pass through one or more of the conduits. In aspects, one or more of the probes and/or conduits may be coupled to a fluid source at a proximal end thereof and configured to provide a fluid there through to a distal tip thereof, to one or more tissue sites in the vicinity of the distal tip, etc.

In aspects, a probe and/or elongate member may include one or more microelectrodes for monitoring local electrophysiological activity, one or more of the microelectrodes may have an area of less than 1 $mm^2$, less than 0.1 $mm^2$, less than 100 $um^2$, or the like. In aspects, a probe and/or elongate member may include a stimulating and/or ablating electrode for stimulating and/or treating a local tissue site in the vicinity thereof. In aspects, one or more of the stimulating and/or ablating electrodes may have an area of more than 0.25 $mm^2$, more than 1 $mm^2$, more than 2.5 $mm^2$, more than 50 $mm^2$, or the like.

In aspects, one or more of the probes may include a plurality of electrodes (e.g. microelectrodes, stimulating electrodes, and/or ablating electrodes) each in accordance with the present disclosure.

In aspects, a system in accordance with the present disclosure may include a controller coupled to or including a connector to interconnect with the elongate member (or a mating connector coupled thereto). The controller may be configured to send/receive signals to/from one or more of the electrodes and/or to deliver one or more fluids to one or more aspects of the elongate member.

A system in accordance with the present disclosure may be configured such that at least a portion thereof may be placed into a lumen (e.g. an artery, a vein, an arteriole, a venule, a duct, a chamber, a pocket, a tubule, a bowel, or the like), and/or an organ (e.g. a kidney, a pancreas, a liver, a lung, a carotid body, a spleen, a gallbladder, or the like) configured for monitoring, stimulating, and/or treating tissues in the vicinity thereof.

In aspects, the system/surgical tool may include an elongate member and one or more probes (e.g. shanks, needles, microneedles, microneedle electrodes, microneedle fluid delivery catheters, anchors, multi-electrode arms, stabilization arms, combinations thereof, or the like) each in accordance with the present disclosure. One or more of the probes may be coupled to the elongate member. In aspects, at least one probe may be configured so as to slide-ably advance from the elongate member into the wall of a lumen adjacent thereto. The probe may be configured to interface with one or more target tissues in the wall, and/or with a volume of tissue exterior to the wall.

In aspects, one or more probes may be shaped and dimensioned so as to slide ably pass through at least a portion of one or more of the conduits during advancement towards a lumen wall as part of a placement procedure.

In aspects, the system may include a plurality of probes, the probes oriented so as to protrude from the elongate member during actuation (e.g. automatic, semi-automatic, manual, etc.). One or more of the probes may be configured so as to be advance-ably placed into a lumen wall adjacent thereto (i.e. the probe may include a pointed distal tip, a needle electrode, or the like). One or more probes may be configured to communicate (e.g. fluid communicate, electrically communicate, optically communicate) with the target tissues, a coupled controller, and/or between two or more probes.

In aspects, one or more probes may be arranged so as to be advanced, retracted, twisted, and/or actively bent (e.g. such as via movement of an active material based probe, a micro-wire actuated probe, etc.) either manually by an operator, or via a robotic actuation (e.g. a mechanism, a servo-controlled mechanism, etc.). Such a configuration may be advantageous for assisting with placement of a probe during a procedure, with aligning a probe with a region of target tissue, advancing the probe through a target tissue, precisely placing one or more regions of the probe within a target tissue, etc. In aspects, one or more probes may be coupled to one or more actuation mechanisms (e.g. a rotary actuator, linear actuator, etc.) coupled to the proximal end of the elongate member such that rotary actuation results in reorientation of the distal tip of the probe, linear actuation results in advancement/retraction of the distal tip of the probe, etc. In aspects, the probe may include an actuate-able feature (e.g. a biphasic actuator, a bending actuator, a torsional actuator, etc.) configured to provide reorientation, rotation, and/or translation of the distal tip of the probe during use.

In aspects, one or more probes may include a microneedle electrode, configured such that at least a portion thereof (e.g. a tip, a shank, a region, a plurality of regions, etc.) may be configured so as to facilitate electrical communication with one or more target tissues adjacent thereto, one or more probes, and/or one or more external electrodes. In aspects, the probe may include a needle like distal tip, the distal most portion of which may be electrically exposed, while the remainder may be insulated so as to provide a microneedle electrode for monitoring, stimulating, and/or ablating a local tissue site, perhaps in combination with delivery of a chemical substance through a conduit and/or lumen of the probe, elongate member, etc.

In aspects, a probe may include an array of electrodes, perhaps sized, arranged, and configured so as to assist with determination of a local field gradient, configured so as to monitor a plurality of sites along the length of the probe, to provide a configurable electrode arrangement for sensing, stimulation, ablation, etc.

In aspects, one or more electrodes may be arranged with an active area (i.e. area available to electrically interface with adjacent tissues) of less than 10 $mm^2$, less than 1 $mm^2$, less than 0.1 $mm^2$, less than 10,000 $um^2$, less than 1,000 $um^2$, less than 100 $um^2$, etc. Alternatively, one or more electrodes may be configured so as to form electrical impedance in normal saline of greater than 100 ohm, greater than 1 kohm, greater than 100 kokm, greater than 1 Mohm, greater than 10 Mohm, greater than 50 Mohm, etc. Such electrodes may be advantageous for monitoring electrophysiological activity from heterogeneously distributed neurological features in an adjacent tissue site (i.e. a site into which the electrodes have been placed, within a body).

In aspects, one or more probes may be configured with a characteristic width (i.e. a dimension perpendicular to a length measurement thereof, for example, a diameter), or less than 1 mm, less than 200 um, less than 100 um, less than 50 um, less than 12 um, etc. Such characteristic width may vary along the length of the probe. In aspects, one or more probes may be tapered to a fine tip (e.g. a tip with less than 5 um radius of curvature, less than 1 um radius of curvature, etc.) so as to more easily be advanced through tissues during a procedure.

In aspects, one or more regions of a probe in accordance with the present disclosure may be coated with a substance and/or treated so as to be lubricious in the presence of water. Some non-limiting examples of such coatings include a hydrophilic coating, a silicone coating, a PTFE coating, parylene, a ceramic, PEBAX, a hydrogel, etc. Some non-limiting examples of such treatments include vapor deposition of a ceramic, a polymer, an ion treatment process, an electroplating process, dip process, etc.

In aspects, the probe may include a tip fashioned with a tip electrode (i.e. an exposed region of the probe suitable for electrically interfacing with a surrounding tissue, with one or more probes, an external electrode, etc.). In aspects, the tip electrode may be arranged so as to provide a microscopic interface over a length at an end of the probe less than 150 um, less than 50 um, less than 20 um, less than 10 um, less than 1 um, and the like. Such a configuration may be suitable for spatially precise monitoring of local field potentials during a procedure (e.g. during monitoring of electrophysiological activity, during a denervation procedure, during placement of the probe, etc.). In aspects, the tip electrode may be arranged so as to provide an intermediately sized interface along the length of the probe, greater than 50 um but less than 1 mm, greater than 100 um but less than 500 um, or the like. Such an arrangement may be suitable for stimulating local tissues, for monitoring overall electrophysiological activity around a volume of tissue, to act as a reference electrode, and the like. In aspects, the tip electrode may be configured along a length of the probe greater than 100 um, greater than 500 um, greater than 1 mm, greater than 2 mm, and the like. Such an arrangement may be advantageous for providing a sufficiently high current to surrounding tissues in the vicinity of the electrode, for example, during a hyperpolarizing stimulation, during an ablation procedure, so as to substantially affect tissues in the vicinity of the tip electrode, and the like.

In aspects an electrode in accordance with the present disclosure may be formed from an electrically and/or ionically conductive material. Some non-limiting examples of electrode materials include gold, platinum, platinum iridium, stainless steel, tungsten, iridium, palladium, rhodium, organic conducting polymer modified materials, poly (acetylene)s, poly(pyrrole)s, poly(thiophene)s, poly(terthiophene)s, poly(aniline)s, poly(fluorine)s, poly(3-alkythiophene)s, polytetrathiafulvalenes, polynapthalenes, poly(p-phenylene sulfide), poly(para-phenylenevinylene)s, poly(3,4-ethylenedioxy thiophene) (PEDOT), poly(3,4-ethylenedioxythiophe)/poly(styrenesulfonate)(PEDOT/PSS), polyfuran, polyindole, polycarbazole, nanorods, nanotubules, carbon, carbon nanotubes, combinations thereof, hybridized composites thereof, and the like.

In aspects, an electrode in accordance with the present disclosure may include a PEDOT film hybridized with gold nanoparticles (e.g. gold particles with diameter less than 20 nm, less than 15 nm, etc.). In aspects, one or more electrodes may include a nanomaterial filler or functionalized material for enhancing one or more properties thereof (e.g. active area, conductivity, etc.).

In aspects, an electrode including an organic conducting polymer or a functionalized organic conducting polymer (e.g. via grafting of specie to the backbone thereof, grafting of an organometallic, biomolecule, etc. thereto, and the like) may be configured so as to monitor a local event associated with tissues in the vicinity of the electrode during use. In such a configuration, the electrical conductivity of the organic conducting polymer in contact with the surrounding tissues may change by orders of magnitude in response to pH, local potential changes, concentration of an analyte (e.g. a neurotransmitter, a neuroblocker, an enzyme, a protein, oxygen, etc.) during use. Such changes may be advantageously monitored during a surgical procedure, so as to assess placement of the probe, determine progress of an associated treatment, etc.

In aspects, one or more probes may include a fluid delivery channel for delivery of a fluid (e.g. a medication, a stimulant, a neuroblocker, a sclerosing alcohol, a neurotransmitter, a chemical denervation agent, a neurodisruptive agent, a sclerosing agent, phenol, alcohol, guanethidine, etc.) for delivery to the target tissues. In aspects, one or more probes may include a microchannel for delivery of fluid, the microchannel having a diameter at one or more positions along the length thereof of less than 250 um, less than 150 um, less than 20 um, etc. In an aspect associated with a method for treating a target tissue in accordance with the present disclosure, the system may be configured to deliver a bolus of a denervation agent to the target tissues. In aspects, the fluid may be delivered as part of a surgical procedure (e.g. nerve stimulation, denervation, chemical neurolysis, chemical neurolytic blockade, cryoablation, etc.). In aspects, during a method in accordance with the present disclosure a first bolus of neural blocking agent may be delivered to the target tissues, the local electrophysiological response may be monitored by one or more electrodes in accordance with the present disclosure, depending on the monitoring, a denervating agent may be delivered to the target tissues (i.e. so as to render the procedure permanent).

In aspects, a system in accordance with the present disclosure may include means for delivering a medicament (e.g. channels, a reservoir, a fluid delivery needle, etc.), and/or include one or more quantities of a mixture of lidocaine (1%, 2%, >5%, etc.) with epinephrine (1:1,000, 000, 1:100,000, 1:10,000, etc.), and dehydrated ethyl alcohol (2%, 3%, 4%, 5%, 25%, 50%, >50%, etc.) and/or phenol (1%, 2%, 5%, 10%, >10%, etc.) dilute solution for treatment of a volume of target tissues. Additionally, alternatively, or in combination, an amount of bupivacaine (0.1%, 0.25%, 0.5%, >0.5%, etc.), optionally epinephrine (1:200,000) combined with the dehydrated ethyl alcohol and/or phenol may be provided for treatment of a volume of target tissues. Alternatively, additionally, or in combination, the local anesthetic may be administered sequentially prior to injection of the neuro-blocking solution.

In aspects, a fast acting and/or fast clearing neuroblocking agent may be injected to reversibly assess a change in local function, to assess if one or more probes are placed in the vicinity of the target tissues, etc.

In aspects, the system may include one or more electrical circuits (e.g. sensing circuits, stimulating circuits, treatment circuits, combinations thereof, etc.) coupled to one or more of the probes. One or more of the circuits may be configured to deliver a current to one or more of the probes, between two or more probes, between one or more probes and an electrode (e.g. a patch electrode, an electrode placed elsewhere in/on the body, etc.). Alternatively, additionally, or in combination one or more of the circuits may be configured to sense an electrical signal at or between one or more probes, control interconnection of one or more probes and another probe, and/or an electrode, monitor impedance and/or electrochemical impedance spectroscopy, between one or more probes and another probe, and/or an electrode, etc. Impedance changes during a procedure may be used to determine when the procedure is near completion, target temperature levels, as a safety indicator, to determine if the probes are suitably placed against tissues, etc.

In aspects, one or more treatment/combination circuits may be configured to deliver a treatment signal (e.g. a radiofrequency signal, a microwave signal, modulated current, delivery of energy, etc.) to/between one or more probes for purposes of ablating the target tissue located in the vicinity thereof. In aspects, one or more of the probes and/or the characteristics of the radiofrequency signal may be configured so as to ablate the target tissue in a substantially predetermined pattern (e.g. a patch-like pattern, patterned array of treatment zones, targeted treatment zones, an elliptical pattern, a longitudinal pattern, a shell-like pattern, a toroidal pattern, etc.). In aspects, the predetermined pattern may be oriented with respect to the wall of the lumen, one or more adjacent anatomical features (e.g. an organ, a tubule, a marker, etc.). In aspects, the ablation pattern may be determined based upon prior sensing of electrophysiological signals from tissues in the vicinity thereof.

In aspects, a marker in accordance with the present disclosure may include a pretreated tissue, an ablated tissue, a protein marker, a fluorescent marker, a previously placed body (e.g. a placed contrast agent, a placed contrast particle, fluorescent marker, etc.). The marker may be placed as part of a diagnostic test, a preoperative inspection, a surgical procedure, an imaging test, a transplant, etc. Such a configuration may be advantageous for follow-up procedures, returning to the site of a surgical procedure, etc.

In aspects, one or more stimulating circuits may be configured to deliver one or more stimulation signals (e.g. a current pulse, a voltage pulse, a neuro-transmitting agent, a neuro-blocking agent, etc.) to one or more probes for purposes of stimulating one or more aspects of the target tissue (i.e. one or more nerve fibers included in the target tissue and/or adjacent thereto). In the case of delivery of an agent, the stimulating circuit may be coupled to an associated fluid delivery pump, manifold, etc. Such stimulation may be used to communicate with one or more organs within a body, to determine the state of a surgical procedure (e.g. to determine the state of a denervation procedure, or the like), to determine the present state of a target tissue (e.g. to determine the health of a target tissue, to determine a change in electrophysiological activity associated with a target tissue, to determine a change in conductivity, density, stiffness, etc. associated with a target tissue, etc.), to treat a disease state in the body (e.g. to modulate sympathetic tone, to interrupt neurological traffic within the vicinity of the target tissues, to modulate an overly active response within an organ, etc.).

In aspects, one or more sensory circuits may be configured to monitor one or more aspects of one or more probes during a procedure (e.g. during a surgical procedure, a monitoring procedure, etc.). In aspects, one or more sensory circuits may be configured to monitor a current, voltage, impedance, impedance spectrograph (i.e. spectral region of a property, etc.), temperature, etc. between one or more of regions of a probe, between two or more of the probes (i.e. between regions of one or more probes, etc.), between a probe and an external electrode (e.g. an externally placed electrode, a reference electrode, an electrode coupled to the elongate member, an electrode placed onto the body, etc.).

In aspects, the sensory circuits may be used to determine if one or more aspects of a probe have entered into the vicinity of a target tissue (e.g. near to a nerve, a nerve bundle, a muscle, into a region of adipose tissue, penetrated through fascia, penetrated a second lumen, etc.).

In aspects, one or more of the sensory circuits may be configured so as to monitor one or more probes in combination with one or more of the treatment and/or stimulation circuits, which may act upon one or more of the probes. In aspects, one or more of the sensory circuits may be configured so as to monitor a surgical process, perhaps at least partially completed by one or more of the treatment and/or stimulation circuits. In aspects, a sensory circuit in accordance with the present disclosure may be coupled to two or more probes within the system. A first probe may be configured with a reference electrode in accordance with the present disclosure, while one or more of the other probes may be configured with one or more sensing electrodes. The circuit may be configured to obtain one or more differential signals between the reference electrode and one or more sensing electrodes in the system. Such a configuration may be advantageous for mapping, locating target tissues, and/or monitoring electrophysiological activity during a procedure, predicting changes in electrophysiological activity associated with a pending procedure, measuring changes in electrophysiological activity associated with a partial/completed procedure, and the like.

In aspects, one or more sensory circuits may be configured to monitor temporary activity block caused by hyperpolarizing current application, delivery of a temporary neural blocking substance, and/or thermally significant current applied to one or more electrodes associated with the system. Such a configuration may be advantageous to determine proper placement of an electrode prior to application of an ablation current, administration of a chemical agent, etc.

In aspects, one or more of the sensory circuits may be configured so as to monitor one or more applications of a fluid (via one or more of the probes) to at least a region of a target tissue. Such an example may be preferable for monitoring the extent of penetration of the fluid into the target tissue, etc. monitoring the interaction of the fluid and the target tissue (e.g. monitoring the state of a denervation process, degree of impedance change in the vicinity of the injection, etc.).

In aspects, one or more of the sensory circuits may be configured so as to monitor the distribution of a fluid into the target tissues. Such a configuration may be advantageous for optimizing the bolus of fluid administered to the target tissues. In aspects, one or more of the sensory circuits may be configured to monitor impedance between two or more adjacent electrodes during a procedure (e.g. a surgical procedure, administration of a bolus of fluid to the target tissue, etc.). Such a configuration may be advantageous to determine and/or control the quantity of a fluid delivered to the target tissues, progression of a surgical procedure (e.g. an ablation procedure, a neural block, etc.), determine the spatial extent of the procedure (i.e. how far from the delivery site the chemical has affected neural function/structure, etc.), or the like.

In aspects, one or more of the stimulation and/or treatment circuits may be configured so as interact with a fluid bolus administered to the target tissues (i.e. by controlling the passage of current there through for example). Such a configuration may be advantageous to further control current flow between one or more probes during a surgical procedure (e.g. during an ablation procedure).

In aspects, one or more of the stimulation and/or treatment circuits may be configured to apply a current pulse and/or a radiofrequency signal between two or more probes, and/or one or more probes and an external electrode (e.g. a patch electrode, an electrode placed elsewhere in the body, etc.).

In aspects, one or more of the circuits may be configured to administer a current pulse and/or radiofrequency signal to one or more regions of the target tissue for a period of 250 seconds, 100 seconds, 10 seconds, 1 second, less than 1 second, etc. In aspects, the current pulse and/or radiofrequency signal may be administered with sufficiently high current, so as to heat one or more regions of the target tissue to a predetermined value within the designated time period. Due to the placement of the probes into the target tissue, a rapid heating pulse may be administered to effectively heat the target tissues to a therapeutic level (e.g. a temperature above 40 C, above 50 C, above 60 C, above 70 C, etc.). Such heating may be applied with a duty cycle, such that the mean temperature rise in the vicinity of the electrode may be approximately 40 C, 50 C, 60 C, etc. while the transient temperatures and electric fields experienced by adjacent tissues may vary with modulation thereof. In aspects, one or more probes may include a temperature sensor positioned and configured to monitor local temperature rise during a procedure, in combination with electrophysiological monitoring functions, etc.

In aspects, one or more circuits may be configured to administer one or more stimulatory pulses to the surrounding tissue during use. Such stimulatory pulses may be configured with amplitude, pulse width, repetition rates, etc. at significant values so as to generate a response in the target tissues without causing substantial damage thereto.

Radiofrequency current may be applied with a frequency of greater than 50 kHz, greater than 500 kHz, greater than 1 MHz, greater than 300 MHz (i.e. into the microwave spectrum), etc. Radiofrequency signals may be modulated with a predetermined and/or variable duty cycle, managed by a user, by an automatic control algorithm, etc.

In aspects, one or more of the circuits may be configured to administer a pulse (e.g. a current controlled pulse, a voltage controlled pulse, a trailing edge pulse, etc.) to one or more regions of the target tissue. In aspects, the circuits may be configured to administer a hyperpolarizing pulse to one or more regions of the target tissue. Such a pulse may be advantageous for suppressing neuronal activity from one or more nerves in the vicinity of the target tissue. Such a configuration may be advantageous for reducing pain associated with the surgical procedure, for determining if an associated probe is located within the target tissue, etc. In aspects, a method for augmenting neural traffic may include applying a first hyperpolarizing pulse to a target anatomical site, providing a sustained stimulating pulse to the site or a corresponding surgical site, and determining, based upon a pain response from the subject, if the target anatomical site, and surgical site are coupled together, if the hyperpolarizing pulse has effectively blocked neural traffic from the surgical site to a previously coupled neural circuit within the body, etc.

In aspects, one or more of the circuits may be configured to administer a hyperpolarizing pulse to one or more probes and sequentially administer a stimulating pulse to one or more of the probes. Such a combination of pulse delivery may be advantageous for suppressing action potentials in a first subset of nerves located in the vicinity of the target tissue, while initiating one or more action potentials in a second subset of nerves located in the vicinity of the target tissue.

In aspects, one or more sensory circuits may be configured to monitor one or more electrophysiological signals (e.g. an extracellular potential, an evoked potential, electromyographic signal, electrocardiographic signal, combinations thereof, or the like), from one or more regions of one or more probes as positioned in the vicinity of the target tissue. In aspects, such a configuration may be advantageous for monitoring MSNA in a lumen wall of a vessel in a body, monitor a stimulation provided by one or more probes in the system, etc.

In aspects, one or more sensory circuits may be configured to monitor a plurality of electrophysiological signals. One or more sensory circuits, digital algorithms, signal processing algorithms, etc. may be configured to separate, compare, and/or combine one or more of the electrophysiological signals from a plurality of electrodes or signals generated therefrom. Such a configuration may be advantageous to separate a local neurological signal from a macroscopic electromyographic signal, to map one or more aspects of the target tissue (i.e. determine the location of one or more tissue types within the vicinity of the target tissue, etc.), to monitor progression of a stimulus and/or physiological signal between probe sites in the target tissue, to assess the extent of a surgical procedure, etc.

In aspects, one or more components of a system in accordance with the present disclosure, may be configured so as to be placed within a lumen (e.g. a vessel, an artery, a vein, a chamber, an aneurysm, etc.), for monitoring of one or more electrophysiological signals at a site within and/or adjacent to the wall of the lumen. In aspects, the system may be configured to monitor muscular sympathetic nerve activity (MSNA) in a wall of a lumen, an artery, a vein, a nerve plexus, etc. Related activity may be monitored in the vicinity of one or more sensory afferents and/or motor efferents. Thus a correlation between associated nerve traffic may be related to the firing rate of sensory afferents directly from stimulation of receptors, whether in muscles, tendons, or skin. The same is true for efferent signals to smooth muscle located within a lumen wall.

In aspects, the system may be configured to monitor nerve traffic along a nerve and/or nerve plexus (e.g. part of a the sympathetic nervous system, autonomic nervous system, parasympathetic nervous system, celiac plexus, a renal nerve plexus, a carotid plexus, an enteric plexus, a vagus nerve plexus, pancreatic plexus, a nerve fiber terminating within the pancreas, and the like), near to a nerve ganglion (e.g. a celiac ganglion, a mesenteric ganglion, lumbosacral plexus, sphenopalatine ganglion, etc.), within a nerve ganglion, near to a receptor, within the parenchyma of an organ, amongst collections thereof, and the like. Such a configuration may be advantageous to monitor electrophysiological activity of a subject as part of a patient selection process (e.g. as part of a patient selection process for an implant, as part of a device function, a pre-surgical procedure, a denervation procedure, etc.), during a surgical procedure (i.e. so as to assess changes in electrophysiological activity associated with one or more aspects of the surgical procedure), as follow-up to a surgical procedure (i.e. as an assessment of the completeness of the surgical procedure, of the durability of the surgical procedure, so as to schedule for a follow-on surgical procedure, etc.).

In aspects, the system may be placed for chronic monitoring of electrophysiological activity in the wall of the lumen. Such a configuration may be advantageous for monitoring trends in electrophysiological activity (e.g. parasympathetic activity, sympathetic activity, nerve traffic, MSNA, related afferent/efferent traffic, etc.). Such a configuration maybe advantageous in systems for inferring the stress state of a subject, for contribution to a system for managing the stress state of a subject, for feedback into a neuro-activity modulation system, etc., or the like.

In aspects, one or more probes may be oriented into an arch, an anchor, a spiral, etc. so as to provide an interlocking action with the wall of the lumen. Such a configuration may be advantageous for anchoring and/or orienting one or more aspects of one or more probes to the wall of the lumen. Such anchoring may be advantageous for retaining one or more aspects of the system during a procedure, during monitoring, etc. Such anchoring may be advantageous for aligning one or more aspects of the system to a target tissue, a surgical site, a lumen wall, one or more probes, etc. during a treatment, during a chronic monitoring session, etc.

In aspects, a system in accordance with the present disclosure may be configured and used to alter the sensitivity of one or more regions of an organ in a body to a stimulus. A non-limiting list of organs for which such a procedure may be conceived include a gall bladder, a kidney, a small intestine, a stomach, a large intestine, a spleen, a pancreas, a bladder, an adrenal gland, a prostate, a lung, a uterus, or the like. In aspects, such alteration may be achieved through substantially controlled ablation of one or more regions of the organ, one or more sensory nerves, coupled neural pathways, receptors associated therewith, or the like with a system in accordance with the present disclosure.

In aspects, a system in accordance with the present disclosure may be used to alter a function within the body. Some non-limiting examples of functions which may be altered by the system include a sensation (e.g. a hunger sensation, an urge to urinate, etc.), a tremor, altering release/secretion of a chemical substance (e.g. acid, hormones, toxins, bile, enzymes, surfactants, sebum, renin, etc. from a secretory cell), altering of a microenvironment, altering perineural invasion of a tumor into surrounding tissues, altering delivery of nutrients to a target tissue, or the like. Such a system may be used to treat a disease of the gall bladder, gastrointestinal system, to augment hunger sensation, reduce sympathetic tone (i.e. overall, and/or related to one or more sympathetic branches, etc.), treat hypertension, affect hyperplasia within an organ, reduce inflammation in an organ, combinations thereof, and the like.

In aspects, one or more components/aspects of a system and/or an elongate member in accordance with the present disclosure may be configured so as to slide over a guidewire with a diameter of less than 2 mm, less than 1 mm, less than 0.5 mm, less than 0.2 mm, less than 0.1 mm, etc. Such a configuration may be advantageous for accessing anatomy within a body via a minimally invasive procedure, assessing miniature vessels within the parenchyma of an organ, etc.

In aspects, the system may include one or more guard electrodes, coupled to the elongate member or a secondary member, coupled with one or more circuits so as to direct a current thereby/through. One or more circuits may be configured so as to communicate/control an electrical signal between one or more of the guard electrodes and one or more of the probes. Such communication may be advantageous for controlling an electric field generated thereby, to control current flow through one or more probes and one or more guard electrodes, to minimize current flow through tissues adjacent to the guard electrodes, etc.

In aspects, the system may include one or more stabilizing members (e.g. a balloon, an anchor, a curved leg, etc.) coupled to the elongate member, configured to brace and/or position one or more regions of the elongate member near to or against the wall of a lumen during use. One or more of the stabilizing members may be configured so as to be deployable during use (i.e. so as to move from a first, stored position, to a second deployed position upon actuation).

In aspects, one or more of the probes may include a stabilizing element, in order to assist with orienting the elongate member, and/or control the depth of penetration of one or more of the probes into the lumen wall upon deployment. In aspects, the stabilizing element may be a step change in diameter of a probe, a change in surface roughness of a probe, an electrode region configured to assess the presence of fluid thereby, or the like.

In aspects, one or more stabilizing member may include a balloon, the balloon configured so as to take on a deployed shape when actuated (i.e. when a fluid bolus is delivered into the balloon), and the deployed shape being suitable for retaining the balloon within a lumen. The balloon may be configured to brace and/or orient at least a region of the elongate member with respect to the wall of a lumen during a procedure. In aspects, the balloon may be shaped so as to allow for fluid passage thereby even when it is deployed. Some non-limiting shapes (i.e. cross sections oriented along a plane substantially perpendicular to the elongate member) of balloons include a rectangular shape, a ring, a toroid, a gear-like, a flower-like shape, a quatrefoil, an oval, an ellipse, a crescent, a star, a blunted star, a hypocycloid, a hypotrochoid, a rose, a cardiod, a vane, a ribbon, combinations thereof, and the like.

In aspects, one or more of the stabilizing members may include a flexible member, coupled to the elongate member, optionally deployable therefrom during use (i.e. via use of a retractable sheath, by an actuation mechanism in accordance with the present disclosure, etc.). Some non-limiting examples of flexible members include coils, hooks, clips, leaf spring elements, mesh, netting, bistable forms, cantilever beams, and the like. The flexible member may be maintained in close proximity to the elongate member in a stored position (e.g. retractably stored within the elongate member, stored between the elongate member and a sheath, etc.) and configured so as to bias away from the elongate member (i.e. during a deployment procedure) during use (e.g. through actuation of the flexible member, push actuation of the flexible member, retraction of an associated sheath, sliding of the flexible member along the length of the elongate member, etc.).

In aspects, one or more of the stabilizing members may include one or more electrodes, arranged, shaped and dimensioned to interface with the lumen wall upon deployment therein, the electrodes coupled to a circuit in accordance with the present disclosure. Such electrodes may be used for sensing/ablating/stimulating procedures, or the like in accordance with the present disclosure.

In aspects, one or more stabilizing members and/or probes may include an active material element, the active material element coupled with a circuit and/or a controller in accordance with the present disclosure. Control signals delivered to the active material element may help to bias the stabilizing members and/or probes towards the lumen wall, towards the target tissues, actively control the bias force between the stabilizing member and a lumen wall, etc. Some non-limiting examples of active materials that may be suitable for application to one or more probes and/or stabilizing members include shape memory materials (e.g. shape memory alloys, polymers, combination thereof), electroactive polymers (e.g. conjugated polymers, polypyrrole, dielectric elastomers, piezoelectric polymers, electrets, liquid crystals, graft elastomers, polyvinylidene fluoride, combinations thereof, derivatives thereof, etc.), piezoceramics (e.g. amorphous piezoceramics, single crystals, composites, etc.). In addition the active material may be used as a vibratory exciter and/or mechanical probe, for use in monitoring the tone of the adjacent tissues. Alternatively, in addition or in combination, such active materials may be used to cause vibratory/ultrasonic ablation and/or local heating to the tissues during a procedure. In aspects, one or more stabilizing members and/or probes may be configured so as to actuate (e.g. in this case, to change shape, alter a bias force, etc.) so as to bias and/or orient one or more aspects of the system against a wall of an associated lumen (i.e. a lumen into which the at least a portion of the system is deployed during a surgery) and/or reorient the component with respect to the target tissue.

In aspects, one or more stabilizing members may be actuate-able so as to cling to the wall of an associated lumen during use. In aspects, the stabilizing member may be configured so as to close the tip thereof in a pinch-like configuration, as a pincer like configuration, etc. so as to fasten to the wall of an associated lumen during use. In one non-limiting example, a stabilizing member may include a shape memory alloy (e.g. a Nitinol® material) configured so as to undergo shape change when placed inside the body of a subject (i.e. transition between a first shape and a second shape upon increase in temperature due to placement within a warm body). In aspects, a stabilizing member including a shape memory alloy may be configured to change shape (e.g. curl, twist, bend, etc.) upon heating with a control current (i.e. as provide by one or more circuits coupled thereto). Such a configuration may be advantageous for controllably fastening one or more aspects of a system in accordance with the present disclosure to a wall of an associated lumen.

In aspects, one or more probes may include an active material configured so as to assist with orientation during passage into/through the wall of a lumen during surgery. Such a configuration may be advantageous for guiding a probe through the wall of a lumen, towards a target tissue. Additionally, alternatively, or in combination one or more of the probes may include a radiopaque (i.e. radiodense) material (e.g. a titanium, tungsten, zirconium oxide, metal filled polymers, barium sulfate, bismuth compounds, platinum, gold, palladium, combinations thereof, and the like). Such a configuration may be advantageous for visualizing one or more aspects of a probe (e.g. shape, orientation, position with respect to a target tissue, etc.) during a procedure within a body.

In aspects, a system in accordance with the present disclosure may include a plurality of probes, the probes configured so as to protrude at least somewhat radially from an associated elongate member, such that one or more of the probes may penetrate into the wall of an adjacent lumen during use. The system may include one or more circuits configured to interface with one or more of the probes, such that a current (e.g. a radiofrequency current, a modulated current, a microwave current, etc.) may be passed between two or more probes and/or between one or more probes and an additional electrode (e.g. an electrode placed elsewhere on/in the body). Such a configuration may be advantageous for treating regions of target tissue in the vicinity of the lumen. In aspects, current may be passed through two or more probes so as to treat and/or stimulate target tissues along the length of the lumen (i.e. in a direction substantially longitudinal to the lumen), along a path substantially circumferential to the lumen (i.e. in a path arching around the center of the lumen), radially out from the lumen (i.e. in a path directed substantially outwardly from the center of the lumen), combinations thereof, or the like. A longitudinal treatment may be advantageous for treating a collection of target tissues (e.g. nerve fibers, smooth muscle fibers, receptors, etc.) along the length of a lumen, so as to controllably limit the rate of re-innervation and extent of nerve regrowth after the procedure.

In aspects, one or more circuits and/or processors included in a system in accordance with the present disclosure may be coupled to a sensory electrode and may be configured to assess functionality of one or more regions of target tissue in the vicinity of the sensory electrode before, during, and/or after a treatment. The circuits and/or processors may be configured to monitor nerve activity in the vicinity of the sensory electrode and to extract or distinguish between changes in such activity before, during, and/or after a process (e.g. by comparison of signals, of an activity metric derived therefrom, etc.). In aspects, the circuits and/or processors may be configured to extract one or more metrics of signal activity from the monitored signals, some non-limiting examples of such activity include spectral power density thereof, spike count rates, integrated signal strength, and the like. Such metrics may be used to determine the effect of a procedure on the local electrophysiological activity in the vicinity of the sensory electrode, to control a surgical procedure (i.e. to control the extent of a denervation process), to predict the outcome of a procedure, and the like.

In aspects, one or more probes may be moved (e.g. retracted, nudged, rotated, etc.) during a procedure (e.g. during an ablation procedure). Such movement may be used to controllably increase the region of treatment during a procedure.

In aspects, a method for treating a target tissue within a subject in accordance with the present disclosure may include accessing the target tissue with a system in accordance with the present disclosure, monitoring one or more electrophysiological signals in the target tissue to establish one or more characteristics thereof (e.g. activity level, pulse amplitudes, pulse rates, pulse/stress correlation, relationship between pulse timing, amplitude, etc. and another physiological process in the body), applying a therapy to the target tissue, and monitoring the electrophysiological signals to assess if there was a change in one or more of the characteristics.

The method may include testing the response of target tissue to a stimulus to determine if the target tissue is that which is intended for treatment, if not, adjusting the placement of one or more probes and repeating the test.

In aspects, a method for treating a target tissue within a subject with a system in accordance with the present disclosure may include inserting an elongate member in accordance with the present disclosure into a lumen adjacent to the target tissue, advancing one or more probes towards the target tissue, and treating the target tissue with one or more of the probes. The method may include penetrating the lumen wall with one or more of the probes.

In aspects, the method may include placing one or more electrodes onto the body of the subject.

In aspects, the method may include applying a radiofrequency current between one or more probes, and/or a probe and one or more electrodes to treat at least a portion of the target tissue.

In aspects, the method may include advancing a guidewire into the lumen.

In aspects, the method may include altering the shape of the one or more of the probes.

In aspects, the method may include monitoring neurological activity of tissues in the vicinity of at least a portion of one or more probes. In aspects, the method may include guiding a probe towards the target tissue using the monitored neurological activity.

In aspects, the method may include monitoring tissue in the vicinity of an electrode coupled to at least one probe to determine the activity thereof.

In aspects, the method may include administering a fluid bolus to one or more regions of the target tissue. In aspects, the method may include monitoring neurological activity in the vicinity of one or more electrodes to determine a change in the signal, and/or signal activity after administration of the bolus.

In aspects, the method may include tracking the position of one or more aspects of a probe with an imaging system such as an MRI, fMRI, CT scanner, with an ultrasonic probe, or the like.

In aspects, the method may include robotically steering one or more of the probes to access the target tissue.

In aspects, the method may include ablating at least a region of the target tissue. In aspects, the method may include monitoring a change in neurological activity after at least a portion of the ablation procedure.

In aspects, the method may include placement of a probe substantially near to a receptor within the target tissue (e.g. within 2 mm, within 1 mm, within 100 um, within 20 um, etc.).

In aspects, the method may include passing a therapeutic current longitudinally along the length of the lumen, radially out from the lumen, and/or circumferentially around the wall of the lumen. Such therapeutic current may be passed between one or more probes in accordance with the present disclosure, between one or more probes and a remotely applied electrode, between one or more probes and one or more electrodes located on an elongate member, and/or on a stabilizing member each in accordance with the present disclosure.

In aspects, a system in accordance with the present disclosure may include a probe with a bent and/or twisted tip. Such a probe may be suitable for steerable guidance through a tissue, so as to controllably advance the probe towards the target tissue. The system may include one or more controls (e.g. manual controls, levers, knobs, mechanized/servo controls, actuators, motors, etc.) coupled to the probe so as to enable advancement, retraction, and/or rotation thereof during a procedure in accordance with the present disclosure.

In aspects, one or more probes may be bendable, so as to flexibly access one or more regions of the target tissue, progress down a tortuous pathway, etc. during a procedure.

In aspects, a system in accordance with the present disclosure may be used to automatically locate a target tissue and/or electrophysiologically rich region within a body. The system may include one or more elongate members and probes in accordance with the present disclosure. One or more probes may be configured to monitor electrophysiological activity at one or more sites thereupon (e.g. at one or more electrodes). The system may include a processor configured to triangulate signals received from the sites and to determine the location of an electrophysiologically rich region nearest to one or more probes or electrodes there upon. The system may include a graphical user interface for conveying a guidance signal (i.e. a guidance signal generated from the collection of signals, from a history of collected signals, etc.) or image to a user. The system may include one or more control circuits configured to actuate one or more probes in response to a user direction (i.e. based on a graphical user interface output determined by the processor), and/or via a robotic control system.

Some non-limiting examples of a guidance signal include an overlay of a target zone, electrophysiological activity, etc. onto a surgical image (e.g. a zone of interest overlaid onto a CT image, MRI, fMRI, etc.).

In aspects, a system in accordance with the present disclosure may be configured for monitoring one or more tissue regions in a body while applying a stimulus to one or more sites within the body (e.g. a neurostimulating current, a neurotransmitter, neuroblocker, stimulant, a state of hypoxia, a state of hypercapnia, administration of nitric oxide <NO>, a local change in blood pressure, a blockage of blood flow, etc.). Such a system may be advantageous for assessing the responsiveness and/or sensitivity of one or more tissue regions to the stimulus.

The system may be configured to treat one or more of the tissue regions, to subsequently apply the stimulus and assess a change in the response thereto.

In aspects, the system may include a plurality of probes in accordance with the present disclosure, three or more probes, more than 5 probes, more than 9 probes, more than 12 probes, etc. In aspects, the system may include a plurality of electrodes in accordance with the present disclosure, more than 2 electrodes, more than 8 electrodes, more than 25 electrodes, more than 100 electrodes, etc. In aspects, a probe in accordance with the present disclosure may include one or more of the electrodes.

In aspects, the system may include a plurality of probes (e.g. 3 or more, 5 or more, 8 or more, etc.), arranged along the circumference of the elongate member as well as along the length thereof (i.e. advancing along the length of the elongate member and towards the lumen wall from one or more regions along the length thereof, a first region near the distal tip of the elongate member and a second region within 30 mm, within 20 mm, within 10 mm of the first region). In aspects, the probes may be arranged such that deployment thereof outwardly from the elongate member will result in orientation of the elongate member within the lumen (i.e. substantially stabilizing the elongate member within the lumen during deployment). In aspects, the elongate member may include 1 or more deployment regions, each deployment region including 3 or more probes equally spaced around the circumference thereof (e.g. 3 probes 120 deg, 4 probes 90 deg, etc.). Such a configuration may be advantageous to maintain the orientation of the elongate member during a deployment process of the probes into an adjacent lumen wall.

A system/surgical tool in accordance with the present disclosure may be used to access and to treat one or more sensory receptors: Ampullae of Lorenzini (respond to electric field, salinity, temperature, etc.), baroreceptors, chemoreceptors, hydroreceptors, mechanoreceptors, nociceptors, osmoreceptors (osmolarity sensing), photoreceptors, proprioceptors, thermoreceptors, combinations thereof, and the like.

In aspects, a surgical tool in accordance with the present disclosure may include the capability to sense one or more physiological parameters at one or more points around a surgical site, as well as include the capability to stimulate and/or ablate tissues at one or more of the same points and/or an alternative point around a surgical site. The nerve ablation system may be configured so as to access vessels and/or surgical sites in the body. The non-limiting examples disclosed herein may be directed towards such configurations (e.g. so as to controllably ablate renal nerves along a renal artery via an endoscopic procedure, a minimally invasive procedure, a percutaneous procedure, etc.).

In aspects, one or more electrodes in accordance with the present disclosure may be configured to apply/receive a radio frequency (RF) or microwave (MW) current to/from the surrounding tissue. The RF current may be provided locally between two of more electrodes, or alternatively between one or more electrodes and a macroelectrode placed elsewhere on the body (e.g. on a large skin patch over the surgical site, an electrode placed on another organ, as selected from multiple patches placed over the body, in an associated catheter electrode, etc.). In aspects, where the current may be restricted to being applied between electrodes, the path for current flow may be well controlled, yet may be highly localized. Alternatively, in an example where RF current may be passed between one or more electrodes and one or more macroelectrodes, the current flow may be more challenging to control, but may be used to access tissues more remote from the probes, electrodes, etc. (e.g. to reach farther into the adjacent tissues, deeper into a region of target tissue, etc.).

In aspects, a system in accordance with the present disclosure may include one or more circuits to simultaneously engage one or more electrodes with the flow of RF current during an ablation process. In aspects, the local impedance measured between electrodes may be monitored and/or controlled so as to better optimize the current delivered thereto. Additionally, alternatively, or in combination, the local current flow through each electrode may be monitored so as to determine the path of the RF current flow, to ensure no leakage currents are detected, etc. Such information may be used to better control the delivery of RF currents to the target tissues during an ablation procedure.

In aspects, an externally placed (e.g. onto the body of the subject) light source (e.g. infrared, near infrared, visible, etc.) may be directed into the body towards the surgical site, target tissues, and/or lumen. The light source may optionally be modulated to provide a more easily detected signal within the subject. One or more probes may be equipped with optical microsensors may sense light emitted from the light source. The mapping of received light may be used to located anatomical features such as nerves near to one or more of the optical microsensor equipped probes during a procedure.

In aspects, one or more externally placed light sources may be used to help locate the anatomical sites of interest during the procedure. An external light source may include a narrow band light source, a broad band light source, light sources spaced apart from each other, and/or combinations thereof. The light sources may be modulated so as to be more easily detectable by sensors located in or near to the anatomy of interest (e.g. lumen, target tissue, etc.). In aspects, a plurality of light sources may be aimed at the surgical site from distinct vantage points within the body (i.e. as accessed via an endoscopic procedure, etc.) or externally to the body (i.e. as positioned at locations on the body).

Such optical configurations may be advantageous for mapping the local tissues before, during and/or after a surgical procedure. They may also be advantageous for implementation into a nerve detection system (e.g. as input to a nerve hunting algorithm, etc.).

One or more probes may include an electrical shield such that the probe tips may be effectively shielded from other currents flowing through an associated surgical tool (such as a catheter), the body, etc. during a procedure.

One or more probes, and/or elongate members may include a circuit such as a bi-directional switching network, micro amplifier array, a multiplexer, an analog/digital filter, and analog/digital converter, etc. in order to amplify sensed signals as close as possible to the anatomical interface, as well as to switch the function of an electrode, a probe tip, group of electrodes, etc. between sensory, stimulatory, and/or ablation functions, etc.

In aspects, a bidirectional switching network may be used to enable multi-functional stimulation/sense capabilities in one or more probes, etc. The switching network may be included in a local amplifier array, included in a flexible circuit on one or more probes, attached along the surgical tool (i.e. along an elongate member), as part of the electrical routing along a probe, etc. or alternatively as an extracorporeal element included in a surgical system in accordance with the present disclosure.

A micro amplifier array may be used to preamplify the signals obtained from one or more sensory aspects of the probes and/or probe electrodes, so as to improve the noise signature, etc. during use.

In aspects, one or more probes may be sufficiently hyper elastic (e.g. formed from a memory alloy material, a super-elastic material, pseudo elastic, etc.) so as to effectively deploy from a very small deployment tube and expand outward to larger tissue areas over which to monitor/treat. Such a configuration may be advantageous in so far as a small number of unit sizes may be suitable for treating a wide range of anatomical structures. In addition, the designed curvature and form of a probe may be substantially chosen so as to further enable a wide deployable range of movement during a procedure.

One or more aspects of a probe may be formed from a polymer, a thermoplastic, polyurethane, a silicone, an elastomer, silk fibroin materials, combinations thereof, or the like. Inclusion of microporous or fibrous substrates, may be advantageous to allow one or more regions of the probe to adhere to the adjacent tissues via capillary effects (i.e. tendencies to wick fluid from adjacent tissues into the substrate). The thickness of films formed from the material may be less than 30 um thick, less than 20 um, less than 10 um, less than 4 um, less than 1 um. Composites of somewhat stiffer materials (such as polyimide, PET, PEN, etc.) and somewhat softer materials (e.g. silicones, polyurethanes, thermoplastic elastomers, etc.) maybe used to compromise between overall structural stiffness and conformal capabilities.

Patterned overcoats and/or composite layers may also be used to expose electrode materials and/or probe tips to the surrounding tissues in the vicinity of measurement regions, etc.

In aspects, one or more components of a probe may be formed from a silk material (e.g. *Bombyx mori* cocoons). The material may be processed to remove sericin (which may cause undesirable immunological response) using methods known in the art. The resulting material can be solvent cast into shapes and crystallized to form self-supporting structures or insulation along a probe, a structural support for a probe, solvent coated onto the probe, etc.

Alternatively, additionally or in combination the ascribed sensing techniques may be combined with stimulation from local sources. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (i.e. in aspects the successive stimulation and sensing may be used to determine the degree of neurological block and/or neuromuscular block there between). Such functionality as well as directionality of the nerve signal propagation (e.g. efferent, afferent, etc.) may be more easily determined through use of combined local stimulation and sensing.

Several patterns of nerve stimulation may be used to determine the function of the local nerve structures as well as any associated degree of neurological block and/or neuromuscular block that may be caused by the surgical procedure (e.g. ablation, overstimulation, blocking stimulation, etc.), anesthesia, abrasion, etc.

In aspects, a single stimulation pulse may be applied to one or more electrodes to cause a response in an associated nerve at frequencies of less than 10 Hz, less than 1 Hz, less than 0.1 Hz. The downstream response as measured by any of the described techniques may depend on the frequency with which the stimuli are applied. In order to allow for complete recovery of the nerve between stimulations (i.e. between pulse trains), a frequency of less than or equal to 0.1 Hz may be advantageous.

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e. perhaps a suitable metric for determining how a procedure has affected that nerve).

Note that the sensing of the nervous response may not need to be local to a surgical site and/or target tissues, but in aspects, may be oriented downstream (in the sense of the flow of an associated nervous signal) from the site or in aspects may be a systemic response to the stimulation.

A surgical system in accordance with the present disclosure may include one or more elements to monitor physiological activity and/or analyte levels (e.g. a hormone level, an ion concentration, etc.), in and/or near to one or more portions of a ganglion, a gland, an endocrine gland (e.g. an adrenal gland, an adrenal medulla, etc.), etc. Such physiological activity may be monitored before, during, and/or after an ablation procedure to determine the extent of the procedure or the effect of the procedure there upon.

In aspects, a multi tool surgical system may be employed, each surgical tool in accordance with the present disclosure. In aspects, a first tool may be used to probe and/or ablate tissues at a first surgical site (e.g. an artery, a renal artery, a left renal artery, etc.) while one or more secondary tools may be configured to monitor one or more physiological parameters elsewhere in the body (e.g. in an alternative artery, a vein, in an organ, at a lymph node, at a ganglion, etc.), perhaps to determine the effect of the surgical procedure there upon. In aspects, the tools may be inserted into the same or closely positioned entry points into the body (e.g. a surgical port, etc.). Such a configuration may be advantageous for providing a minimally invasive surgical system to perform the surgical procedure (e.g. a sympathectomy, a renal sympathectomy, etc.) with monitoring performed at multiple, remote locations within the body.

Some further aspects relating to systems and methods for adjusting (temporarily and/or permanently) nerve function, while substantially minimizing collateral damage to adjacent structures via minimally invasive catheter systems, and methods are now discussed. References made to ablation may be considered to refer to a general surgical procedure (to cut, heat, cool, excise, etc.) on a tissue.

A method for determining the functionality, directionality, location of and/or the extent of nerve function degradation before, during and/or after a surgical procedure may include stimulating a range of nerves located at a proximal and/or distal location on an organ (e.g. coupled with a kidney, coupled to a renal artery, coupled with a gland, etc.) in a body; monitoring an evoked response at a location distal and/or proximal to the location of the stimulation; evaluating the signal quality, spectral content, etc. related to the evoked response and/or changes in the evoked response during and/or after the surgical procedure.

In aspects, a method in accordance with the present disclosure may include stimulating the stimulation location (e.g. a nerve) with one or more pulse trains, the pulse trains including one or more pulses with a predetermined spectral content (e.g. pulses centered around 10 Hz, 50 Hz, 100 Hz, 500 Hz, etc.) at one or more locations proximal and/or distal to the surgical site.

The pulse train may be applied locally to the nervous structure, with an amplitude of generally 1.5× the voltage required to obtain a maximal amplitude compound action potential (CAP), with pulse duration of generally between 0.05 and 0.5 ms and interval of between 2 ms (for 500 Hz spacing) to 100 ms (for 10 Hz spacing). The pulse train may include one or several such pulses, perhaps even spaced with alternative timing over the application of the pulse (so as to better scan through a frequency range of interest). The corresponding nervous response may be monitored at another location on the vessel or in the body. Such response may be monitored with a gain of generally 500 to 5000 and generally over a frequency band of 0.1 Hz to 10 kHz. This configuration may be used to evaluate the overall health and/or capability of the nervous structure connecting the stimulating location and the monitoring location.

During a surgical procedure, early indication of functional alteration to the nerve structure may be determined by monitoring for a change in the properties of the sensed signal (e.g. a change in latency, amplitude, conduction velocity, spectral content, etc.). In aspects, an ablation pulse may be applied to the nerve between the stimulatory and monitoring locations. A change in the properties of the sensed signal (e.g. a decrease in high frequency content therefrom, a change in latency, change in amplitude, etc.) may be an early indicator that the pulse is being applied properly to the nervous structure there between. In addition, more pulses can be applied and the response monitored in order to observe the nerve response through to a sufficient state of functional alteration, such as during an ablation procedure.

Monitoring may continue during a follow up period immediately after the surgical procedure, and/or during a longer term period (e.g. hours, days, weeks, etc.). Such follow up may be used to determine and/or prognosticate on the longevity of the surgical intervention.

In aspects, the technique may be used to identify the particular neurons of interest ensure that the correct neurons are being treated surgically (as well as to ensure that the extent of the treatment is acceptable). Such identification may involve monitoring a level of neurological activity on the sensed nerve(s) to determine if the levels are outside of the norm (i.e. as compared with other sites in the body, an activity metric for the patient population or a subset thereof, etc.).

A method for generating a follow up schedule following a surgical procedure may involve monitoring the neurological activity of the site for a period of time (e.g. hours, days, weeks, etc.), at periodic follow up times (e.g. 1 week, 1 month, 6 months, 12 months, etc.) after the surgical procedure; trending the neurological activity to create a metric relating to changes therein over the period of time; and predicting recurrence data (e.g. probability of recurrence, a timeframe of recurrence, etc.) therefrom; and generating a follow up schedule dependent upon the recurrence data.

A method for searching for a nerve of interest on the wall of a lumen may include applying a point pressure on the wall of the lumen while monitoring distal and/or proximal nervous activity (e.g. monitoring, and/or stimulation and sensing on either side of the point pressure probe). Changes in the observed signals may be indicative of pressure induced neural block due to the applied point pressure (i.e. thus identifying the location of the neural anatomy in question).

The method may include clamping the vessel or target neural structure with a flat, smooth backing plate (e.g. a flat soft surface, etc.) and a protruding probe on the adjacent wall, to increase pressure at the interface between the probe and the tissues. The probe may be combined with an ablation electrode (thus providing colocation of the pressure application and the ablation zone). Multiple probes may be used together to deliver ablation along the length of a nerve or nerve bundle. In the case of multiple probes, the probes may be relatively placed onto the surface so as to optimize an ablation current passed there between.

Relating to nerve compression syndrome, acute nerve compression studies have shown some loss of nerve function through application of acute transverse pressure above 40 mmHg, and loss of all nerve function at pressure application above 50 mmHg. Other studies have shown functional block under transverse compression when a pressure of 30 mmHg less than diastolic pressure is applied and 45 mmHg less than the mean arterial blood pressure is applied to the nerve. Thus one or more components of the system (e.g. a clamp, an electrode element, a point pressure applicator, etc.) may provide pressure variation above and/or below these ranges in order to assess nerve function, location, etc. as described herein.

The point pressure applicator may be configured to operatively provide an oscillating pressure to the test site, to synchronize pulsatile pressure application with an array of probes, etc. so as to better orient a pair or array of probes for an ablation procedure.

A surgical tool in accordance with the present disclosure may include one or more whiskers extending from a tool surface, a probe, or the like so as to reliably contact an adjacent tissue structure during a surgical procedure. The whiskers may include sensing elements such as electrodes, and the like.

Whisker penetration into an adjacent nerve bundle may be used to achieve more intimate contact thereto, as well as to better isolate electrodes from other macroscopic signal interference, etc.

Whiskers may be formed from microfibers, nanofibers, microneedles, nanoneedles, etc. In one aspect, one or more whiskers may be formed from a carbon structure (e.g. a carbon fiber, a carbon nanotube, graphene, etc.). The whiskers may be insulated along a portion of their length, with an electrically exposed region at the tip there upon.

In aspects, the system may include a feature enhancing medium, to highlight targeted tissue species (e.g. highlight nerve tissues, etc.). The medium may include molecular binding species to selectively bind with surface receptors on the intended target tissue, perhaps changing one or more visual (chromatic) properties in the process and/or including a visual marking moiety. Some non-limiting examples of suitable molecular binding species are peptides and aptamers. Suitable peptides and aptamers may be selected for target tissue (e.g. nerve tissue, fat, etc.) and may be selected as known in the art. In aspects, one or more probes may be configured with a channel for delivery of a binding specie to the target tissue (e.g. via an injection, etc.).

Inclusion of molecular binding species that have been selected for the target cells may be advantageous to assist with anatomical visualization during a surgical procedure. The molecular binding species may be provided suspended in a delivery vehicle, such that it may be conveniently delivered to the target tissues during a procedure. The delivery vehicle may be a gel material, a 1 part curing gel, elastomer, etc. that may be conveniently delivered to the target tissues. A fully curable vehicle may be advantageous for providing a simplified method for completely removing the medium from the body after the surgical procedure and/or targeting process has been completed.

Molecular binding species may include a visual marking moiety that is configured to improve visibility thereof. Thus the molecular binding species will bind to the target tissue sites (e.g. nerve tissue, etc.), and will be highlighted by the visual marking moiety for visualization with an appropriate visualization system. Some non-limiting examples of visual marking moieties include: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW or combinations thereof.

This visualization approach may be advantageous to identify the key tissues for surgical procedures (such as a sympathectomy procedure). By providing the material in a form suitable for surgical delivery and complete removal post operatively (or a safely bioresorbable material), the resulting system may be safer compared to approaches that require systemic application of the material.

One or more probes may include an optical source (e.g. a fiber optic, a micro LED, etc.), and a receiver (e.g. a fiber optic, a photo sensor, etc.) for analyzing the binding species during the procedure. Such combination of delivery of the highlighting medium towards the target tissues and subsequent visualization of the highlighting medium may be used to determine placement of the probes, asses the target tissues, etc.

The surgical system may include other functionality including: angiographic die delivery, saline delivery, temperature monitoring, intra and extra vascular coordination between devices, through wall imaging, through wall current flow, saline provision for internal arterial cooling, and the like.

FIGS. 1a-c show aspects of a surgical tool in accordance with the present disclosure. FIG. 1a shows the distal tip of a surgical tool 110 in a deployed state. The tip includes an elongate member 112 configured so as to couple an interfacing tip 118 (i.e. a tip for placement into a body) with a control end 116 (i.e. an end of the surgical tool for interfacing with a connector, controller, etc.). The surgical tool 110 includes one or more probes 114*a-f* coupled to the elongate member 112 (i.e. a member with an axis about which the member is longer than it is perpendicular thereto), configured so as to slide and/or extend out from the elongate member during a deployment procedure 124. The elongate member 112 may include one or more channels 115, conduits, recesses, tubes, lumens, or the like configured to convey at least a portion of the one or more of the probes 114*a-f* and/or a mechanism coupled thereto between the distal tip and the control end 116 of the surgical tool 110. One or more of the probes 114*a-f* may be oriented so as to pass in a direction at least partially perpendicular to the axis of the elongate member 112 during a deployment procedure 124. One or more of the probes 114*a-f* and/or the elongate member 112 may include one or more electrodes 120, 122, 126, 130*a,b*, 134 in accordance with the present disclosure. In aspects, one or more probes 114*a* may include a channel 127 for delivery of a fluid 128 to a target tissue provided from the control end 116 of the surgical tool 110. One or more of the probes 114*b* or the elongate member 112 may include a marker band 136 to assist with imaging placement of the probe 114*b* or the distal tip during a procedure.

In aspects, one or more of the probes 114*f* may include a stabilizing element 132 in accordance with the present disclosure positioned along the length thereof. The stabilizing element 132 may provide a physical transition point so as to controllably limit the depth of penetration of the probe 114*f* tip into the lumen wall upon deployment 124. In aspects, the stabilizing element 132 may be positioned less than 4 mm, less than 2 mm, less than 1 mm, or the like away from the tip of the probe 114*f*.

FIG. 1*b* shows the distal tip of a surgical tool 150 in accordance with the present disclosure in an undeployed state. In the undeployed state, the probes (not explicitly shown) are substantially refracted into the elongate member 152 such that it can be more easily deployed to an associated lumen (i.e. to an associated surgical site). A plurality of entry points 156 are shown along the wall of the elongate member 152 through which one or more probes may protrude during deployment. One or more of the probes may be arranged within one or more conduits 154 arranged along the length of the elongate member 152. The conduits 154 may span the length of the elongate member 152, coupling the distal tip thereof to the proximal end 158 (e.g. to a controller, a connector, or the like).

FIG. 1*c* shows a length of the surgical tool 170 for deployment into a lumen within a body. The surgical tool 170 is shown with corresponding probes 174 arranged in a deployed state 178. The elongate member 172 connects the distal tip 171 of the surgical tool 170 to the control end 177. The control end 177 may include one or more mechanisms for actuating one or more of the probes or a region of the elongate member, communicating a fluid to one or more of the probes, and/or communicating electrically with one or more aspects of a probe 174 and/or the elongate member 172. As shown, the controls may include a mechanism for slidingly deploying 180 one or more of the probes 174 (e.g. with a sliding mechanism, via actuation of an element of the probes 174, via retraction of a sheath, etc.), and/or rotatably deploying 182 one or more of the probes 174 (e.g. with a screw-like deployment mechanism, leading to retraction of a sheath, extension of a push rod, etc.), or the like. The control end 177 may include one or more actuators, servo controlled mechanisms, etc. for providing actuation.

A connector included in the control end 177 may be configured to provide mechanical coupling (i.e. for one or more actuation mechanisms), electrical coupling 176 (i.e. for communicating with one or more probes/electrodes), and/or a fluid coupling (i.e. for delivering and/or sampling a fluid to/from the target tissues, lumen, etc.).

In aspects, a system associated with the surgical tool 170 may include one or more macroelectrodes 186 and associated cabling 188 coupled thereto to provide communication between a controller 190 and the macroelectrodes 186 during use. In aspects, the control end 177 may be provided with a connector to couple the surgical tool 170 to a controller 191.

FIG. 2*a-b* show aspects of an elongate member 210 in accordance with the present disclosure. FIG. 2*a* shows a cross section of an elongate member 210 in accordance with the present disclosure. The elongate member 210 may include a plurality of channel lumens 215, the channel lumens 215 arranged so as to accommodate one or more probes there through. The elongate member 210 may include one or more guide lumen 220 to accommodate a guide wire in accordance with the present disclosure. In aspects, one or more of the channel lumens 215 may be formed by a microtube (e.g. a thin walled tube, a PEEK tubing, a PTFE tubing, a polyimide tubing, etc.) arranged so as to run along the length of the elongate member. In aspects, the channel and/or guide lumens maybe formed from tubes, extrusions, drilled, micro-fabricated, combinations thereof, or the like.

FIG. 2*b* shows a distal tip of an elongate member 210 in accordance with the present disclosure. Optionally, the distal tip may include a nose 225 (i.e. in this case a rounded nose) configured so as to ease entry into the lumen. The tip is shown in FIG. 2*b* with a plurality of channels 217, 219 running there through. The channels are oriented so as to run along the length of the elongate member 210, optionally curved so as to terminate along the wall of the elongate member. As shown, the trajectory of the channel may be arranged so as to alter the trajectory of a probe protruding therefrom during use. In aspects, the channels 217, 219 may be bent about an axis substantially perpendicular to the axis of the elongate member, so as to form a radially protruding probe, and/or bent about a free axis with respect to the elongate member, to form a circumferentially protruding probe. Such configurations may be balanced so as to achieve suitable probe trajectories within the bending limits of the probes themselves, and so as to minimize the necessary diameter of the elongate member 210. FIG. 2*b* shows to probe exit trajectories 221, 223 associated with corresponding channels 217, 219. A first trajectory 221 is oriented with a shallow angle with respect to the elongate member axis 227 (i.e. such that an associated probe extends substantially parallel to the elongate member 210 during deployment), while a second trajectory 223 is shown oriented with a deep angle with respect to the elongate member axis 227 (i.e. such that an associated probe extends nearly perpendicularly from the elongate member 210 during deployment).

In aspects, an elongate member 210 with diameter less than 1 mm may be fashioned with 4 channel lumens 217, 219, each with an internal diameter of approximately 125 um, configured to accommodate 4 associated probes, each with a diameter of 75 um-112 um.

In aspects, the tip of the elongate member 210 may be fashioned as an add-on to the central length of the elongate member 210, or manufactured as part of a monolithic elongate member 210 (e.g. fashioned into a single elongate member 210 tube), etc.

In aspects, the channels may be configured to protrude from the tip of the elongate member 210 (i.e. along an axis substantially in parallel with the axis of the elongate member). In such a configuration, a region of one or more probes may be bent such that the probe curves into the wall of the lumen upon deployment from the elongate member 210 during use.

FIGS. 3a-d show aspects of a distal tip of a surgical tool 310 in accordance with the present disclosure positioned within a lumen 2 in a body. FIG. 3a shows a radial cross section of the surgical tool 310 and the lumen 2 oriented so as to demonstrate deployment of one or more probes 312a-f from the elongate member 311 into the walls 4 of the lumen 2 and into/towards target tissue 6a-c. The surgical tool 310 is shown with 6 probes 312a-f, oriented with 120 deg between each prove in a plane, and two planes of probes 312a-f (i.e. a first plane of probes 312a,c,e at a first length along the elongate member 311, and a second plane of probes 312b,d,f at a second length along the elongate member 311). In this case, target tissues 6a-c are shown external to the lumen wall 4 but such tissues may be within the lumen wall, along the edge of the lumen wall, etc.

One or more of the probes 312a-f may include one or more electrodes and/or fluid delivery ports configured to interface with the adjacent tissues upon deployment 314 (i.e. to deliver/sample fluid, and/or electrically interface therewith) from the elongate member 311 thereto. In aspects, the distance into the lumen wall 4 that the probes 312a-f may be deployed 314 could be configured prior to the procedure (e.g. via design aspects, such as stabilizing elements on the probes, via adjustment of the deployment distance, etc.).

FIG. 3b demonstrates a substantially circumferential RF current 322 during a treatment (with respect to the lumen axis) being applied between tip electrodes 320a,b situated on two deployed probes 318a,b embedded into a target tissue 6d outside the wall 8 of a lumen into which the elongate member 316 has been placed. The shape, completeness, and, follow up of the treatment may be performed by one or more methods and/or systems in accordance with the present disclosure. In aspects, an RF current 324 may be passed between the tip electrodes 320a,b to provide one or more aspects of a treatment, stimulation, etc. In aspects, sensing of local electrophysiological activity may be performed with the tip electrodes 320a,b, with one or more such electrodes 320a,b providing a reference, or an electrode situated elsewhere on the device or body providing a reference electrode.

FIG. 3c demonstrates a substantially longitudinal treatment 338a,b (with respect to an associated lumen axis 334), being performed in a target tissue by electrodes situated in four probes 332a-d (in this non-limiting example). A longitudinal treatment 338a,b may be advantageous for extending the affected region along the length of one or more nerves, thus extending the time period over which regrowth of fibers will re-establish a connection between untreated ends thereof. The probes 332a-d are shown deployed from an elongate member 330 situated within a lumen 9 within a body, the probes 332a-d protruding out through the lumen wall 10 and into the adventitia surrounding the lumen wall 10. In aspects, the elongate member 330 and the probes 332a-d may be coupled to a control end 336 of the device and/or an associated controller in accordance with the present disclosure.

FIG. 3d demonstrates a substantially radial treatment 344 (with respect to the lumen axis) applied between multiple electrodes 342a,b situated on a signal probe 340 (in this non-limiting example). The radial treatment 344 may be advantageous for extending a region of treatment outward from the lumen 14 in cases where the target tissue 6e may be surrounded by sensitive tissues that are not to be treated by the surgical intervention. In aspects, the probe 340 may be coupled to an elongate member situated within the lumen 14 in accordance with the present disclosure. The probe 340 is shown extending through the lumen wall 12 after being deployed from the elongate member.

Through combination of the above examples, a surgical tool in accordance with the present disclosure, may be configured to treat complex regions of target tissue (e.g. extended regions with isolated patterns, island type patterns, helical patterns, toroidal patterns, etc.), in a substantially controlled manner so as to treat the intended tissues without damaging unintended tissues during the procedure.

The same probes (or other probes included in the system) may be configured in combination with one or more circuits in accordance with the present disclosure to monitor activity in the target tissues, before, during, and/or after treatment to assess the extent of the treatment, to controllably terminate the treatment when a suitable traffic level is observed, and the like.

FIGS. 4a-h show aspects of probes in accordance with the present disclosure. FIG. 4a shows aspects of a probe 410 with a plurality of electrodes 412a,b 414a-d in accordance with the present disclosure situated thereupon. One or more larger electrodes 412a,b may be configured so as to provide treatment currents, stimulation currents, or fashioned to act as reference electrodes, while one or more microelectrodes 414a-d may be configured to monitor activity, stimulate, and/or provide treatment currents to spatially precise regions within the target tissue.

FIG. 4b shows aspects of a probe 416 in accordance with the present disclosure fashioned with a tip electrode 420 in accordance with the present disclosure, the remainder of the probe insulated from the surroundings by an insulating layer 418. The tip of the probe may be honed, so as to allow for penetration of the probe in to tissues without causing substantial damage or requiring excessive force. In aspects, the length 422 of the tip electrode 420 may be designed for an intended purpose (e.g. sensing, stimulation, ablation, blocking, etc.). In aspects, the length 422 of the tip electrode 420 may be more than 0.5 mm, more than 1 mm, more than 0.5 mm so as to support RF ablation procedures. In aspects, the length 422 of the tip electrode 420 may be shorter than 0.25 mm, shorter than 0.1 mm, shorter than 0.01 mm, or the like so as to support stimulation and/or sensing procedures.

FIG. 4c shows aspects of a probe 424 in accordance with the present disclosure fashioned with a microscopic tip electrode 428 in accordance with the present disclosure. In aspects, the tip electrode 428 may be arranged with an exposed region extending less than 10 um along the length 430 of the probe 424. Such a configuration may be advantageous for highly precise monitoring of electrophysiological activity near the probe 424 tip during a procedure. One or more lengths of the probe 424 may be insulated 426 so as to electrically isolate those regions of the probe 424 from the surrounding electrophysiological fields.

FIG. 4d shows aspects of a probe 432 in accordance with the present disclosure including a channel 436 for delivery of a chemical agent 444 or for sampling of fluid to/from 446 a tissue during a procedure from/to 442 a controller and/or fluid reservoir each in accordance with the present disclosure. The probe 432 may include one or more electrodes 438 situated along a length 440 thereof to facilitate assistance with placement, monitoring of neurological activity, evaluation of neurological activity (e.g. before, during, after treatment, etc.), evaluate changes in neurological activity (e.g. before, during, after treatment, etc.) due to the placement/removal of fluid, or the like. In aspects, the probe 432 may include insulation 434 along one or more regions thereof so as to isolate those regions from the surrounding electrophysiological fields.

FIG. 4e shows aspects of a probe 450 in accordance with the present disclosure fashioned with an array of electrodes 454 situated at the tip thereof. The electrode array 454 may be coupled to one or more circuits to controllably alter the treatment zone/monitoring zone around the electrode, actively map neurological behavior in the vicinity of the probe and the like. One or more regions of the probe 450 may be insulated 452 so as to electrically isolate those regions from the surrounding electrophysiological fields. The probe 450 and/or associated elongate member may include an embedded circuit in accordance with the present disclosure to provide pre-amplification and/or switch functionality for one or more of the electrodes in the array 454. Such an electrode array 454 may be advantageous for selectively locating, analyzing, and treating target tissues of a previously undetermined size and location without causing significant damage to surrounding tissues.

FIG. 4f shows aspects of a probe 456 in accordance with present disclosure including linear array of electrodes 462a-e situated along the length thereof. The electrode array maybe advantageous for controlling a treatment zone to one or more target tissues in the vicinity of the probe 456. The linear electrode array 462a-e may be coupled to one or more circuits to controllably alter the treatment zone/monitoring zone around the electrode, actively map neurological behavior in the vicinity of the probe 456 and the like. The probe 456 and/or associated elongate member may include an embedded circuit in accordance with the present disclosure to provide pre-amplification and/or switch functionality for one or more of the electrodes in the linear array 456. In aspects, the probe 456 may include a tip electrode 460 in accordance with the present disclosure. In aspects, the probe 456 may include one or more insulated regions 458 configured to provide electrical isolation between aspects of the probe 456 and the surrounding tissues upon deployment. In aspects, the linear electrode array 462a-e may be used to determine the depth of penetration of the probe 456 into the wall of a lumen during a deployment procedure. Such information may be advantageous to ensure precise positioning of the probe 456 during a monitoring and/or treatment session.

FIG. 4g shows aspects of a probe 464 in accordance with the present disclosure including an array of electrodes 470a-c arranged in along the length and around the circumference thereof. Such an electrode array 470a-c may be advantageous for monitoring local field gradients formed by local electrophysiological activity nearby the probe 464 during use. Such field gradients may be used to manually, semi-automatically, and/or automatically direct the probe 464 towards one or more target tissues during a procedure. The electrode array 470a-c may be coupled to one or more circuits to controllably alter the treatment zone/monitoring zone around the electrode, actively map neurological behavior in the vicinity of the probe 464 and the like. The probe 464 and/or associated elongate member may include an embedded circuit in accordance with the present disclosure to provide pre-amplification and/or switch functionality for one or more of the electrodes in the array 470a-c. Such a configuration may be advantageous for orienting a probe tip 468 with respect to a target tissue as part of a procedure in accordance with the present disclosure. In aspects, the probe 464 may include one or more insulated regions 466 configured to electrically isolate one or more aspects of the probe 464 from the surroundings.

In aspects, such a probe may be coupled to one or more circuits configured to generate one or more gradient signals, suitable for directing an operator and/or control algorithm towards the target tissues.

FIG. 4h shows aspects of a probe 474 in accordance with the present disclosure fashioned with a tip electrode 480 and optionally a channel (not explicitly shown) each in accordance with the present disclosure, the remainder of the probe insulated from the surroundings by an insulating layer. The tip of the probe may be honed, so as to allow for penetration of the probe in to tissues without causing substantial damage or requiring excessive force. In aspects, the length 482 of the tip electrode 480 may be designed for an intended purpose (e.g. sensing, stimulation, ablation, blocking, etc.). In aspects, the length 482 of the tip electrode 480 may be more than 0.5 mm, more than 1 mm, more than 0.5 mm so as to support RF ablation procedures. In aspects, the length 482 of the tip electrode 480 may be shorter than 0.25 mm, shorter than 0.1 mm, shorter than 0.01 mm, or the like so as to support stimulation and/or sensing procedures.

The channel may be coupled to a fluid reservoir near to the control end of an associated surgical tool, so as to deliver 486 a fluid, chemical agent, or medicament 484 to a target tissue in the vicinity of the tip of the probe 474 during a procedure.

In aspects, the probe 474 may include a stabilizing element 476 in accordance with the present disclosure. The stabilizing element 476 may include a standoff region, configured to provide a hard stop during insertion of the probe 474 through a lumen wall. In aspects, the hard stop may be positioned at a length 482 of greater than 0.5 mm, 1 mm, 2 mm, 4 mm, or the like from the tip of the probe 474. In aspects, the length 482 between the tip of the probe 474 and the stabilizing element 476 may be adjustable (e.g. via a mechanism within the control end of a coupled surgical tool, etc.). In aspects, the shank 478 of the probe 474 may be slidingly coupled with the stabilizing element 476, may be fixed thereto, may be insulated thereby, etc.

Figure 5B:
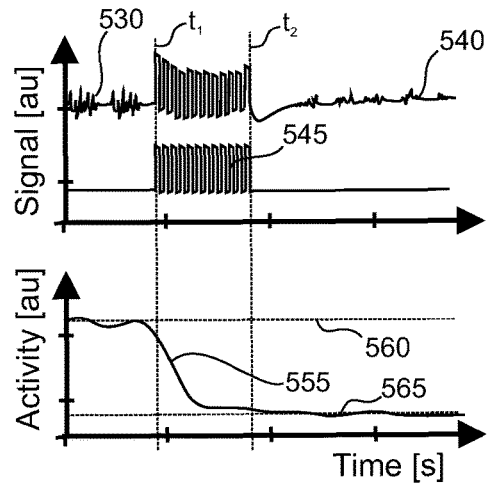

FIGS. 5a-b show aspects of a surgical tool 510 and a temporal plot of monitored signals for performing a surgical procedure in accordance with the present disclosure. FIG. 5a shows a surgical tool 510 with an elongate member 512 and a plurality of probes 514a-f placed inside a lumen 16 (e.g. a vessel, an artery, a renal artery, etc.) within a body. The elongate member 512 may be configured to traverse a guide wire 518 to assist with placement thereof within the lumen 16. The surgical tool 510 is shown with a plurality of probes 514a-f deployed through the lumen wall 18 with tips protruding into regions of target tissue 20a,b. In the non-limiting example shown, six probes 514a-f in accordance with the present disclosure are arranged along the length of the lumen 16 in the plane of FIG. 5a. As shown, considerably more probes may be coupled to the elongate member 512. The elongate member 512 is positioned within the lumen 16 associated with the target tissue 20a,b but may also be routed through an access lumen 14 (such as an artery, an aorta, a femoral artery, a vein, a ureter, a bowel, etc.). The elongate member 512 may couple the distal tip of the surgical tool 510 (as shown in FIG. 5a) to a control end 516 and/or a controller in accordance with the present disclosure. In aspects, the six probes 514a-f may be configured for monitoring, tracking, and/or treating one or more regions of the target tissues 20a,b.

FIG. 5b shows examples of temporal signals obtained from probes during a treatment. Neural activity 540 as captured by a tip electrode included in probe 514b is shown along the temporal axis. A treatment current 545 (e.g. a temporary and/or permanent blocking current) is applied between probes 514a and 514e at time t1 through to time t2. FIG. 5b includes an integrated signal relating to neurological traffic 555 as measured at probe 2 throughout the procedure, which may be used to determine when the procedure is completed, to compare activities before 560 (relating to signals 530) and after 565 (relating to signals 540) treatment, etc. In the case of a temporary block, the monitoring may be used to determine if the probes are oriented in the correct target tissues. In the case of a permanent block, the monitoring may be used to predict recovery and/or completeness of the block for a period of time before retraction of the probes and subsequent removal of the surgical tool from the lumen.

Figure 6A:
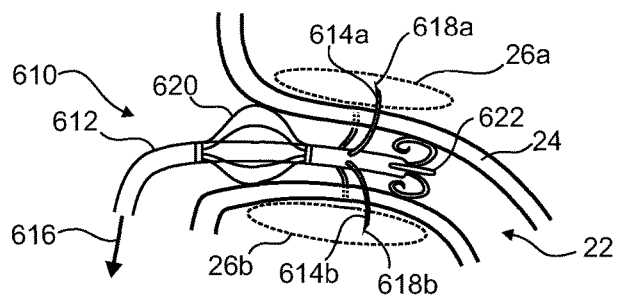
FIGS. 6a-f show aspects of surgical tools accordance with the present disclosure and examples of how such a tool may be placed within a lumen.

FIGS. 6a-f show aspects of surgical tools accordance with the present disclosure and examples of how such a tool may be placed and/or stabilized within a lumen during a procedure. FIG. 6a shows a surgical tool 610 with an elongate member 612 coupled with one or more stabilizing members 620, 622 each in accordance with the present disclosure and positioned within a lumen 22. Such stabilizing members 620, 622 (i.e. flexible members, beams, meshes, wire cages, filters, etc.) may be configured so as to deploy-ably bias the elongate member 612 against the wall 24 of an associated lumen 22, and/or to orient the elongate member 612 to the wall 24 during a procedure. The surgical tool 610 may include a plurality of probes 614a,b configured (shown deployed into the lumen walls 24) so as to easily access the target tissues 26a,b during a procedure. In aspects, the elongate member 612 may be configured with a guide channel configured so as to accept a guide wire there through (i.e. to facilitate easy of placement within a lumen during a procedure).

The elongate member 612 may provide electrical, mechanical, and/or fluid coupling between any one of the probes 614a,b, the stabilizing members 620, 622 and the control end 616 of the surgical tool 610.

The wire basket stabilizing member 620 is shown as an expandable wire basket arrangement. In aspects an actuator or mechanism coupled to the control end 616 of the surgical tool 610 may be used to deploy the wire basket stabilizing member 620 during a placement procedure.

In aspects, the elongate member 612 may include a curled tip stabilizing member 620, which includes a plurality of wire members configured so as to curl outwardly upon deployment from the elongate member 612. The wire members configured with blunt tips so as to bias against the lumen wall 24 upon deployment without puncturing there through.

One or more probes 614a,b may include one or more electrodes 618a,b to interact with local tissues upon deployment, and/or to monitor the deployment process, ensure proper deployment into the target tissues 20a,b, or the like.

Figures 6B, 6C, 6D, 6E:
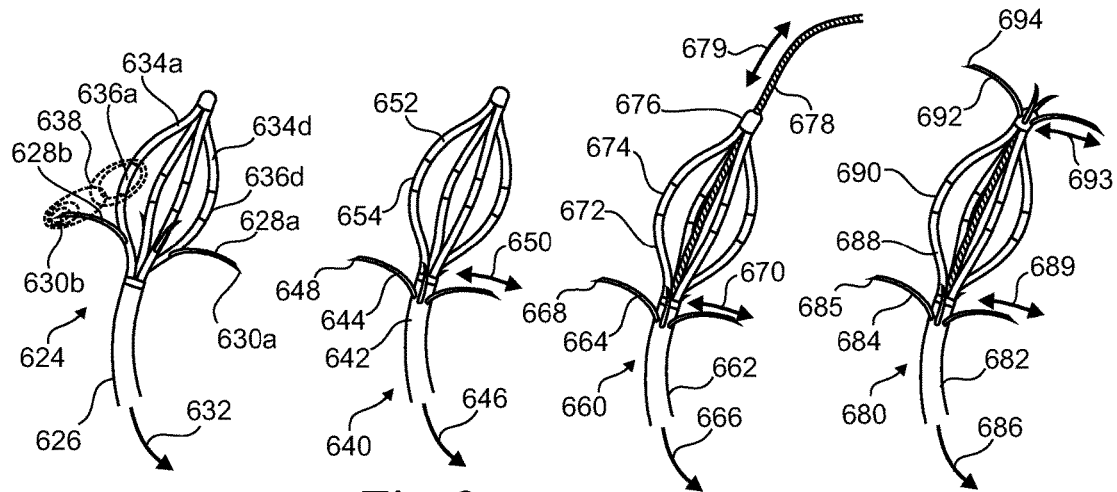

FIG. 6b shows a distal tip of a surgical tool 624 with a basket catheter stabilizing member 634 including a plurality of stabilizing wires 634a-d, arranged at the tip of the elongate member 626. In aspects, the basket catheter stabilizing member 634 may include one or more electrodes 636a-d configured so as to be biased towards the wall of a lumen during placement and deployment therein. The basket catheter 634 and/or elongate member 626 may include channels and/or be coupled to one or more probes 628a-b so as to provide a base from which the probes 628a,b may be advanced towards the target tissues during a procedure. During a treatment, one or more probes 628a,b may be electrically interfaced 638 with one or more additional probes 628a,b or basket catheter electrodes 636a-d during a procedure to sense, stimulate, and/or treat tissues. One or more probes 628a,b may include one or more electrodes 630a,b so as to provide a path for the electrical interfacing 638 during a procedure.

As shown in FIG. 6b, the probes 628a,b are arranged so as to protrude from the wires 634a-d of the basket stabilizing member 634. Such an arrangement may be advantageous in that the wires for the basket stabilizing member 634 may include channels through which the probes 628a,b may be delivered to the target tissues upon deployment.

One or more of the probes 628a,b, elongate member 626, basket stabilizing member 634, one or more electrodes 636a-d on the basket stabilizing member 634 may be coupled with a control end 632 of the surgical tool 624 to communicate electrical signals, a fluid, and/or actuation of deployment and/or positioning aspects during a procedure.

FIG. 6c shows aspects of a surgical tool 640 with a basket catheter stabilizing member 652 including a plurality of stabilizing wires, arranged at the tip of the elongate member 642. In aspects, the basket catheter stabilizing member 652 may include one or more electrodes 654 configured so as to be biased towards the wall of a lumen during placement and deployment therein. The basket catheter 652 and/or elongate member 642 may include channels and/or be coupled to one or more probes 644 so as to provide a base from which the probes 644 may be advanced towards or retracted from 650 the target tissues during a procedure. During a treatment, one or more probes 644 may be electrically interfaced with one or more additional probes, basket stabilizing electrodes 654, or remotely coupled electrodes (e.g. a patch electrode, an electrode positioned along the elongate member 642, etc.), to sense, stimulate, and/or treat tissues. One or more probes 644 may include one or more electrodes 648 so as to provide a path for the electrical interfacing during a procedure.

As shown in FIG. 6c, the probes 644 are arranged so as to protrude from the elongate member 642.

One or more of the probes 644, elongate member 642, basket stabilizing member 652, one or more electrodes 654 on the basket stabilizing member 652 may be coupled with a control end 646 of the surgical tool 640 to communicate electrical signals, a fluid, and/or actuation of deployment and/or positioning aspects during a procedure.

FIG. 6d shows aspects of a surgical tool 660 with a basket catheter stabilizing member 672 including a plurality of stabilizing wires, arranged at the tip of the elongate member 662. In aspects, the basket catheter stabilizing member 672 may include one or more electrodes 674 configured so as to be biased towards the wall of a lumen during placement and deployment therein. The basket catheter 672 and/or elongate member 662 may include channels and/or be coupled to one or more probes 664 so as to provide a base from which the probes 664 may be advanced towards or retracted from 670 the target tissues during a procedure. During a treatment, one or more probes 664 may be electrically interfaced with one or more additional probes, basket stabilizing electrodes 674, or remotely coupled electrodes (e.g. a patch electrode, an electrode positioned along the elongate member 662, etc.), to sense, stimulate, and/or treat tissues. One or more probes 664 may include one or more electrodes 668 so as to provide a path for the electrical interfacing during a procedure.

As shown in FIG. 6d, the probes 664 may be arranged so as to protrude from the elongate member 662.

One or more of the probes 664, elongate member 662, basket stabilizing member 672, one or more electrodes 674 on the basket stabilizing member 672 may be coupled with a control end 666 of the surgical tool 660 to communicate electrical signals, a fluid, and/or actuation of deployment and/or positioning aspects during a procedure.

The elongate member 662 and the tip of the basket stabilizing member 676 may include a guiding lumen in accordance with the present disclosure through which a guidewire 678 may be advanced or retracted 679 (alternatively, over which the elongate member 662 may be advanced or retracted, etc.) during a placement procedure.

FIG. 6e shows aspects of a surgical tool 680 with a basket catheter stabilizing member 688 including a plurality of stabilizing wires, arranged at the tip of the elongate member 682. In aspects, the basket catheter stabilizing member 688 may include one or more electrodes 690 configured so as to be biased towards the wall of a lumen during placement and deployment therein. The basket catheter 688 and/or elongate member 682 may include channels and/or be coupled to one or more probes 684, 692 so as to provide a base from which the probes 684, 692 may be advanced towards or retracted from 689, 693 the target tissues during a procedure. In aspects, groups of probes 684, 692 may be advanced or retracted 689, 693 independently from one another during such a procedure.

During a treatment, one or more probes 684, 692 may be electrically interfaced with one or more additional probes 692, 684, basket stabilizing electrodes 690, or remotely coupled electrodes (e.g. a patch electrode, an electrode positioned along the elongate member 682, etc.), to sense, stimulate, and/or treat tissues. One or more probes 684, 692 may include one or more electrodes 685, 694 so as to provide a path for the electrical interfacing during a procedure.

As shown in FIG. 6e, the probes 684, 692 may be arranged so as to protrude from the elongate member 682 or the tip of the basket stabilizing member 688. In aspects, such a plurality of groups of probes 684, 692 may be coordinated with one or more basket stabilizer electrodes 690 so as to perform monitoring, a treatment, etc. on the intended target tissues.

One or more of the probes 684, 692, elongate member 682, basket stabilizing member 688, one or more electrodes 690 on the basket stabilizing member 688 may be coupled with a control end 686 of the surgical tool 680 to communicate electrical signals, a fluid, and/or actuation of deployment and/or positioning aspects during a procedure.

The elongate member 682 and the tip of the basket stabilizing member 688 may include one or more conduits or channels in accordance with the present disclosure through which one or more probes 692 maybe may be advanced or retracted 679 during a placement procedure. Such a configuration may be advantageous for independently actuating probes 684, 692 from groups positioned at alternative locations along the length of the elongate member 682.

Figure 6F:
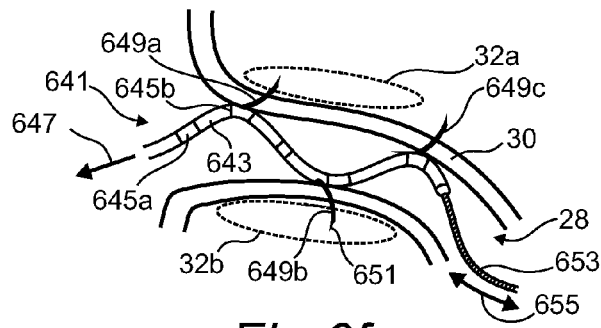

FIG. 6f shows a surgical tool 641 with a helical catheter arranged at the tip of an elongate member 643 deployed within a lumen 28. The helical catheter may optionally include electrodes 645a,b oriented along the length thereof, which may be biased towards the lumen wall 30 during a procedure. The helical catheter may include channels and/or be coupled to one or more probes 649a-c so as to provide a base from which the probes 649a-c may be advanced towards the target tissues 32a,b during a procedure. During a treatment, one or more probes 649a-c may be electrically interfaced with one or more additional probes 649a-c or helical catheter electrodes 645a,b during a procedure to sense, stimulate, and/or treat tissues. The helical catheter may be configured to accommodate a guide wire 653 for simplified placement within a lumen 28. The guide wire 653 may be adjusted 655 (i.e. retracted) in order to allow the helical catheter to take on a helical shape during placement. In this non-limiting example, the guide wire may be configured with a softer tip and a stiffer shank, such that when the helical catheter is advanced over the stiffer shank, it takes on a substantially straight form, and when the guide wire is retracted such that the helical catheter is over the softer tip of the guide wire, the helical catheter may take on a helical shape and thus bias against the lumen wall 30. One or more probes 649a-c may be configured to protrude out from the helix 643 during deployment (i.e. with a trajectory related to the seated state of the helix in the lumen). One or more of the probes 649a-c may include one or more electrodes 651 each in accordance with the present disclosure.

One or more of the probes 649a-c, elongate member 643, helical catheter electrodes 645a,b may be coupled with a control end 647 of the surgical tool 641 to communicate electrical signals, a fluid, and/or actuation of deployment and/or positioning aspects during a procedure.

Figure 7A:
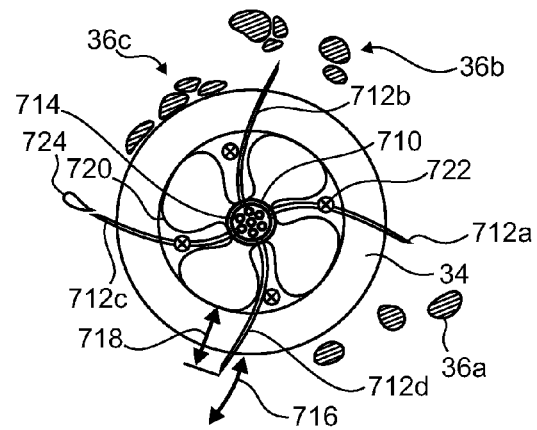
FIGS. 7a-c show aspects of a balloon based surgical tool in accordance with the present disclosure and how such a tool may be seated within a lumen during use.
Figure 7B:
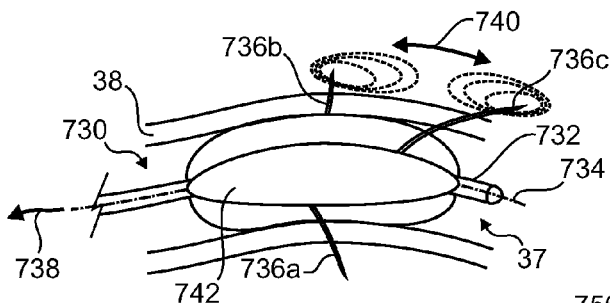
Figure 7C:
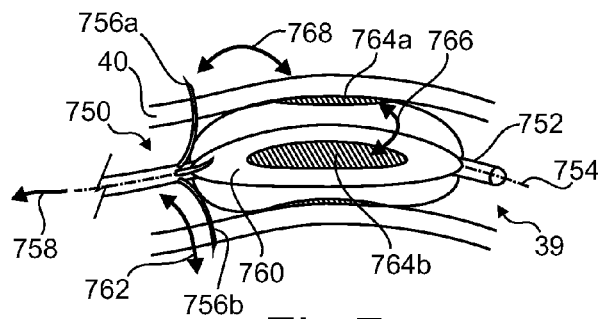

FIGS. 7a-c show aspects of a balloon based surgical tool in accordance with the present disclosure and how such a tool may be seated within a lumen during use. FIG. 7a shows a cross-section of a balloon based surgical tool in accordance with the present disclosure deployed within a lumen. The balloon 720 may be coupled to an elongate member 710 in accordance with the present disclosure. The balloon 720 may be configured to stabilize and/or orient the elongate member 710 with respect to a lumen wall 34 during a placement procedure. The balloon 720 may be configured such that the cross sectional area thereof allows for flow of fluid (e.g. blood, urine, bile, etc.) around the balloon even in the deployed state. Such regions 722 of sustained flow are indicated with markers in FIG. 7a. The elongate member 710 and/or balloon walls 720 may include channels 714 and/or be coupled to one or more probes 712a-d in accordance with the present disclosure, which may be deploy ably advanced 716 into the wall 34 of the lumen during a procedure so as to access one or more target tissue regions 36a-c. In aspects, the depth of penetration 718 into the wall of the lumen 34 may be controlled via design, electrode feedback during placement (i.e. via changes in inter-electrode impedance, via changes in recorded electrophysiological signals, etc.).

The surgical tool may include means for inflating the balloon (e.g. a fluid delivery circuit, etc.), for deploying and/or retracting the probes, etc. The elongate member may include a guide channel to accommodate placement over a guide wire. In aspects, the surgical tool, elongate member 710, one or more probes 712a-d, and/or balloon wall 720 may include one or more channels and/or pores through which a fluid 724 (e.g. a medicament, a chemical agent, a sclerosing agent, etc.) may be delivered to the target tissue regions 36a-c.

FIG. 7b shows a balloon based surgical tool 730 in accordance with the present disclosure deployed within a lumen 37. The surgical tool 730 includes a balloon 742, which coupled to the elongate member 732, deployed so as to orient the elongate member 732 with respect to the lumen 37 (i.e. so as to align or orient the distal tip axis 734 of the tool 730 with the lumen axis). In aspects, the balloon 742 may also bias against the lumen wall 38 during a placement procedure. One or more probes 736a-c each in accordance with the present disclosure may be coupled to the elongate member 732 and/or balloon 742 are shown in a deployed position, having passed into the wall 38 of the lumen to access the target tissues for monitoring, treatment, etc. In aspects, a treatment and/or stimulating current 740 may be passed between one or more probes 736a-c as part of a procedure.

In aspects, one or more of the probes 736a-c, elongate member 732, balloon 742, or the like may be coupled with a control end 738 of the surgical tool 730 to communicate electrical signals, a fluid, and/or actuation of deployment and/or positioning aspects during a procedure.

FIG. 7c shows a balloon based surgical tool 750 in accordance with the present disclosure deployed within a lumen 39. The surgical tool 750 includes a balloon 760, which coupled to the elongate member 752, deployed so as to orient the elongate member 752 with respect to the lumen 39 (i.e. so as to align or orient the distal tip axis 754 of the tool 750 with the lumen axis). In aspects, the balloon 760 may also bias against the lumen wall 40 during a placement procedure. One or more probes 756a-c each in accordance with the present disclosure may be coupled to the elongate member 752 and/or balloon 760 are shown in a deployed position, having passed 762 into the wall 40 of the lumen to access the target tissues for monitoring, treatment, etc. The balloon 760 may include one or more balloon electrodes 764a,b each in accordance with the present disclosure.

In aspects, a treatment and/or stimulating current 768, 766 may be passed between one or more probes 756a,b and one or more balloon electrodes 764a,b, one or more electrodes on the elongate member 752, and/or an externally placed electrode as part of a procedure. In aspects, one or more balloon electrodes 764a,b may serve as a reference electrode for a monitoring process using one or more electrodes on one or more probes 756a,b.

In aspects, one or more of the probes 756a-c, elongate member 752, balloon 760, balloon electrode 764a,b, or the like may be coupled with a control end 758 of the surgical tool 750 to communicate electrical signals, a fluid, and/or actuation of deployment and/or positioning aspects during a procedure.

Figure 8:
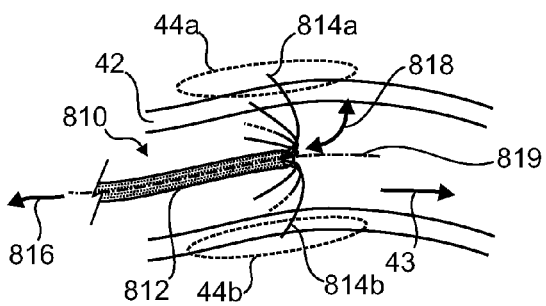
FIG. 8 shows aspects of a surgical tool with a plurality of probes in accordance with the present disclosure.

FIG. 8 shows aspects of a surgical tool 810 with a plurality of probes 814a,b in accordance with the present disclosure. The surgical tool 810 may be configured such one or more of the probes 814a,b may be deployable 818 from the tip of the associated elongate member 812. The probes 814a,b may be curved along at least a portion of the length thereof, such that the probes 814a,b curve outwards into the lumen walls 42 during deployment 818. The probes 814a,b may include one or more stabilizing features (e.g. elliptical geometry, a channel stabilizing notch, a flattened face, stabilizing elements, etc.) such that the axis of curvature remains substantially perpendicular to the axis of the elongate member 819, so that the probes 814a,b deploy in a predictable manner during a deployment procedure. The surgical tool 810 is shown in a deployed state whereby the probes 814a,b have penetrated into the wall 42 of the lumen as part of a deployment process, a monitoring process, a stimulating process, a treatment process, etc.

In aspects, the elongate member 812 may include a plurality of such end-type deployment mechanisms. In aspects, the elongate member 812 may include a sheath into which a second arrangement of probes may be situated. The sheath probes may be deployed independently of the tip probes 814a,b, such that a plurality of treatment sites 44a,b may be accessed simultaneously during a procedure. In aspects, one or more circuits coupled with one or more probes 814a,b, may be configured so as to communicate a current between one or more sheath probes and one or more tip probes, etc. In aspects, one or more probes 814a,b and/or the elongate member 812 (or electrodes, channels, etc. included therein), may be coupled with a control end 816 of the surgical tool 810 so as to perform one or more aspects of a procedure in accordance with the present disclosure.

The arrangement shown in FIG. 8 may be advantageous to allow for interfacing of the probes 814a,b with the target treatment sites 44a,b while maintaining fluid flow 43 through the lumen.

Figure 9A:
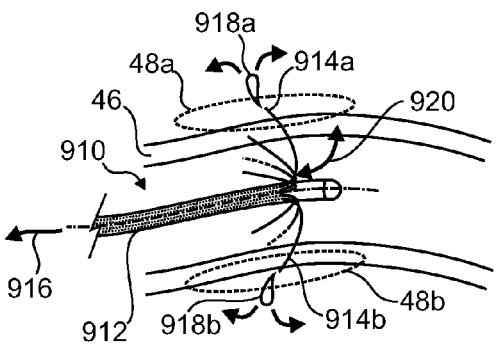
FIGS. 9a-b show aspects of a surgical tool with fluid administration aspects in accordance with the present disclosure.
Figure 9B:
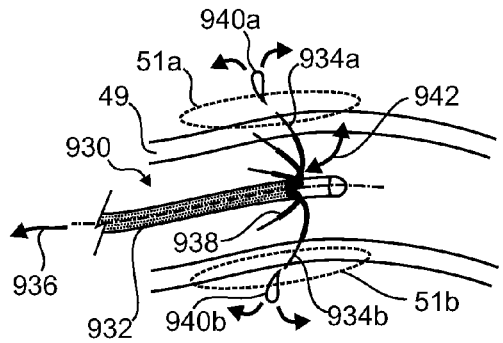

FIGS. 9a-b show aspects of a surgical tool with fluid administration aspects in accordance with the present disclosure. FIG. 9a shows aspects of a surgical tool 910 including a plurality of probes 914a,b, one or more of the probes 914a,b including a channel (not explicitly shown) for delivery of a fluid 918a,b to a target tissue region 48a,b in or through a lumen wall 46. The surgical tool 910 may be configured with ports located along the side of the elongate member 912. The ports may be provide access such that one or more probes 914a,b may be advanced through the ports during deployment 920 into an adjacent lumen wall 46. Such a configuration may be advantageous for providing stability to the deployable probes 914a,b from the elongate member 912 without adjusting the shape and maintaining the orientation of any probe 914a,b in particular during deployment 920.

In aspects, one or more of the probes 914a,b, the elongate member 912, or the like may be coupled with a control end 916 of the surgical tool 910 to communicate electrical signals, a fluid, and/or actuation of deployment and/or positioning aspects during a procedure.

FIG. 9b shows aspects of a surgical tool 930 including a plurality of probes 934a,b, one or more of the probes 934a,b including a channel (not explicitly shown) for delivery of a fluid 940a,b in accordance with the present disclosure to a target tissue region 51a,b in or through a lumen wall 49. In aspects, the surgical tool 930 may be configured with ports located along the side of the elongate member 932. The ports may be provide access such that one or more probes 934a,b may be advanced through the ports during deployment 942 into an adjacent lumen wall 49. Such a configuration may be advantageous for providing stability to the deployable probes 934a,b from the elongate member 932 without adjusting the shape and maintaining the orientation of any probe 934a,b in particular during deployment 942.

In aspects, one or more of the probes 934a,b, the elongate member 932, or the like may be coupled with a control end 936 of the surgical tool 930 to communicate electrical signals, a fluid, and/or actuation of deployment and/or positioning aspects during a procedure.

In aspects, one or more of the probes 934a,b may include a stabilizing element 938 in accordance with the present disclosure, configured to assist with orientation of the elongate member 932 within the lumen during a procedure, to control the depth of penetration of the probes 934a,b into the lumen wall 49 during deployment, or the like.

In aspects, the ports and/or channels in the elongate member 912, 932 may be formed via micromolding, via passage of one or more microtubes through the length of the elongate member 912, 932, the microtubes curved at the tips so as to change the trajectory of a probe 914a,b, 934a,b is advanced there through. In aspects, such structures may be manufactured by placing pre-bent wire mandrels through the microtubes so as to retain a bent shape during fabrication. After the tubes are bonded to the elongate member 912, 932, the wire mandrels may be removed, leaving the curved tubes behind to direct one or more probes 914a,b, 934a,b as they are advanced there through.

Figure 10A:
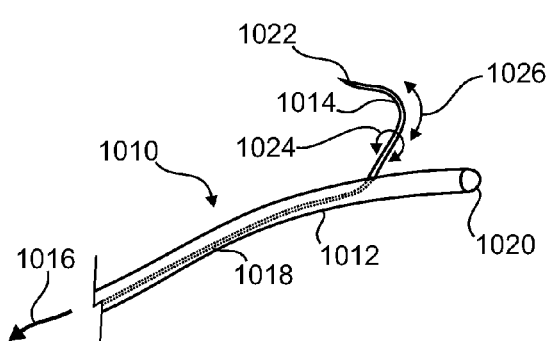

FIGS. 10a-e show aspects of steerable probes in accordance with the present disclosure. FIG. 10a shows a steerable probe 1014 including a bent tip 1022 protruding from a channel 1018 placed into and/or included in an elongate member 1012 in accordance with the present disclosure. The steerable probe 1014 may be advanced/retracted 1026, and torqued 1024 during use via mechanical inputs coupled to a control end 1016 of the catheter 1010. With the advent of the bent tip 1022, the steerable probe 1014 may be controllably advanced/retracted 1026 and/or reoriented 1024 within tissues during a deployment procedure. The probe may include one or more electrodes 1022 in accordance with the present disclosure. The electrodes 1022 may be coupled to one or more circuits configured to assist with guidance of the probe to a target tissue, etc., a control end 1016 of the catheter 1010, or the like. In aspects, the catheter tip 1020 may include one or more electrodes, soft tips (i.e. for assisting with access to a treatment lumen), or the like.

Figure 10B:
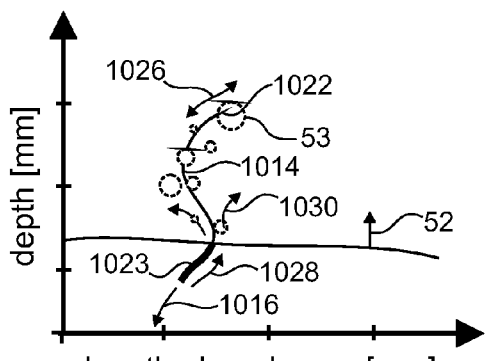

FIG. 10b shows a path 1028 followed by a steerable probe 1014 in accordance with the present disclosure as it is advanced from an elongate member 1016, through a lumen wall 52, and into one or more regions of target tissue 53. In aspects, the steerable probe 1014 may include a stabilizing element 1023 in accordance with the present disclosure. A method for treating such target tissues 53 may include assessing if one or more electrodes 1022 on the probe 1014 are near to the target tissue 53 (e.g. through determination of local electrophysiological signals formed therein, via changes in impedance during advance of the probe 1014, etc.), if so, applying a radiofrequency current via the probe 1014 (and optionally via one or more of the electrodes 1022 included on the probe 1014), administering a chemical agent (i.e. via the probe 1014), etc. so as to treat the tissue 53.

In aspects, the steerable probe 1014 may be rotated during placement so as to alter a trajectory 1030 of the tip as it is advanced 1026 through the lumen wall 52.

In aspects, the activity level monitored at one or more electrodes 1022 on a probe 1014 during advancement through the tissue may be overlaid onto a GUI, an imaging system, etc. so as to indicate to an operator one or more features of the tissue most in the vicinity of the electrodes 1022 during the placement procedure. In aspects, such feedback may be applied at other electrode sites in the system before, during, and/or after a treatment to assess changes in activity levels, in function, in sensitivity, etc. as part of a diagnostic procedure, a treatment, etc.

FIG. 10c shows aspects of a steerable probe 1042 in accordance with the present disclosure. The steerable probe 1042 may include a channel 1041 for providing delivery 1054 of a fluid 1046 towards and/or sampling of fluid from tissues near the tip of the probe. The steerable probe 1042 may include one or more electrodes 1044 in accordance with the present disclosure. The steerable probe 1042 may include a bent tip for assisting with the steering thereof. The steerable probe may include an optional supporting sheath 1040, configured so as to provide a substantially stiff bias near to the tip of the steerable probe 1042 (i.e. optionally providing a stabilizing function for the probe). The steerable probe 1042 may be advanced/retracted 1048, and/or torqued 1050 so as to adjust the position 1052 of the tip thereof with respect to the target tissues. In aspects, the probe tip 1042 and the supporting sheath 1040 may be advanced or retracted 1048 independently of each other during use.

FIG. 10d shows aspects of a steerable probe 1062 in accordance with the present disclosure. The steerable probe 1062 is shown slide ably coupled 1066 to a sheath 1060 further coupled to an elongate member in accordance with the present disclosure. In FIG. 10d, the steerable probe 1062 is shown protruding from the tip of the sheath 1060. The steerable probe 1062 may include one or more electrodes 1064 in accordance with the present disclosure. In aspects, the steerable probe 1062 may be advanced 1070, and/or rotated 1068 as part of a deployment procedure.

FIG. 10e shows aspects of a steerable probe 1080 in accordance with the present disclosure. The steerable probe 1080 includes a tapered tip, configured so as to reduce the entry forces required to advance the probe 1080 through tissue. The steerable probe 1080 includes a tip electrode 1084 configured at the tip of the probe 1080 and an insulated region (elsewhere). The probe 1080 includes a cuff electrode 1082 suitable for stimulation, ablation, and/or use as a reference electrode, combinations thereof, or the like. The probe 1080 may be electrically coupled to a controller 1086, a control end of the surgical tool, and/or circuit in accordance with the present disclosure configured to interface with the electrodes 1084, 1082 thereupon. In aspects, the probe 1080 may include an embedded circuit in accordance with the present disclosure coupled to one or more of the electrodes.

FIGS. 11a,b show aspects of surgical tools in accordance with the present disclosure placed in a lumen during treatment of a neural body (such as, in this non-limiting example, a carotid body). FIG. 11a shows a distal tip of a surgical tool 1109 passing from a main carotid artery 52 into the external carotid artery 53. The surgical tool 1109 includes an elongate member 1110 configured for placement in a lumen 52, 53, 54 in the vicinity of the neural body 56 (i.e. in this case a carotid body), neurons coupled thereto 58a,b, and/or receptors 59 (i.e. in this case baroreceptors lining wall 55 of the internal carotid artery 54). The elongate member 1110 includes one or more probes 1114a,b each in accordance with the present disclosure, coupled to the elongate member 1110 and configured so as to be actuate-ably advanced 1116 from the elongate member 1110 into the wall of the lumen 53, 52, 54, so as to be advanced towards a target tissue 57a-e (e.g. one or more regions of the neural body 57a, a region adjacent to the neural body 57d, nerves and/or nerve plexuses coupled to the neural body 57b,c, and/or regions including receptors 57e in the vicinity of the neural body 56 and/or the walls 55 of the adjacent lumens 52, 53, 54, etc.). FIG. 11a shows a first probe 1114b in a deployed condition, oriented within a specific region 57a of the carotid body 56, and a second probe 1114a with electrodes/tip positioned within a neural structure 58a coupled with the carotid body 56. The positions of the probes 1114a,b may have been selected based on neurological activity monitored via one or more electrodes included in the probes 1114a,b (i.e. such as one or more microelectrodes in the tip of the probes 1114a,b), based upon readings in one or more electrodes on the probes 1114a,b, or the like. The probes 1114a,b may be configured so as to monitor, stimulate, and or ablate one or more tissue sites in the vicinity thereof. In aspects, one or more of the probes 1114a,b may be configured to monitor one or more local physiological responses to a stimulus, potentially applied near to, or remotely to a surgical site, a target tissue 57a-e, etc.

In aspects, one or more of the probes 1114a,b may be configured to stimulate, and/or treat one or more regions of the carotid body 56, and/or one or more target tissues 57a-e as part of a surgical procedure. The region of treatment as well as the extent of treatment may be monitored and/or controlled by one or more electrodes on one or more of the probes 1114*a,b*.

In aspects, a probe (not explicitly shown) in accordance with the present disclosure, including a plurality of electrodes may be configured to expandingly and/or sequentially treat regions 57*d* of the neural body 56, and/or surrounding target tissues 57*a-e*. In such a configuration, the treatment zone may be extended, starting from a first location as determined by the position of a first electrode and/or electrode pair, and may be simultaneously monitored by one or more surrounding electrodes on one or more of the probes, and/or an additional probe 1120 (perhaps also placed within or near to the neural body 56). As the neural activity changes in the vicinity of one or more of the alternative electrodes (as determined by simultaneous and/or sequential monitoring therefrom), the extent of an affected region as formed during the treatment may be tracked and the treatment may be halted at the appropriate time based upon the desired surgical extent of the process. In aspects, one or more of the electrodes may be incorporated into the treatment of the target tissues.

In aspects, one or more electrodes and/or probes 1114*a* may be configured to monitor, to stimulate, and/or to alter (e.g. deaden or block neural traffic, ablate the nerves, etc.), neurological activity in one or more nerve bundles 58*a,b* extending from the neural body 56 (as shown in FIG. 11*a* the second probe 1114*a*). Changes in neural traffic after a surgical procedure, in response to a stimulus, or the like may be used to assist in controllably treating one or more regions of target tissue 57*d* in the neural body 56, or other target tissues 57*a-e* in the vicinity thereof.

FIG. 11*a* also shows an alternative placement for a surgical tool 1120 to access the neural body 56 or target tissues 57*a-e* in the vicinity thereof. In aspects, a plurality of surgical tools may be used to access one or more regions of the neural body or surrounding tissues simultaneously as part of a treatment, diagnostic, and/or monitoring procedure.

FIG. 11*b* shows a distal tip of a surgical tool 1139 passing alongside of a neural body 56 (in this case a carotid body) along an internal carotid artery. The surgical tool 1139 includes an elongate member 1140. The elongate member 1140 includes one or more probes 1142 each in accordance with the present disclosure, coupled to the elongate member 1140 and configured, shaped, and dimensioned so as to be actuate-ably advanced from the elongate member 1140 into the wall 55 of the lumen, so as to be advanced towards a target tissue 57*a-e* (e.g. one or more regions of the neural body 57*a*, a region adjacent to the neural body 57*d*, nerves and/or nerve plexuses coupled to the neural body 57*b,c*, and/or regions including receptors 57*e* in the vicinity of the neural body 56 and/or the walls 55 of the adjacent lumens 52, 53, 54, etc.). In aspects, the elongate member 1140 may include a conduit or channel 1148 to accommodate passage of one or more of the probes 1142 there through.

FIG. 11*b* shows the probe 1142 in a deployed condition, oriented within a specific region 57*c* of the carotid body 56, having been steerably delivered up one or more carotid precapillary arterioles, which supply blood to the carotid body 56. The probe 1142 may include one or more electrodes 1144 each in accordance with the present disclosure to monitor, stimulate, and/or ablate tissues in the vicinity of the target region 57*c*. Such a configuration may be advantageous for directly monitoring, influencing, and/or altering electrophysiological activity in one or more regions of the neural body 56 during a procedure.

In aspects, the surgical tool 1139, elongate body 1140, or the like may include one or more additional electrodes 1146, which may serve as counter electrodes, RF ablation electrodes, reference electrodes, or the like for coordinated use with the probe 1142 and/or an electrode 1144 situated there upon.

The positions of the probe 1142 may have been selected based on neurological activity monitored via one or more of the electrodes 1144 included in the probe 1142 (i.e. such as one or more microelectrodes 1144 in the tip of the probe 1142), based upon readings in one or more electrodes 1144 on the probe 1142, or the like. The probes 1142 may be configured so as to monitor, stimulate, and or ablate one or more tissue sites in the vicinity thereof. In aspects, the probe 1142 may be configured to monitor one or more local physiological responses to a stimulus, potentially applied near to, or remotely to a surgical site, a target tissue 57*a-e*, etc.

In aspects, the probe 1142 may include a needle like tip (e.g. a sharpened tip, a honed tip, a serrated tip, a pointed tip, etc.) for penetrating into the lumen wall 55 upon deployment. In aspects, the probe 1142 may include a soft tapered tip (i.e. a flexible shank with a narrowed yet blunt tip) for accessing arterioles and other small lumens without penetrating through the walls thereof. Such a configuration may be advantageous for snaking a probe 1142 along a small lumen towards a target region within the parenchyma of an organ, within the wall of a larger vessel, etc.

FIG. 12 shows aspects of an elongate member 1210 with an embedded circuit 1218 in accordance with the present disclosure. The embedded circuit 1218 may be incorporated into a channel 1211 within the elongate member 1210, into a wall of the elongate member 1210, or the like. In aspects, the embedded circuit 1218 may be electrically (and optionally mechanically) coupled to one or more probes 1216 and/or electrodes in the surgical tool (i.e. towards the tip end of the elongate member) and electrically (and optionally mechanically) coupled to a controller 1220, connector, or the like (i.e. towards the control end of the elongate member). The circuit 1218 may be configured so as to amplify one or more signals obtained via one or more probes 1216 and/or electrodes in the surgical tool. The circuit 1218 may be configured to receive power from and to communicate with an associated controller 1220 (optionally externally located).

In aspects, the embedded circuit 1218 may be coupled to a substrate, the substrate electrically and mechanically interfaced with one or more probes 1216 and an associated push rod 1222, tube or the like (i.e. a load transfer unit used to communicate actuation signals from the control end of the elongate member to the probes). Such a push rod may be advantageous for advancing (pushing), retracting (pulling), rotating (twisting), one or more aspects of the probes 1216, etc. The embedded circuit 1218 may be encapsulated in a hard coat, optionally hermetically sealed, etc. so as to better carry load and/or be better isolated from fluids during a procedure. FIG. 12 shows the embedded circuit 1218 interconnected with power and signal lines 1224, which may be coupled with a controller 1220, a connector, or the like. Also shown, the embedded circuit 1218 may be connected with one or more leads 1212 associated with one or more probes 1216. In aspects, the leads 1212 are shanks of the associated probes 1216.

In aspects, the embedded circuit 1218 may be provided as a component within a flip-chip assembly, fastened to a high density, or ultra-high density interconnect board (HDI board). The HDI board may include a plurality of electrical and/or mechanical interconnects to fasten one or more of the leads 1212, power and signal lines 1224, and/or push rods 1222, so as to form a physically strong interconnection for the embedded circuit 1218 into the surgical tool. In aspects, the HDI board may be potted in a high strength material, selected so as to increase the overall load bearing capability of the HDI board, to protect the embedded circuit 1218, or the like.

FIGS. 13a-b show schematics of an embedded circuit in accordance with the present disclosure. FIG. 13a shows a schematic of an embedded circuit including a preamplifier 1310 coupled to one or more electrodes in the surgical tool. The preamplifier inputs 1314 may be configured so as to minimize losses between the sensing electrodes, between the sensing electrodes and the preamplifier inputs, etc. The preamplifier 1310 may be configured so as to amplify the differential signal(s) between two or more electrodes of the surgical tool while minimizing the common mode signal(s) between the electrodes. In aspects, the preamplifier 1310 may be configured with input impedance greater than 100 Mohm, 1 Gohm, 10 Gohm, 100 Gohm, etc. and with an input capacitance of less than 10 pF, less than 5 pF, less than 1 pF, etc.

In aspects, the embedded circuit may include an analog to digital converter 1312 coupled to the preamplifier 1310, a signal conditioner, a multiplexer, or the like (i.e. other aspects within an embedded circuit in accordance with the present disclosure), and coupled to the controller 1318 and/or a connector (i.e. generally situated at and/or coupled to the control end of an associated elongate member).

In aspects, the embedded circuit may include one or more elements for interfacing with and/or to receive a signal 1322 associated with a guard electrode driver (i.e. attached to a shield, and/or an electrode suitable for electrical contact with a body during a procedure). The guard may be provided to satisfy a three electrode configuration for monitoring electrophysiological activity at one or more locations within a body during a procedure.

In aspects, the preamplifier 1310 may be configured to accept one or more electrode signals 1320 from one or more electrodes located on an associated elongate member, as part of a related system, from a body patch, or the like. Such an electrode signal 1320 may be used as part of an internal reference signal, used to generate a reference signal, etc.

FIG. 13b shows aspects of an embedded circuit in accordance with the present disclosure. The embedded circuit may include a preamplifier and a switch network 1340 coupled to one or more electrodes 1346 in accordance with the present disclosure. The preamplifier and switch network 1340 may be configured so as to manage signal traffic to and/or from one or more electrodes 1346 in the surgical tool (e.g. as part of a stimulation, ablation, blocking, treatment protocol, etc.), and/or to amplify electrophysiological and/or bioimpedance signals harvested from one or more electrodes 1346 during a procedure (e.g. as part of a diagnostic, sensing, monitoring, closed loop therapeutic procedure, etc.). Thus the preamplifier and switch network 1340 may be configured to adapt traffic from a potentially large number of distal tip leads 1346 (e.g. connected to sensors, electrodes, etc.), with a relatively fewer number of leads associated with a multiplexed signal 1344, and/or a digital signal 1348 and power leads, for a considerably reduced lead configuration. The preamplifier and/or switch network 1340 may be interfaced with a second switch network, analog to digital converter 1342, and/or a modem for communicating signals 1348 to/from a controller.

In aspects, the embedded circuit may include aspects for interfacing with and/or to receive a signal associated with a guard electrode driver 1350 (e.g. attached to a shield, and/or an electrode suitable for electrical contact with a body during a procedure). The guard 1350 may be provided to satisfy a three electrode configuration for monitoring electrophysiological activity at one or more locations within a body during a procedure.

FIGS. 14a-b show aspects of a surgical tool with multiple probes 1412a,b in accordance with the present disclosure and an example of signals obtained therefrom during a surgical procedure. FIG. 14a shows aspects of probes 1412a,b associated with a surgical tool, positioned in the vicinity of a target tissues 62 (e.g. deployed through the wall 61 of a nearby lumen). Two probes 1412a,b are shown. The first probe 1412b is shown deployed into the wall 61 of the lumen with an electrode 1414a situated at point a. The second probe 1412b is shown deployed into the target tissue with an electrode 1414b situated at site b. The second probe 1412b may optionally have one or more electrodes 1414c along the length thereof, thus an electrode 1414c located within the lumen wall 61 may be located on the second probe 1412b at site c. The probes 1412a,b and/or system may include one or more electrodes such as attached to the probes 1412a,b and/or an associated elongate member (e.g. at site d), or additional electrodes placed elsewhere on or in the body (e.g. at site e). The probes 1412a,b and associated electrodes 1414a-c may be configured to monitor, stimulate, and/or treat one or more tissues in the body. One or more electrodes 1414a-c may be coupled to one or more circuits configured to capture one or more signals therefrom during a procedure. In aspects, one or more of the signals may be referenced to a site within the body (e.g. sites c, d, and/or e, for example).

FIG. 14b, shows temporal signals captured from the electrodes situated at site a, and site b (e.g. both referenced to a common reference point, in this case site e). The captured signals are shown in the chart. In aspects, the systems may include one or more processors configured to analyze the signals obtained from sites a and b, in order to better separate the origin of the content from each (e.g. to eliminate cross talk, to remove baseline signals, to highlight activity from one site or the other, to remove electromyographic content from a neurographic signal, etc.). In the non-limiting example shown in FIG. 14b, an optimal subtraction algorithm may be employed by the processor to remove the dominant content of the signal obtained at site b from site a (as opposed to a straight subtraction which may be achieved by referencing one signal against the other). Some non-limiting examples of such algorithms include cross-talk removal functions, blind signal separation algorithms, a least mean squares algorithm, nonlinear recursive least squares algorithms, limited connectivity neural networks, etc. In aspects, algorithms to extract task-dependent modulation of oscillatory and/or non-oscillatory components, population synchrony changes, etc. of traffic measured at site a, and site b may be employed in the analysis. Changes in population synchrony may be an indicator of the state of completion of an associated surgical procedure (e.g. a neuromodulation procedure, a denervation procedure, etc.). Such algorithms may be employed to further extract content arising from one or more regions of target tissue nearer to site a, or site b than the other. Such an approach may be advantageous to detect a potentially subtle change in overall activity, or to more easily extract such changes from the combined signals for analysis (e.g. as part of a monitoring process occurring during a stimulus response, during a surgical procedure, etc.).

FIGS. 15a-b show aspects of probes in accordance with the present disclosure. FIG. 15a shows a probe 1512 in accordance with the present disclosure including a conducting sheath 1516 coupled coaxially to a shaft 1515 of the probe 1512 (optionally slidingly coupled thereto). The sheath 1516 may be coupled to one or more circuits 1524 (e.g. a sensory circuit, an embedded circuit, connector coupled to a controller, a circuit, etc.) optionally in combination with one or more electrodes 1514 on the probe 1512 (such as a tip electrode in accordance with the present disclosure). In aspects, at least a portion of the sheath 1516 may serve as a reference electrode, and/or as an active guard electrode to preserve signal integrity from the tip electrode 1512 to a coupled circuit. In aspects, the sheath 1516 may provide structural support for the probe 1512 during a deployment, insertion, and or retraction process. In aspects, the sheath 1516 may provide a stabilizing function (i.e. provide a function similar to that of a stabilizing element in accordance with the present disclosure), such as via a step change in diameter 1518 or the like, to limit the depth to which the probe 1512 can penetrate into an adjacent volume of tissue. In a method in accordance with the present disclosure, the sheath 1516 may be advanced near to the wall of a lumen and the shaft 1515 of the probe 1512 may be deployed 1522 therefrom, the sheath 1516 providing a stable base from which the probe shaft 1515 may protrude out into the wall of the lumen.

In aspects, the probe 1512 may include one or more electrodes, including a tip electrode 1514 in accordance with the present disclosure. In aspects, the tip electrode 1514 may have an active length 1520 of less than 2 mm, less than 1 mm, less than 0.1 mm, less than 0.01 mm, or the like. In aspects, the shaft 1515 may include an insulated region 1513 with a first insulation thickness (e.g. optionally less than 50 um thick, less than 12 um thick, less than 6 um thick, less than 1 um thick, etc.) so as to provide insulation over the length between the tip electrode 1514 and the sheath 1518. The shaft 1515 may include a second insulated region, such as provided by an inner layer of the sheath 1516. In aspects, the inner layer of the sheath 1516 may be thicker than 5 um, thicker than 25 um, thicker than 100 um, etc.

FIG. 15b shows aspects of a probe 1532 in accordance with the present disclosure including an array of patterned microelectrodes 1534b-f thereupon. The microelectrodes 1534b-f may be configured in spatial relationships (e.g. positioned along a length of the probe 1532, around a circumference of the probe 1532, etc.) such that signals obtained from two or more microelectrodes 1534b-f in the array may be used to guide the tip towards a target tissue within a body. The microelectrodes 1534b-f may be arranged along the length of the probe 1532 at different angles circumferentially around the width of the probe 1532. The small changes in orientation between microelectrodes 1534b-f may help to distinguish local field gradients in the signals obtained from a plurality of such probes 1532. In aspects, the microelectrodes 1534b-f may be coupled to one or more circuits 1538 and associated processors configured to extract field gradient data therefrom. In aspects, one or more processors may be configured to extract a combination of activity related data and/or field gradient data from a plurality of the microelectrodes 1534b-f during a monitoring procedure, a placement procedure, a surgical procedure, etc. Such information may be used to help guide the probe 1532 towards tissue regions with higher activity, along increasing field gradients, and/or to monitor progression of a treatment zone within the vicinity of the probe 1532 (i.e. monitor changes in local activity as related to the treatment process).

In aspects, the probe 1532 may include a tip electrode 1534a configured and dimensioned (i.e. with a length 1536 along the probe 1532), so as to sense, stimulate, block, and/or ablate tissues in the vicinity thereof. In aspects, the probe 1532 may include an insulated region 1533 over the length thereof, configured so as to mechanically and electrically isolate one or more leads coupled to an electrode 1534a-f on the probe 1532 from the surroundings along the length thereof.

Figure 16:
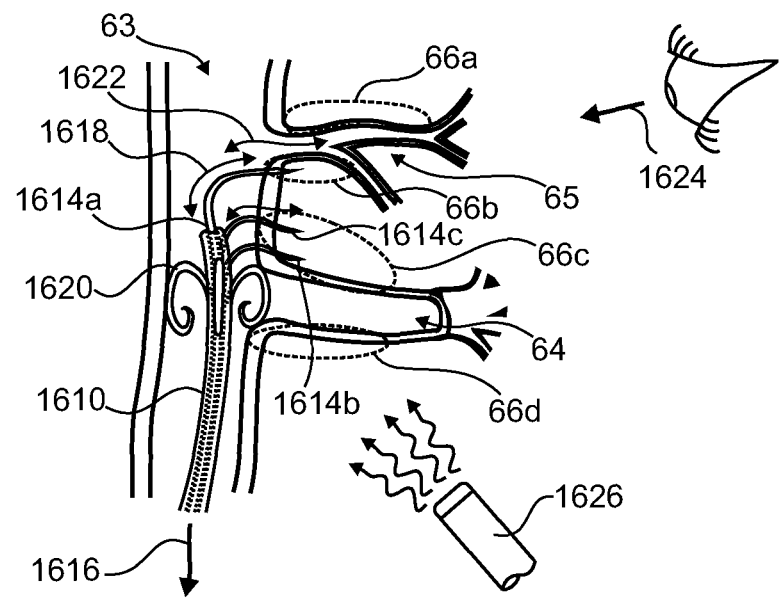
FIG. 16 shows aspects of a surgical tool in accordance with the present disclosure placed within a lumen under optional guidance from an imaging system.

FIG. 16 shows aspects of a distal tip of a surgical tool 1610 in accordance with the present disclosure placed within a lumen 63 optionally under guidance from an imaging system 1626 (e.g. an ultrasonic imaging probe, computer assisted imaging based computed tomography (CT), magnetic resonance imaging (MRI), positron emission tomography (PET), magnetoencephalography (MEG), functional MRI, stereotactic surgical system, or the like). A surgical tool 1610 including an elongate member 1612 and a plurality of probes 1614a-c, and optionally one or more stabilizing members 1620 each in accordance with the present disclosure is shown in FIG. 16, the elongate member 1612 positioned within the femoral artery 63, the stabilizing members 1620 deployed so as to maintain the position of the elongate member 1612 in the artery 63, while the probes 1614a-c have been deployed 1618 through the artery wall towards one or more regions of target tissue 66a-d. In aspects, one or more probes 1614a-c may be directed towards one or more nerve bundles in the vicinity of a primary target vessel 64 (e.g. a renal artery, or the like), others may be directed towards target tissue in the vicinity of an ancillary target vessel 65 (e.g. an additional renal artery, ancillary vessel, or the like), while others may be directed towards a ganglion or a nearby neural body. FIG. 16 shows a first probe 1614a positioned so as to analyze, stimulate, and/or treat target tissues 66b in the vicinity of an ancillary vessel 65, while a second probe 1614b and third probe 1614c are positioned so as to monitor, analyze, stimulate, and/or treat target tissues 66c in the vicinity of a primary vessel 64.

In aspects, the probes 1614a-c may be guided towards the target tissues 66a-d with the help of an imaging modality 1624 in accordance with the present disclosure. In the non-limiting example shown, the probes 1614a-c may be guided towards the target tissue 66a-d with the help of an ultrasound imaging system 1626. Alternatively, additionally, or in combination one or more probes 1614a-c may include one or more radiopaque materials and/or marker bands. Such bands may be advantageous for assisting with alignment of the probe with the target tissues, locating the probe with reference to the adjacent anatomical features around the surgical site, etc.

One or more of the elongate member 1612, stabilizing member 1620, probes 1614a-c, and/or associated electrodes thereupon may be coupled with the control end 1616 of the surgical tool 1610 (e.g. via the elongate member 1612).

In aspects, one or more of the probes 1614a-c, and/or elongate member 1612 may be directed 1622 into the ancillary vessel 65 as part of a diagnostic, monitoring, and/or treatment procedure. In aspects, a method in accordance with the present disclosure may include treating a primary vessel 64 and an ancillary vessel 65. In aspects, a method in accordance with the present disclosure may include sensing electrophysiological activity in the vicinity of the primary vessel 64 and/or ancillary vessels 65 to determine the need for a treatment, the extent of a treatment, etc.

In aspects, one or more probes 1614*a-c* in accordance with the present disclosure may be shaped and dimensioned such that it can be advanced 1622 into one or more ancillary vessels 65 during a procedure. In aspects, the probe 1614*a-c* may be less than 1.5 mm in diameter, less than 1 mm in diameter, less than 0.75 mm in diameter, less than 0.5 mm in diameter, or the like so as to freely enter into the ancillary vessel 65.

Figure 17:
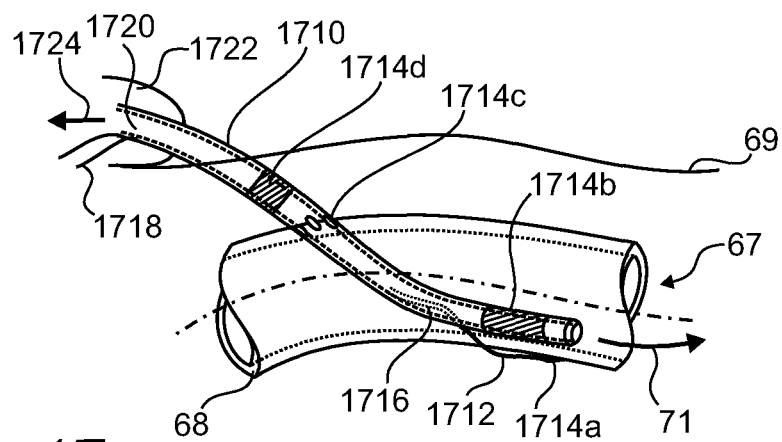
FIG. 17 shows aspects of a system for monitoring electrophysiological signals in the wall of a lumen in accordance with the present disclosure.

FIG. 17 shows aspects of a system for monitoring electrophysiological signals in the wall 68 of a lumen 67 in accordance with the present disclosure. In aspects, one or more probes 1712 in accordance with the present disclosure may be embedded into a sheath introducer. The sheath introducer may include a cannula 1710, along which electrical wiring 1718 and/or one or more of the probes 1712 may be arranged. The cannula 1710 may include one or more channels 1716 to accommodate one or more of the probes 1712, electrical wiring, or the like. The cannula 1710 may include one or more electrode bands 1714*b,d* and/or microelectrodes 1714*c*, configured for measurement within the wall 68 of the lumen 67, and/or for use as reference electrodes. The sheath introducer may include an embedded circuit and/or connector for interfacing with one or more of the electrodes 1714*a-d*, probes 1712, etc.

In aspects, one or more of the probes 1712 may include one or more electrodes 1714*a* in accordance with the present disclosure.

In aspects, one or more probes 1712 may be inserted into the lumen 67 of the subject, one or more of the probes 1712 may be inserted into the wall 68 of the lumen. In aspects, one or more of the probes 1712 may be anchored to the lumen wall 68, and/or one or more readings may be made from an electrode 1714*a* situated on the probe 1712 and/or on the cannula 1710 of the sheath introducer, to assist with placement, to read electrophysiological activity from the wall 68 of the lumen (i.e. to read activity within the smooth muscle of the media of the lumen wall), etc.

As part of a surgical procedure, the sheath introducer may be placed into the lumen 67 of a vessel through a skin 69 of a subject. The sheath introducer may provide a path for additional surgical tools to be introduced into the lumen 67 and progressed 71 there along to a surgical site (optionally remotely positioned from the entry point into the lumen). In aspects, one or more surgical tools (guidewires, catheters, balloon catheters, ablation catheters, etc.) may be introduced into the lumen 67 of the vessel via the sheath introducer.

In aspects, the sheath introducer may include a housing 1722 for placement against the skin 69 of the subject. The housing 1722 may include a valve coupling 1724 connected to the channel 1720 within the cannula 1710 of the sheath introducer, through which one or more tools may be advanced, removed, or exchanged during a surgical procedure. In aspects, the housing 1722 may include one or more connectors for interfacing electrically and/or mechanically with one or more of the electrical wiring 1718, electrodes 1714*a-d*, the probe 1712, or the like. In aspects, the connector may include an actuation mechanism (e.g. a sliding mechanism, a rotary mechanism, etc.), movement of which may be used to deploy the probe 1712 from within the channel 1716 into the lumen wall 68.

Such a configuration may be advantageous for use during a surgical procedure, to monitor electrophysiological activity from the vessel, for monitoring of smooth muscle activity before, during, and/or after the procedure, etc. Such a configuration may be advantageous for conveniently monitoring such activity while providing an access port for one or more of the surgical tools introduced during the procedure.

Figure 18:
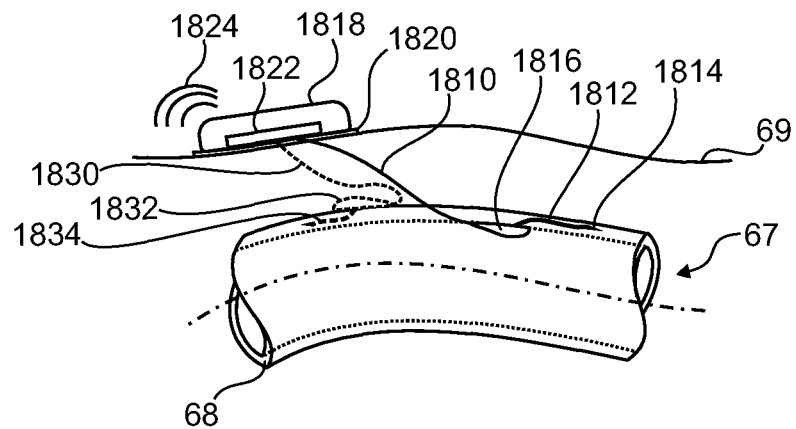
FIG. 18 shows aspects of wireless monitor placed within a lumen in accordance with the present disclosure.

FIG. 18 shows aspects of wireless monitor, a portion of which is configured to be placed within a lumen 67 in accordance with the present disclosure. The wireless monitor includes a power source, transceiver, and microcircuit 1822 coupled together within a housing 1818. The housing 1818 may include an adhesive 1820 or connector suitable for bonding it to the skin 69 of a subject during use. The wireless monitor may include or include means for coupling to an elongate member 1810 suitable for introduction into a subject, the elongate member 1810 having a control end (i.e. an end for coupling to the circuit 1822) and a distal tip (i.e. an end for insertion into a subject). The elongate member 1810 may include one or more probes 1812 in accordance with the present disclosure. The probes 1812 may be coupled to the elongate member 1810 yet deployable there from into a region of tissues adjacent thereto.

In aspects, upon placement, the elongate member 1810 may be inserted into the lumen 67 of a subject and biased towards the wall 68 thereof. One or more probes 1812 may be deployed from the elongate member 1810 and protrude into the wall 68 of the lumen 67 to interface with the tissues therein. The elongate member 1810 may include a probe clip 1816, configured so as to house at least a portion of the probe 1812 during placement, the probe clip 1816 optionally including a deployment mechanism (i.e. a mechanism for ejecting at least a portion of the probe 1812 into the lumen wall 68). Some non-limiting examples of deployment mechanisms include latch mechanisms, fuse locked mechanisms, retractable release mechanisms, electroactive material actuation mechanisms, combinations thereof, and the like. The probe 1812 may include one or more electrodes 1814, each electrically coupled to the circuit 1822 with one or more leads, wires, or the like through the elongate member 1810, wirelessly, or the like. In aspects, the elongate member 1810 may be retractable after placement (i.e. configured so that the elongate member may be slide past the leads, probes, probe clip, etc. and be removed from the subject).

In aspects, the wireless monitor may be configured to relay 1824 a physiological signal from the subject, an electrophysiological signal monitored via the probe and/or electrode to a base station, a phone, a relay, a wireless hub, a WiFi network, a cellular network, a controller, combinations thereof, or the like.

In aspects, the probe clip 1816 may include an embedded circuit in accordance with the present disclosure coupled with the probe 1814 and optionally with the circuit 1822 via the elongate member and/or a wireless connection.

In aspects, one or more probes 1812 in accordance with the present disclosure may include a delivery mandrel (e.g. a wire core, a needle core, etc.) configured within a flexible sheath (e.g. a soft sheath, a polymer sheath, etc.), the sheath optionally including one or more electrodes, or the like. Upon placement in the lumen wall, the delivery mandrel may be subsequently removed, leaving the flexible sheath in place for purposes of monitoring. Furthermore, the channel left by the vacated mandrel may be advantageous for fluid delivery/sampling to/from the tissue site near the tip of the probe. In aspects, the sheath may include one or more lead wires to electrically interface one or more of the electrodes with a circuit, controller, connector, or the like.

FIG. 18 also shows an alternative placement position for an elongate member 1830, a probe clip 1832, and a probe 1834 in accordance with the present disclosure. Such an alternative placement may be advantageous for positioning the probe 1834 within the lumen wall 68 without passing through the lumen 67 of the vessel.

Figure 19:
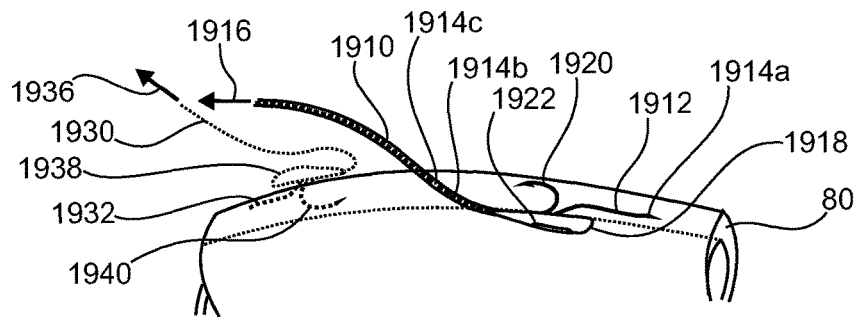
FIG. 19 shows aspects of a system for monitoring electrophysiological signals in the wall of a lumen in accordance with the present disclosure.

FIG. 19 shows aspects of a system for monitoring electrophysiological signals in the wall 80 of a lumen of a vessel in accordance with the present disclosure. The system may be coupled with a controller 1916, 1936, an external circuit, a wireless monitor, combinations thereof, and the like. The system may include an elongate member 1910, a probe clip 1918, and/or one or more probes 1912, each in accordance with the present disclosure. The system may include one or more electrodes 1914a-c, oriented along the walls, faces, tips, of the elongate member 1910, probe clip 1918, and/or probes 1912.

In aspects, the system may include an anchor 1920, coupled to the probe clip 1918, configured so as to intimately mate the probe clip 1918 to the lumen wall 80 during a placement procedure and/or a monitoring session. The anchor 1920 may be configured so as to deploy from the probe clip 1918 during a release procedure. The anchor 1920 may include one or more electrodes in accordance with the present disclosure. The anchor 1920 may include one or more electrically conducting materials suitable for interfacing with an adjacent tissue surface. In aspects, at least a portion of the anchor 1920 may serve as a reference electrode.

Some non-limiting examples of deployment mechanisms used to facilitate a deployment feature (i.e. of the anchor and/or one or more probes) include latch mechanisms, fuse locked mechanisms, retractable release mechanisms, electroactive material actuation mechanisms, combinations thereof, and the like. The probe 1912 may include one or more electrodes 1914a, each electrically coupled to the circuit 1916, 1936 with one or more leads, wires, or the like. In aspects, the elongate member 1910 may be retractable after placement (i.e. configured so that the elongate member 1910 may slide past the leads, probes, probe clip, etc. and be removed from the subject).

The probe clip 1918 may include one or more sensors 1922 for collecting information within the lumen during a monitoring session. The probe clip 1918 may include a pressure sensitive diaphragm (e.g. a hermetically sealed MEMs sensor, a differential gauge sensor, etc.), a flow sensor, a pH sensor, an analyte monitor (e.g. an oxygen sensor, carbon dioxide sensor, etc.). The sensor 1922 may be electrically coupled to one or more circuits 1916, 1936, controllers, embedded circuits, etc.

The elongate member 1910 may include one or more cuff electrodes 1914c, and/or one or more microelectrodes 1914b which may be coupled with the circuit 1916, 1936 and/or one or more probe electrodes 1914a, one or more sensors 1922, or the like.

FIG. 19 also illustrates an alternative placement position for the system wherein a probe clip 1938 is positioned outside of the lumen wall 80, while the probe 1932 and anchor 1940 are deployed into the lumen wall 80. One or more elements within the probe clip 1938, the probe 1932, the anchor 1940, and/or the elongate member 1930 may be coupled with a circuit 1936 via the elongate member 1930.

Figure 20A:
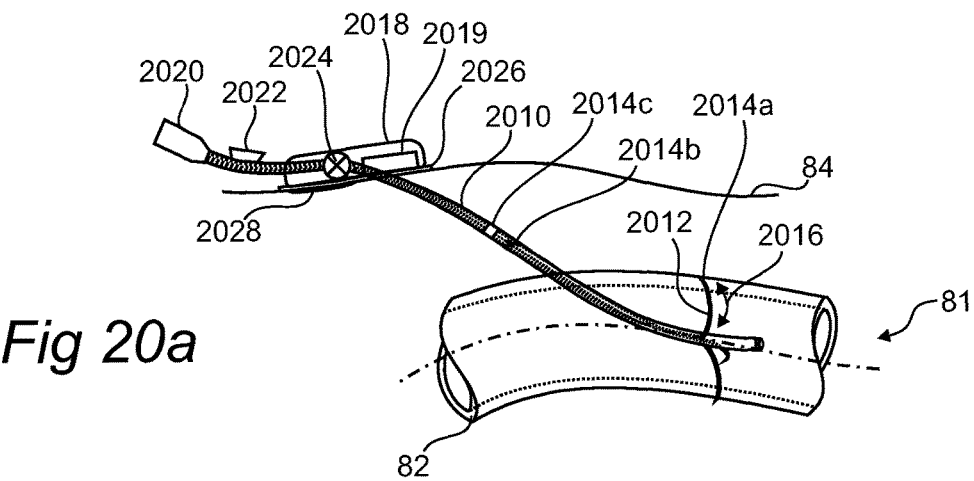
FIGS. 20a-c show aspects of monitoring devices in accordance with the present disclosure.
Figure 20B:
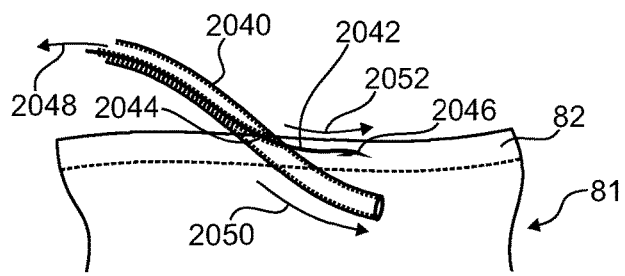
Figure 20C:
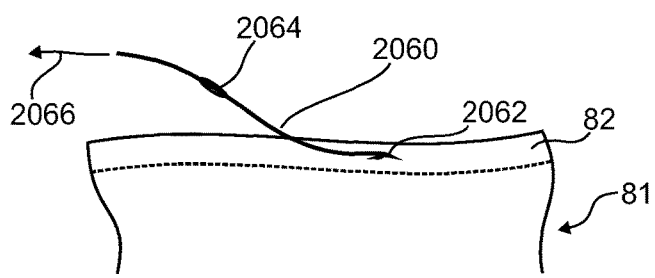

FIGS. 20a-c show aspects of monitoring devices in accordance with the present disclosure. FIG. 20a shows aspects of an intravenous catheter, infusion set, and/or intra-arterial catheter with one or more embedded probes 2012 each in accordance with the present disclosure. The monitoring device may include a cannula 2010 (i.e. an elongate member in accordance with the present disclosure) for fluid communication between an externally placed port 2020 and the interior of a lumen 81 into which it may be placed. The monitoring device may include one or more probes 2012 coupled to the cannula 2010, each probe including one or more electrodes 2014a and/or fluid delivery means in accordance with the present disclosure. One or more of the probes 2012 may be integrated into the cannula 2010 (i.e. at least a portion of which is contained within one or more lumens oriented around the wall of the cannula 2010, etc.). The monitoring device may include one or more sliding mechanisms 2022, located along the exterior thereof, configured so as to slidingly deploy 2016 one or more of the probes 2012 from the cannula 2010 into the walls 82 of the lumen 81 of the vessel during use. The probes 2012 may include one or more electrodes 2014a in accordance with the present disclosure. The electrodes 2014a may be electrically coupled to a connector 2020, a wireless monitor, a circuit 2019, etc.

The monitoring device may include a power source, transceiver, and microcircuit 2019 coupled together within a housing 2018. The housing 2018 may include an adhesive 2026 or connector suitable for bonding it to the skin 84 of a subject during use. In aspects, the monitoring device may include a reference electrode 2028 coupled to the housing 2018 and interfacing with the skin 84 of a subject upon attachment thereon.

The monitoring device may include a valve 2024 for controlling fluid coupling between the port 2020 and the cannula 2010. The cannula 2010 may include one or more electrodes 2014c,d in accordance with the present disclosure.

FIG. 20b shows aspects of a monitoring device in accordance with the present disclosure. The monitoring device includes an elongate member 2040 and a probe 2042 slideably coupled thereto. The elongate member 2040 may be placed 2050 within a lumen 81 within a body and the probe 2042 deployed 2052 so as to extend past the limits of the elongate member 2040 and enter the wall 82 of the lumen and/or surrounding tissue. In aspects, the probe 2042 may include one or more barbs 2046, biodegradable barbs, etc. configured so as to fixate the probe 2042 within the tissue after deployment. Upon placement of the probe 2042, the elongate member 2040 may be retracted and removed 2048 from the body (while leaving the probe 2042 in place). The probe 2042 may include one or more electrodes 2046 in accordance with the present disclosure. The elongate member may include a slot, a break-away region, etc. in order to facilitate sliding over the probe during the retraction process. The probe 2042 may be deliverable along a channel or conduit 2044 included in the elongate member 2040. In aspects, the elongate member 2040 may include a central lumen to facilitate the passage of a guidewire, an insertion needle, or the like there through as part of a placement procedure.

The probe 2042 may include a connector, an embedded circuit, etc. each in accordance with the present disclosure, electrically coupled to one or more electrodes 2014a thereupon in order to facilitate monitoring of electrophysiological activity during a monitoring session.

FIG. 20c shows aspects of a monitoring device in accordance with the present disclosure. The device is shown in a monitoring state after the elongate member has been retracted from the probe 2060. The probe 2060 may be configured so as to be a soft lead (e.g. a polymer, elastomeric conducting element, spring-like element, etc.), configured so as to minimize tissue trauma during a long term monitoring session. The probe 2060 may include one or more barbs 2062 to retain the position of the probe tip after placement within a body. The probe 2060 may include one or more reference electrodes along the length thereof. The electrodes 2062 (i.e. shown collocated with the barb 2062) may be coupled to a circuit 2066, a controller, an embedded circuit 2064, or the like in order to facilitate monitoring therefrom after placement.

Figure 21:
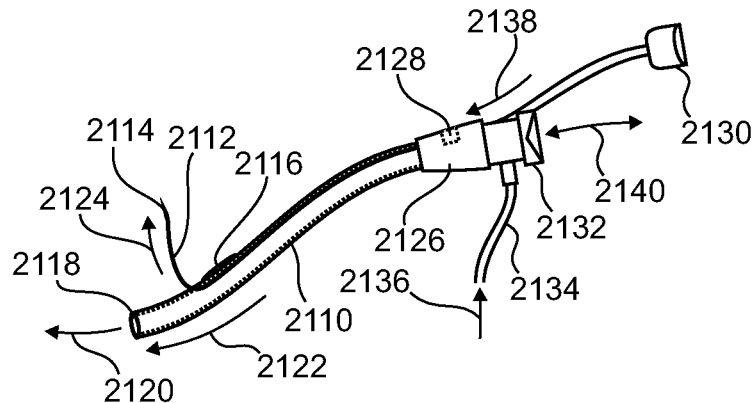
FIG. 21 shows aspects of a system embedded into a sheath introducer in accordance with the present disclosure.

FIG. 21 shows aspects of a system embedded into a sheath introducer 2110 in accordance with the present disclosure. The sheath introducer 2110 includes an introducer needle (not shown) configured so as to penetrate the wall of a lumen and to insert 2112 the sheath 2110 into the lumen before being refracted therefrom, leaving the sheath 2110 in place within the lumen. The sheath 2110 may be connected to a manifold 2126, optionally including a valve 2132 (e.g. a 1-way valve, a flexible valve, a duck bill valve, etc.) for insertion/removal 2140 of surgical tools, etc. through the sheath 2110 and into the lumen 2120. The manifold 2126 may include channels for directing flow there through, the channels coupled to the sheath 2110, the valve 2132, optionally a flood line 2134, etc. The sheath 2110 may include one or more probes 2112 in accordance with the present disclosure. The probes 2112 may be configured to couple with the sheath 2110 along one or more lumens in the walls thereof. The probes 2112 may include one or more electrodes 2114, electrically coupled to a cable, a connector 2130, and/or an embedded circuit 2128 (i.e. embedded into the manifold). The probes 2112 may be slidingly deployed 2124 from the sheath 2110 in order to penetrate the lumen wall and access target tissues there beyond (e.g. muscle, smooth muscle, nerves, neural bodies, etc.). The manifold 2126 may include a sliding mechanism 2138, and optionally a locking mechanism to ensure that the probes 2112 are not over extended during deployment, to control the extent of the deployment, etc. The flood line 2134 may connect to a valve, an inlet port, etc. In aspects, the introducer may include an embedded circuit 2128 in accordance with the present disclosure may include one or more amplifiers, one or more switch networks, an analog to digital converter, a communication module, or the like coupled with one or more of the sheath 2110, probes 2112, electrodes 2114, 2116, or the like. In aspects, the introducer may include a connector 2130 coupled with the embedded circuit 2128, the sheath 2110, probes 2112, electrodes 2114, 2116, or the like to convey signals therefrom as part of a diagnostic, monitoring, and/or therapeutic procedure in accordance with the present disclosure.

In aspects, the sheath 2110 may include a tapered tip 2118 to assist with ease of insertion into the lumen of a vessel. One or more fluids may be delivered 2136 to the lumen via the flood line 2134. Some non-limiting examples of fluid include contrast agent, medicament, a hydrating agent, saline, etc.

Figure 22:
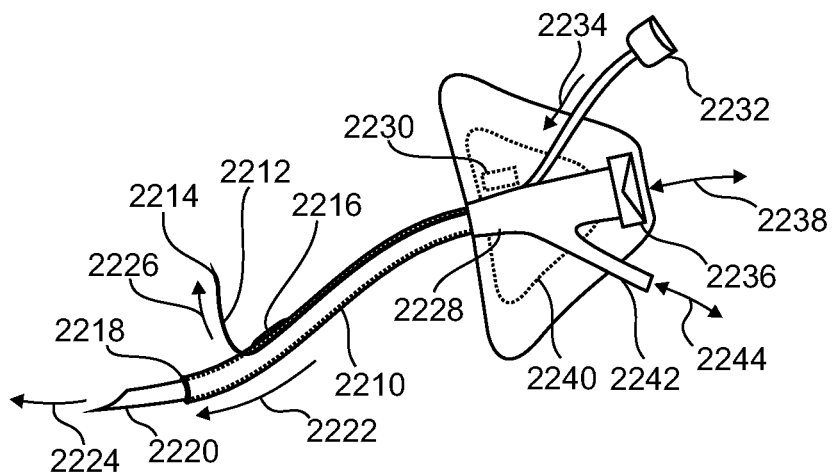
FIG. 22 shows aspects of a system integrated into an IV catheter in accordance with the present disclosure.

FIG. 22 shows aspects of a system integrated into an intravenous catheter, intra-arterial catheter, and/or infusion set in accordance with the present disclosure (herein referred to as an IV catheter). The IV catheter includes an introducer needle 2220 configured so as to penetrate the wall of a lumen and assist with insertion 2222 of a cannula 2210 into the lumen before being retracted therefrom, leaving the cannula 2210 in place within the lumen. The cannula 2210 may be connected to a manifold 2228, optionally including a valve 2236 (e.g. a 1-way valve, a flexible valve, a duck bill valve, etc.) for inserting/removing 2238 tools, needles, etc. into/out of 2224 the lumen. The manifold 2228 may include one or more channels for directing flow there through, the channels coupled to the cannula 2210, the valve 2238, optionally a flood line 2242 (i.e. for delivery/sampling 2244 of fluids therefrom), etc. The cannula 2210 may include one or more probes 2212 in accordance with the present disclosure. The probes 2212 may be configured to couple with the cannula 2210 along one or more lumens arranged within the walls thereof. The probes 2212 may include one or more electrodes, electrically coupled to a cable, a connector 2232, and/or an embedded circuit 2230 (i.e. embedded into the manifold). The probes 2212 may be slidingly deployed 2226 from the cannula 2210 in order to penetrate the lumen wall and access target tissues there beyond (e.g. muscle, smooth muscle, nerves, neural bodies, etc.). Such deployment 2226 may be facilitated by means of a sliding mechanism 2234 within the manifold 2228, such as may be achieved by advancing the connector 2232 towards the manifold 2228. The manifold 2228 may include a locking mechanism coupled to the probes 2212 to ensure that the probes 2212 are not over extended during deployment 2226 or accidently retracted therefrom, to control the extent of the deployment, to lock the probes 2212 into place after deployment, etc. The flood line 2242 may connect to a valve, an inlet port, etc. The embedded circuit 2230 in accordance with the present disclosure may include one or more amplifiers, one or more switch networks, an analog to digital converter, a communication module, or the like to communicate signals from one or more electrodes 2214, 2216, from a probe 2212, the cannula 2210, an embedded sensor, or the like.

In aspects, the IV catheter may include an adhesive patch 2240 for connecting the manifold 2228 to a tissue surface during use. The adhesive 2240 may be electrically and/or ionically conducting so as to provide a reference electrode during use. The reference electrode may be electrically coupled to the embedded circuit 2230 and/or connector 2232.

In aspects, the IV catheter may include a wireless monitoring circuit in accordance with the present disclosure to communicate one or more signals generated by an onboard circuit 2230 to a base station, a phone, a relay, a wireless hub, a WiFi network, a cellular network, a controller, combinations thereof, or the like. Such a configuration may be advantageous for coupling the monitoring system with a therapeutic device, for chronic monitoring of sympathetic nerve activity, muscular sympathetic nerve activity, combinations thereof, or the like.

In aspects, the sheath 2210 may include a tapered tip 2218 to assist with ease of insertion into the lumen of a vessel.

Figure 23A:
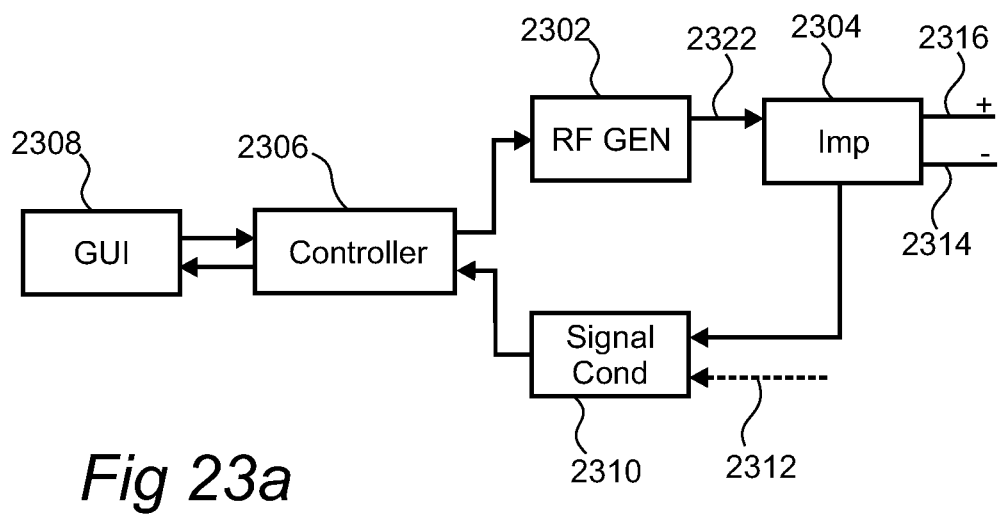

FIGS. 23a-e show schematics of aspects of controllers and control circuits in accordance with the present disclosure. FIG. 23a shows a schematic of aspects of a controller configured to apply a radiofrequency current to one or more probes in a system in accordance with the present disclosure. The controller includes a control block 2306, including a processor, coupled to a graphical user interface 2308 to communicate with a user (e.g. a surgeon, a technician, a nurse, etc.). The control block 2306 may also be coupled to an RF generator 2302 and a signal conditioning unit 2310. The RF generator 2302 may be configured to form one or more signals 2322 for stimulating and/or treating one or more tissue sites in a subject via one or more probes connected thereto based upon commands from the control block 2306. The RF generator 2302 may be coupled to a signal monitoring block 2304 (an IV block), the IV block 2304 may be configured to monitor current, voltage, and/or one or more properties related thereto (e.g. DC conductance, impedance, impedance spectra, approximate impedance model, etc.) during a signal delivery process (i.e. along the lines 2314, 2316 coupling the controller to the surgical tool). In aspects, the RF generator 2302 and/or the IV block 2304 may be configured to apply a test signal to one or more probes and/or between one or more probes and an external electrode, an elongate member electrode, a reference electrode, etc. in order to determine impedance there between.

In aspects, the signal conditioning unit 2310 may be configured to monitor one or more electrophysiological signals from one or more probes in the system 2312, to accept one or more signals from the IV block 2304, and/or to relay such information or signals derived therefrom to the control block 2306.

Figure 23B:
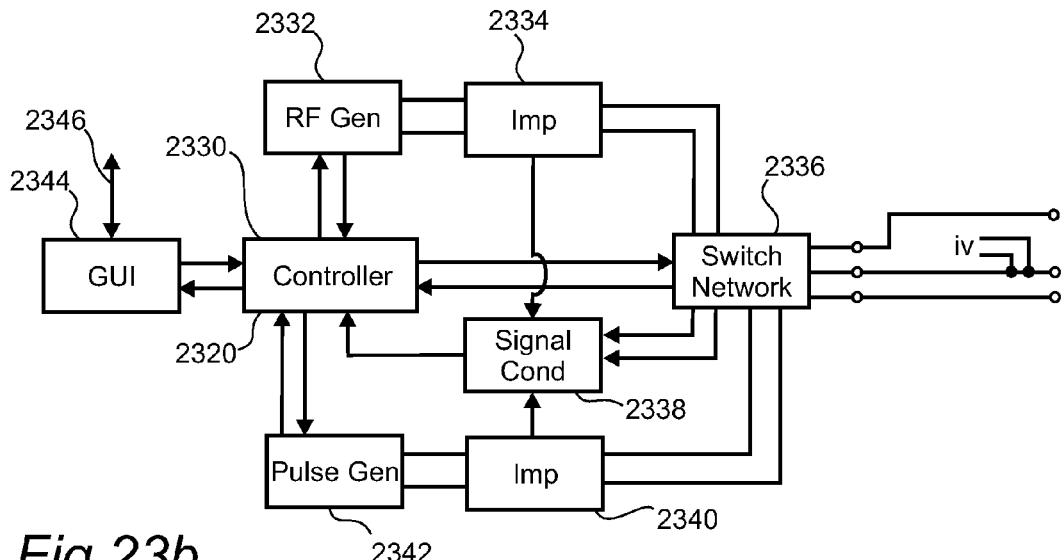

FIG. 23*b* shows a schematic of aspects of a controller in accordance with the present disclosure. The controller includes a control block 2330, including a processor, coupled to a graphical user interface 2344 to communicate with a user 2346 (e.g. a surgeon, a technician, a nurse, etc.). The control block 2330 may also be coupled to an RF generator 2332, a pulse generator 2342, and/or a signal conditioning unit 2338. The RF generator 2332 may be configured to form one or more signals for stimulating and/or treating one or more tissue sites in a subject via one or more probes connected thereto based upon commands from the control block 2320. In aspects, the RF generator 2332 may be coupled to a signal monitoring block 2334 (an IV block). The IV block 2334 may be configured to monitor current, voltage, and/or one or more properties related thereto of the signals delivered to a switch network 2336 or a surgical tool in accordance with the present disclosure (e.g. DC conductance, impedance, impedance spectra, approximate impedance model, etc.) during a signal delivery process. In aspects, the RF generator 2332 and/or the IV block 2334 may be configured to apply a test signal, a switch network 2336, to one or more probes and/or between one or more probes and an external electrode, an elongate member electrode, a reference electrode, etc. in order to determine impedance there between.

The pulse generator 2342 may be configured to form a stimulating train of pulses to be delivered to one or more probes and/or electrodes in the system. In aspects, one or more electrical characteristics of the pulses (e.g. current, voltage, electrode to electrode impedance, etc.) may be monitored by a pulse IV block 2340 included in the controller and optionally conveyed to the signal conditioning block 2338.

In aspects, the controller may include a switch network 2336, isolation unit, or the like. In the non-limiting example shown in FIG. 23*b*, the switch network 2336 may be configured to direct signal traffic (e.g. outgoing signals, pulses, radiofrequency currents, incoming signals, monitored signals, electrophysiogical signals, etc.) to one or more blocks in the controller and/or one or more probes, electrodes, sensors, etc. included in an associated surgical tool in accordance with the present disclosure. In aspects, the switch network 2336 may be configured via commands sent by the control block 2320.

In aspects, the controller may include an isolation unit, configured to maintain a safe isolation level between aspects of the system in contact with the subject, the user, etc. and the circuits within the controller.

In aspects, the signal conditioning unit 2338 may be configured to monitor one or more electrophysiological signals from one or more probes, electrodes, sensors, etc. included in the system, to accept one or more signals from the IV block 2340 and to relay such information or signals derived therefrom to the control block 2330 for recording, display, integration into a feedback control algorithm, etc.

Figure 23C:
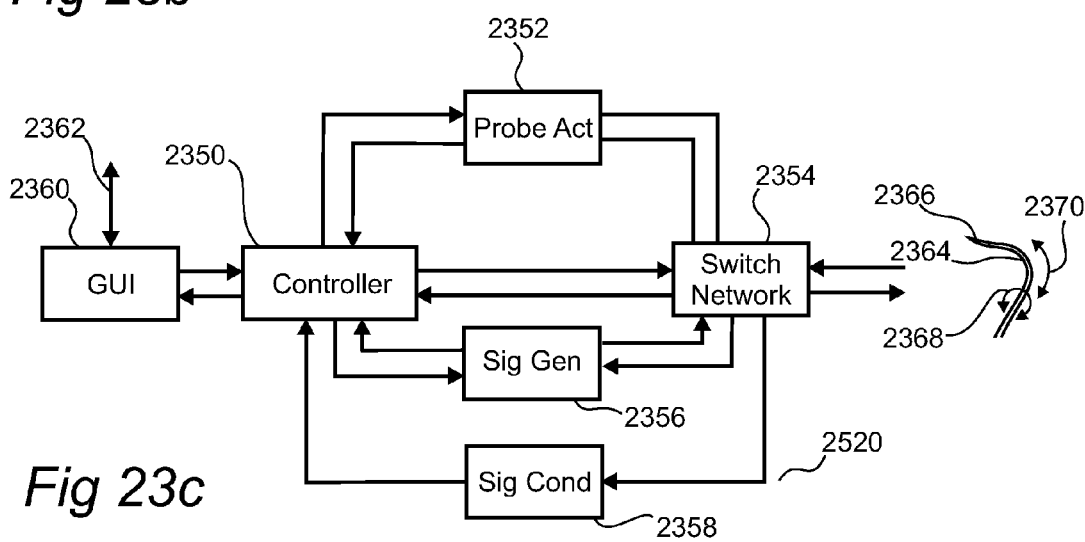

FIG. 23*c* shows a schematic for aspects of a controller in accordance with the present disclosure configured to automatically, semi-automatically, or robotically actuate one or more aspects of a system in accordance with the present disclosure during a procedure. The schematic shows a control block 2350 coupled to a probe actuation block 2352, the probe actuation block 2352 configured to communicate, receive commands, send updates, etc. to/from the control block 2350 and to controllably actuate one or more probes 2364 (e.g. advance/retract 2370, bend, torque 2368, bias, etc.) and/or elongate member (e.g. advance, retract, actuate the tip thereof, scan, bias one or more regions towards a wall, etc.), or the like. In aspects, the actuation block 2352 may be configured to automatically deploy one or more probes 2364 from an associated elongate member during a procedure. In aspects, the system may include an imaging modality in accordance with the present disclosure to provide feedback for the controller, user 2362 (e.g. via a graphical user interface 2360, a haptic interface, etc.), and/or actuation block 2352 during a procedure.

A signal generator 2356, coupled to the control block 2350 and an optional switch network 2354 may be configured to form a stimulating train of pulses, a radiofrequency signal, etc. to be delivered to an optional switch network 2354, one or more probes 2364, and/or electrodes 2366 in the system. In aspects, one or more electrical characteristics of the pulses and/or RF signal (e.g. current, voltage, electrode to electrode impedance, etc.) may be monitored by an IV block included in the controller (not explicitly shown).

In aspects, the controller may include a switch network 2354, an isolation unit, or the like. In the non-limiting example shown in FIG. 23*c*, the switch network 2354 may be configured to direct signal traffic (e.g. outgoing signals, pulses, radiofrequency currents, incoming signals, monitored signals, electrophysiogical signals, etc.) to one or more blocks in the controller, the probes 2364, an external electrode, etc. In aspects, the switch network 2354 may be configured via commands sent by the control block 2350.

In aspects, the controller may include an isolation unit, configured to maintain a safe isolation level between aspects of the system in contact with the subject, the user, etc. and the circuits within the controller.

In aspects, a signal conditioning unit 2358 may be included in the controller, and may be configured to monitor one or more electrophysiological signals from one or more probes 2364, and/or electrodes 2366 in the system, to accept one or more signals from an associated IV block, and/or to relay such information or signals derived therefrom to the control block 2350.

Figure 23D:
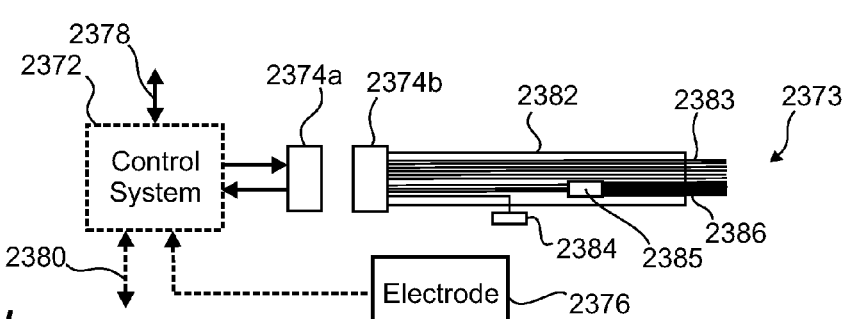

FIG. 23*d* shows a schematic of aspects of a controller 2372 and a surgical tool 2373 in accordance with the present disclosure. The controller 2372 may be configured so as to communicate information with and/or receive commands from a user 2378, optionally to interface with one or more additional physiological measurement systems 2380 (e.g. blood pressure monitor, an electrocardiograph, flow sensor, ultrasound probe, etc.) for use in a procedure in combination with a system in accordance with the present disclosure. The controller 2372 may be coupled to a connector 2374*a* to communicate with the surgical tool 2373 (e.g. communicate electrically and/or mechanically, actuate one or more aspects of the surgical tool through a mating connector 2374*b*, etc.).

In aspects, the surgical tool 2373 may include a matching connector 2374*b*, one or more probes 2383, 2386 housed into an elongate member 2382, an embedded circuit 2385 coupled to one or more probes 2386, one or more electrical interconnects provided there through, one or more electrodes 2384 on the elongate member 2382, combinations thereof, or the like.

The controller 2372 may also be coupled to or include connectors for connection to one or more external electrodes 2376 (e.g. patch electrodes, electrodes for placement elsewhere within a body, etc.).

FIG. 23*e* shows a schematic of aspects of a controller in accordance with the present disclosure including a fluid delivery system. The controller may include a control block 2388 in accordance with the present disclosure coupled to a graphical user interface 2396 for conveying information to a user 2397 and/or receiving commands therefrom. The control block 2388 may be coupled to a pump/valve assembly 2390, which may in turn be coupled to a reservoir 2392 for storing a chemical agent, and/or for receiving a sample from a coupled surgical tool in accordance with the present disclosure. The reservoir 2392 may be connected 2393 to one or more probes in accordance with the present disclosure equipped with channels suitable for communication of fluid there through.

In aspects, the controller may include a signal conditioning unit 2394 coupled to the control block 2388. The signal conditioning unit 2394 may be coupled 2395 to one or more of the probes to monitor one or more aspects thereof.

In aspects, the pump/valve assembly 2390 may include one or more sensors configured to determine and/or control a volume of bolus delivered to a probe, a pressure delivered to the probe, a state of a valve, etc. to be communicated back to the control block 2388 during use.

FIGS. 24*a*-*b* show aspects of methods for treating target tissues in accordance with the present disclosure.

FIG. 24*a* shows aspects of a method for treating a target tissue including accessing the target tissue 2410, monitoring 2415 one or more electrophysiological signals from at least a region of the target tissue and assessing if the ranges are normal or abnormal. If the ranges are normal, access an alternative region of the target tissues and monitor again, or abort the procedure 2425. Optionally, if the electrophysiological activity is abnormal, perform a treatment 2420 in the vicinity of the tissue (e.g. stimulate, ablate, administer a chemical, etc.). Optionally, after performing a treatment, the region of the target tissue may be monitored 2430 once again to determine the electrophysiological activity present and to determine if the levels are within the normal range, if a block has occurred, etc. (i.e. a successful outcome 2440), or if the signals are still abnormal and require further treatment, alternative treatment 2435, or the like.

In aspects, the method may include testing another region of the target tissue, treating one or more regions of the target tissue, including one or more steps from a method in accordance with the present disclosure, performing any step of the procedure with a system in accordance with the present disclosure, or the like.

FIG. 24*b* shows aspects of a method for treating a target tissue including generally accessing the target tissue 2450, and testing 2455 at least a region of the accessed tissue with a stimulus in accordance with the present disclosure, while monitoring the response thereof. If the response to the stimulus indicates that the accessed tissue is not the intended target of the therapy (e.g. if the local receptors do not respond to the stimulus, the local receptors respond within a normal range to the stimulus, etc.), adjust the access site 2460, so as to interface with an alternative region of the target tissue, and retest. Once a suitable treatment site has been located 2457, continue with treatment in accordance with the method shown in FIG. 24*a* (indicated with the outline "block a") 2465.

Aspects of methods for performing a surgical, diagnostic, and/or monitoring procedure in accordance with the present disclosure are discussed herein.

In aspects, a method for addressing a surgical site on an organ in a body (e.g. a bowel wall, a stomach, a kidney, a pancreas, a prostate, a spleen, a liver, a bladder, a gland, an artery, a vein, a renal artery, etc.) is considered. The method may include, monitoring one or more local physiological signals (e.g. an evoked potential, a neurological activity, MSNA, EMG, MMG, sympathetic tonal change, etc.) in accordance with the present disclosure at one or more measurement locations within and/or along an outer wall of the organ/lumen to determine one or more reference signals; performing at least a portion of a surgical procedure (e.g. an ablation, an excision, a cut, a burn, an RF ablation, an abrasion, a biopsy, delivery of a substance, etc.) in accordance with the present disclosure at or near to one or more surgical locations (e.g. proximal, distal, remotely therefrom, and/or collocated with one or more of the measurement locations); monitoring one or more local physiological signals at one or more of the measurement locations to determine one or more updated signals; and comparing one or more reference signals with one or more updated signals to determine an extent of completion for the surgical procedure.

In aspects, the method may include determining if the site is appropriate for performing the surgical procedure based upon the signals or metrics generated therefrom as measured during the step of monitoring. Such metrics may include electrophysiological activity, neural traffic, response of traffic to a stress test (i.e. to determine if the appropriate tissues are being addressed), comparing a shape of a frequency response of activity against a "normal" frequency response, comparing changes in a frequency response of activity against a response from one or more alternative locations in the body, etc.

In aspects, the extent of completion may be considered to include a change, reduction, and/or substantial elimination of at least a portion of one or more of the local physiological signals (e.g. reduction in amplitude of a frequency band, reduction in responsiveness, a change in a lag between measurement locations, a change in cross-talk between measurement locations, substantial elimination of the signal, etc.).

The step of monitoring to determine an updated signal may be performed before, during, and/or after the step of performing at least a portion of the surgical procedure.

The step of performing at least a portion of the surgical procedure may be repeated. Thus the method may be incrementally applied, so as to head towards completion in a stepwise process without excessive application of the surgical procedure.

The method may include waiting for a period of time after performing at least a portion of the surgical procedure. Monitoring may be performed during the waiting period, perhaps so as to determine a recovery period for the local physiological signal (i.e. a time period over which the local physiological signal recovers). Such a recovery period may be an indication of the extent of completion.

The method may include stimulating one or more stimulation locations (e.g. proximal, distal, remotely therefrom, and/or collocated with one or more of the measurement locations and/or the surgical locations, or the like). The step of stimulating may be coordinated with the step of performing at least a portion of the surgical procedure, and/or with the step of monitoring to determine a reference and/or updated signal. The stimulation may be provided in any form in accordance with the present disclosure. In aspects, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiological activity.

The method may include monitoring one or more remote physiological parameters in accordance with the present disclosure at a remote location (e.g. an alternative vessel, an organ, a ganglion, a nerve, etc.) substantially removed from the immediate vicinity of the vessel to determine an updated remote physiological signal and/or reference remote physiological signal.

In aspects, some non-limiting examples of remote physiological parameters that may be monitored during before, during, and/or after a procedure include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery, through an ancillary artery, etc.), a blood flow differential signal (e.g. a significantly abnormal and or sudden change in blood flow within a structure of the body, a vessel, an organ, etc.), blood perfusion (e.g. to an organ, an eye, a volume of tissue, etc.), a blood analyte level (e.g. a hormone concentration, norepinephrine, catecholamine, renine, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, carotid body, and/or related nervous system structures), combinations thereof, and the like.

The updated remote physiological signal and/or reference remote physiological signal may be combined and/or compared with one or more reference signals, and/or one or more updated signals in order to determine the extent of completion.

The method may include selecting a surgical location. The step of selection may depend upon one or more monitoring steps, proximity to an alternative surgical location (i.e. perhaps a previously treated surgical location, etc.).

In aspects, the steps of monitoring may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements, a time averaged comparison, a convolution, or the like.

In aspects, the method may include forming a topographical map from the one or more measurements (e.g. from one or more of the signals). The method may include determining a topographical map of physiological functionality in the vicinity of the surgical site derived from one or more of the physiological signals. The method may include updating the topographical map after the step of performing at least a portion of the surgical procedure.

In aspects, the method may include placement of a plurality of surgical tools, one or more surgical tools (i.e. a procedural tool) placed so as to access one or more of the surgical locations, and one or more surgical tools (i.e. a monitoring tool) placed so as to access one or more of the monitoring locations. In aspects, a procedural tool may be placed upon/near to a first organ (e.g. a bowel wall, a stomach wall, a kidney, a gland, a pancreas, a neural body, a carotid body, a renal artery, a left renal artery, etc.) and a monitoring tool may be placed upon/near to a second organ (e.g. an opposing renal artery, a neural body, a gland, a carotid body, a pancreas, a right renal artery, a femoral artery, an iliac artery, etc.). Thus, the monitoring tool may be used to monitor one or more of the measurement locations on the second organ. The procedural tool may be used to surgically treat one or more surgical locations on the first organ. Additionally, alternatively, or in combination, the procedural tool may monitor one or more monitoring locations on the first organ, perhaps in combination with monitoring performed on the second organ by the monitoring tool.

In aspects, the method may be performed with one or more surgical tools in accordance with the present disclosure.

One or more steps of monitoring may be performed with one or more probes and/or electrodes in accordance with the present disclosure.

One or more steps of performing at least a portion of the surgical procedure may be performed with one or more probes and/or electrodes in accordance with the present disclosure.

In aspects, of a method for RF ablating tissue in accordance with the present disclosure, the local tissue tone may be measured before, during, between individual RF pulses, and/or after a train of RF pulses. In aspects, as the local tissue tone changes during application of the RF pulses, the tonal changes may be used to determine the extent of the therapy. In aspects, as the RF ablation process may be applied to the adjacent tissues (perhaps via one or more probes), the tonal measurements (as determined by one or more probes equipped with a strain measurement sensor, perhaps the same probe through which the RF signal may be applied) may be monitored to determine an extent of completion of the procedure. Such an approach may be advantageous for performing such a procedure as the tonal measurement techniques may not be significantly affected by the local RF currents associated with the RF ablation procedure. The tonal measurements may be made at monitoring locations sufficiently far from the RF ablation zone such that the local tissues under measurement are not directly affected by the RF ablation process but may undergo a change in tone as a consequence of the RF ablation process.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A tool, comprising:
   an elongate member with a distal tip and a control end, the distal tip thereof shaped and dimensioned so as to fit within a lumen, the elongate member shaped and dimensioned so as to extend from an entry site on a body into the lumen; and
   one or more probes each configured with a probe tip, the probes deploy-ably coupled with the distal tip of the elongate member and at least one of electrically, mechanically, and fluidly coupled to the control end of the elongate member, the probe tips shaped so as to at least one of penetrate into and penetrate through a wall of the lumen upon deployment from the elongate member, one or more of the probes comprising one or more electrodes electrically coupled to the probes, one or more of the electrodes configured to at least one of convey a signal associated with an electrophysiological activity and to alter the electrophysiological activity upon deployment;

wherein the tool is configured for at least one of monitoring and altering electrophysiological activity within the vicinity of the lumen within the body; and a controller configured:
to record one or more electrophysiological signals from monitored electrophysiological activity within the vicinity of one or more of the electrodes coupled to the probes;
to cancel one or more movement artifacts from the recorded electrophysiological signals utilizing a corrective signal, the corrective signal being generated from monitoring one or more physiological parameters of the subject at a location remote from the vicinity of the one or more electrodes coupled to the probes.

2. The tool of claim 1, wherein the signal is an electrophysiological signal related to a water concentration, a tissue tone, an evoked potential, a remotely stimulated nervous activity, a sympathetic nervous activity, an electromyographic signal [EMG], a mechanomyographic signal [MMG], a local field potential, an electroacoustic event, a vasodilation, a vessel wall stiffness, a muscle sympathetic nerve activity, a central sympathetic drive, a nerve traffic, or combinations thereof.

3. The tool of claim 1 further comprises a microcircuit, wherein the one or more electrodes coupled to the probes are electrically coupled with the microcircuit, the microcircuit configured to condition the conveyed signal, and wherein the microcircuit is embedded into the tool and at least a portion of the electrical coupling is provided via the elongate member.

4. The tool of claim 1, wherein one or more of the probes comprises a microelectrode configured to interface with an adjacent tissue volume within or beyond the wall of the lumen, the microelectrode having an area of less than 5000 $\mu m^2$, less than 1000 $\mu m^2$, less than 250 $\mu m^2$, or less than 100 $\mu m^2$.

5. The tool of claim 1, further comprising one or more stimulating electrodes electrically and mechanically coupled to at least one or more of the probes and the elongate member, the stimulating electrodes configured to provide at least one of a stimulating current and an ablating current to a tissue site in the vicinity of the wall of the lumen.

6. The tool of claim 5, further comprising a plurality of stimulating electrodes, the tool configured to coordinate at least one of stimulating currents and ablating currents between two or more of the stimulating electrodes, the currents passing through the tissue site.

7. The tool of claim 5, wherein one or more of the probes comprises a channel, fluidly coupled with the control end of the elongate member, for delivering at least one of a diagnostic substance and a therapeutic substance to a tissue site in the vicinity of the wall of the lumen.

8. The tool of claim 7, wherein the one or more stimulating electrodes are configured and positioned so as to monitor at least one of: (i) the effect of at least one of the stimulating current and ablating current; and (ii) the effect of the substance, delivered to the tissue site in the vicinity of the wall via the channel, on at least one of the tissue site and tissues related thereto.

9. The tool of claim 5, wherein each of the one or more stimulating electrodes comprise an area of greater than 0.1 $mm^2$, 0.5 $mm^2$, 1 $mm^2$, 2 $mm^2$, or 10 $mm^2$.

10. The tool of claim 7, further comprising the at least one of the diagnostic substance and the therapeutic substance, wherein the at least one of the diagnostic substance and the therapeutic substance is selected from a chemical, a drug substance, a neuromodulating substance, a neuroblocking substance, an acid, a base, a denervating agent, or a combination thereof.

11. The tool of claim 7, further comprises a therapeutic substance, wherein the therapeutic substance is a selected from a neurotoxin, a botulinum toxin, a tetrodotoxin, a tetraethylammonium, a chlorotoxin, a curare, a conotoxin, a bungarotoxin, arsenic, ammonia, ethanol, hexane, nitric oxide, glutamate, resiniferatoxin, alcohol, phenol, capsaicin, an anesthetic, lidocaine, tetanus toxin, quaternary ammonium salts, a pachycurare, a leptocurare, acetylcholine, aminosteroids, or a combination thereof.

12. The tool of claim 7 further comprises a therapeutic substance, wherein the therapeutic substance is adapted to be comprised within a restraining matrix.

13. The tool of claim 1, wherein one or more of the probes is slidingly coupled to the elongate member, sliding of the probe along the length of the elongate member providing the deployment thereof.

14. The tool of claim 1, further comprising:
a stabilizing member coupled to the elongate member, the stabilizing member configured to retain the position of the distal tip of the elongate member within the lumen upon deployment;
wherein the stabilizing member is selected from a balloon, a basket, a plurality of flexible members, a wire cage, an embolic filter, or a combination thereof; and
wherein the stabilizing member comprises one or more electrodes, configured to provide at least one of a stimulating current and an ablating current to the wall of the lumen.

15. The tool of claim 1, wherein one or more of the probe tips is shaped with a curved probe tip, and is slidingly and rotate-ably coupled with the control end of the elongate member, so as to be steerably advanced through the wall of the lumen upon deployment.

16. The tool of claim 1, wherein one or more of the probes comprises a stabilizing element positioned at a predetermined distance from the probe tip thereof, the stabilizing element configured so as to limit the depth which the probe can penetrate into the wall of the lumen upon deployment.

17. The tool of claim 1, wherein one or more of the probes comprises a plurality of electrodes, arranged along a length thereof in relation to the probe tips thereof, the electrodes configured to convey precise signals pertaining to at least one of an electrophysiological activity of an adjacent tissue site in the vicinity thereof and an impedance between the electrodes during deployment.

18. The tool of claim 17, wherein the conveyed signals relate to the proximity of electrophysiologically active tissues in the vicinity of the wall of the lumen in relation to the probe.

19. The tool of claim 1, wherein one or more of the probes is sized and dimensioned so as to fit within a precapillary arteriole positioned within the wall of the lumen.

20. The tool of claim 1, further comprising one or more additional electrodes disposed on the elongate member, and wherein the controller is configured to generate the corrective signal by monitoring the one or more physiological parameters utilizing the one or more additional electrodes.

21. The tool of claim 1, wherein the controller is configured to generate the corrective signal based on monitored physiologic parameters obtained utilizing one or more additional electrodes disposed on an additional tool.

22. A system, comprising:
a tool configured to monitor an electrophysiological activity in a vicinity of an anatomical site in a vicinity of an organ or vessel in a body, and to perform a surgical procedure on the anatomical site; and
a control unit configured to accept signals from the tool, and to at least one of: adjust the surgical procedure dependent upon the signals, display the signals, evaluate the surgical procedure dependent upon the signals, plan a surgical path for the surgical procedure dependent upon the signals, and determine the extent of the procedure dependent upon the signals;
wherein the tool comprises:
an elongate member with a distal tip and a control end, the distal tip thereof shaped and dimensioned so as to fit within a lumen, the elongate member shaped and dimensioned so as to extend from an entry site on the body into the lumen; and
one or more probes each configured with a probe tip, the probes deploy-ably coupled with the distal tip of the elongate member and at least one of electrically, mechanically, and fluidly coupled to the control end of the elongate member, the probe tips shaped so as to at least one of penetrate into and penetrate through a wall of the lumen upon deployment from the elongate member, one or more of the probes comprising one or more electrodes electrically coupled to the probes, one or more of the electrodes configured to at least one of convey a signal associated with an electrophysiological activity and to alter the electrophysiological activity upon deployment; and
a controller configured:
to record one or more electrophysiological signals from monitored electrophysiological activity within the vicinity of one or more of the electrodes coupled to the probes;
to cancel one or more movement artifacts from the recorded electrophysiological signals utilizing a corrective signal, the corrective signal being generated from monitoring one or more physiological parameters of the subject at a location remote from the vicinity of the one or more electrodes coupled to the probes; and
wherein the system is configured to alter electrophysiological activity in the vicinity of the anatomical site in the vicinity of the organ or vessel in the body accessible via the lumen.

23. The system of claim 22, wherein the surgical procedure is selected from an ablation, an excision, a cut, a burn, a radio frequency ablation, a cryoablation, a radiosurgical procedure, delivery of energy, an ultrasonic ablation, an abrasion, a biopsy, delivery of a substance, or a combination thereof.

24. The system of claim 22, further comprising at least one of a stimulation electrode and an ablation electrode configured so as to convey at least one of a pulsatile and a radio frequency signal to the anatomical site or a site coupled thereto from the control unit, the tool configured to convey one or more feedback signals measured by one or more of the electrodes coupled to the probes and that are related to the at least one pulsatile and radio frequency signal back to the control unit.

25. The system of claim 24, wherein one or more of the feedback signals are related to at least one of an electrode impedance, a bioimpedance, a local electrical field, and an electrophysiological response to the at least one pulsatile and radio frequency signal.

26. The system of claim 22, wherein the control unit is configured to use one or more of the signals to locate the anatomical site with respect to one or more components of the tool.

27. A method, comprising:
penetrating one or more probe tips of one or more probes at least one of into and through a wall of a vessel from within the vessel, the one or more probes being deployably coupled with a distal tip of an elongate member of a tool, wherein one or more electrodes are coupled to one or more of the probes; and
recording one or more electrophysiological signals from electrophysiological activity monitored within the vicinity of one or more of the electrodes coupled to the probes;
generating a corrective signal from monitoring one or more physiological parameters at a location remote from the vicinity of the one or more electrodes coupled to the probes; and
canceling one or more movement artifacts from the recorded electrophysiological signals utilizing the corrective signal to enable at least one of monitoring and altering electrophysiological activity in the vicinity of the vessel.

28. The method of claim 27, wherein the recording step comprises recording one or more of an evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, tissue tone, nerve traffic, or combinations thereof in the vicinity of the electrode.

29. The method of claim 27, further comprising electrically isolating one or more of the electrodes from the lumen of the vessel.

30. The method of claim 27, further comprising delivering a substance to the vicinity of the vessel and recording the effect of the substance on the electrophysiological activity.

31. The method of claim 27, further comprising recording a first electrophysiological activity level, at least one of applying one or more of an energy and a substance within the vicinity of the vessel and applying the one or more energy and substance through the vessel wall, recording a second electrophysiological activity level, and comparing the first and second activity levels to determine if the energy and substance application had a significant effect on activity, or if further energy and substance should be applied.

32. The method of claim 31, further comprising determining if sufficient energy has been applied to the treatment site based on the comparison.

33. The method of claim 31, further comprising mapping electrophysiological activity in the vicinity of the organ or vessel using the first activity level.

34. The method of claim 31, further comprising recording electrophysiological activity in a proximal region and a distal region measured along the length of the organ or vessel as spaced with respect to one or more of an energy and a substance delivery site, to determine if the energy application affected the electrophysiological activity in the vicinity of the delivery site.

35. The method of claim 31, comprising determining if the energy application was sufficient to form a neural block using the comparison.

36. The method of claim 35, further comprising applying sufficient energy to the treatment site to form a temporary block and assessing if the change in electrophysiological activity is desirable, if so, applying sufficient energy to the treatment site so as to form a substantially irreversible block.

37. The method of claim 31, wherein the energy is in the form of a radio frequency current, an ultrasonic wave, or thermal energy.

* * * * *

UNITED STATES PATENT AND TRADEMARK OFFICE
CERTIFICATE OF CORRECTION

PATENT NO. : 9,956,034 B2
APPLICATION NO. : 14/439989
DATED : May 1, 2018
INVENTOR(S) : Landy Toth et al.

It is certified that error appears in the above-identified patent and that said Letters Patent is hereby corrected as shown below:

On the Title Page

Item (54) and in the Specification, Column 1, Line 4, in the title, please delete "WELL" and replace it with --WALL--

In the Specification

Column 2, Line 22, please delete the "," after "provide"

Column 10, Line 6, please add "to" after "According"

Column 13, Line 60, please delete "slide ably" and replace it with --slide-ably--

Column 14, Line 55, please delete "kokm" and replace it with --kohm--

Column 27, Line 41, please add "which" between "microsensors" and "may"

Column 42, Line 40, please delete "deploy ably" and replace it with --deploy-ably--

Column 46, Line 3, please delete "slide ably" and replace it with --slide-ably--

In the Claims

Claim 3, Column 65, Line 35, please add a "," after "1"

Claim 3, Column 65, Line 35, please delete "comprises" and replace it with --comprising--

Claim 11, Column 66, Line 14, please delete "comprises" and replace it with --comprising--

Signed and Sealed this
Ninth Day of October, 2018

Andrei Iancu
*Director of the United States Patent and Trademark Office*

Claim 12, Column 66, Line 23, please add a "," after "7"

Claim 12, Column 66, Line 23, please delete "comprises" and replace it with --comprising--